(12) United States Patent
Raj et al.

(10) Patent No.: US 9,896,720 B2
(45) Date of Patent: Feb. 20, 2018

(54) IMAGING INDIVIDUAL MRNA MOLECULES USING MULTIPLE SINGLY LABELED PROBES

(75) Inventors: Arjun Raj, Philadelphia, PA (US); Sanjay Tyagi, New York, NY (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 132 days.

(21) Appl. No.: 13/062,975

(22) PCT Filed: Sep. 10, 2009

(86) PCT No.: PCT/US2009/056564
§ 371 (c)(1),
(2), (4) Date: Jan. 25, 2012

(87) PCT Pub. No.: WO2010/030818
PCT Pub. Date: Mar. 18, 2010

(65) Prior Publication Data
US 2012/0129165 A1 May 24, 2012

Related U.S. Application Data

(60) Provisional application No. 61/191,724, filed on Sep. 10, 2008.

(51) Int. Cl.
*C12Q 1/68* (2006.01)
(52) U.S. Cl.
CPC .................................. *C12Q 1/6827* (2013.01)
(58) Field of Classification Search
CPC ................................................... C12Q 1/6841
See application file for complete search history.

(56) References Cited

U.S. PATENT DOCUMENTS

| | | | |
|---|---|---|---|
| 5,866,331 A * | 2/1999 | Singer et al. | 435/6.11 |
| 5,962,332 A * | 10/1999 | Singer et al. | 436/94 |
| 5,985,549 A | 11/1999 | Singer et al. | |
| 6,203,986 B1 * | 3/2001 | Singer et al. | 435/6.11 |
| 6,242,184 B1 * | 6/2001 | Singer et al. | 435/6.14 |
| 6,329,152 B1 * | 12/2001 | Patterson | C12Q 1/6841 435/6.16 |
| 2002/0177157 A1 | 11/2002 | Luo et al. | |
| 2005/0214824 A1 | 9/2005 | Balaban | |
| 2006/0199213 A1 * | 9/2006 | Capodieci et al. | 435/6 |
| 2007/0099196 A1 * | 5/2007 | Kauppinen et al. | 435/6 |
| 2008/0058275 A1 | 3/2008 | Inouye et al. | |
| 2008/0113344 A1 | 5/2008 | Wirtz et al. | |

FOREIGN PATENT DOCUMENTS

| | | |
|---|---|---|
| WO | 97/14816 A1 | 4/1997 |
| WO | 2002022874 A2 | 3/2002 |
| WO | 2006132710 A1 | 12/2006 |
| WO | 2007001986 A2 | 1/2007 |

OTHER PUBLICATIONS

Raj et al. (2006) Stochastic mRNA Synthesis in Mammalian Cells. PLOS Biology, 4(10):e309, pp. 1707-1719.*
Chan et al. (2005) Method for multiplex cellular detection of mRNAs using quantum dot fluorescent in situ hybridization. Nucleic Acids Research, 33(18):e161, pp. 1-8.*
Moter et al. (2000) Fluorescence in situ hybridization (FISH) for direct visualization of microorganisms. Journal of Microbiological Methods, 41:85-112).*
Biosearch Technologies homepage (see screenshot obtained from <https://www.biosearchtech.com/> on Jul. 17, 2014), 1 page.*
Vargas et al. (2005) Mechanism of mRNA transport in the nucleus. PNAS, 102(47):17008-17013.*
Silverman et al. (2005) Quenched probes for highly specific detection of cellular RNAs. Trends in Biotechnology, 23(5):225-230.*
Wagner et al. (1998) In situ detection of a virulence factor mRNA and 16S rRNA in Listeria monocytogenes. FEMS Microbiology Letters, 160:159-168.*
Santangelo et al. (2004) Dual FRET molecular beacons for mRNA detection in living cells. Nucleic Acids Research, 32(6):e57, pp. 1-9.*
Kiss, T. (2001) Small nucleolar RNA-guided post-transcriptional modification of cellular RNAs. The EMBO Journal, 20(14):3617-3622.*
Kuhn et al., Hybridization of DNA and PNA Molecular Beacons to Single-Stranded and Double-Stranded DNA Targets. Journal of the American Chemical Society 124( 6): 1097-1103. (2002).
Tyagi et al., Molecular Beacons: Probes that Fluoresce upon Hybridization. Nature Biotechnology, 14( 3): 303-308. (1996).
Femino et al., "Visualization of single RNA transcripts in situ," Science (Apr. 24, 1998): 280(5363); pp. 585-590.
Sanghoon et al., "Use of multiple rRNA-targeted fluorescent probes to increase signal strength and measure cellular RNA from natural planktonic bacteria," Marine Ecology Progress Series (Nov. 4, 1993): vol. 101, pp. 193-201.
Raj et al., "Imaging individual mRNA molecules using multiple singly labeled probes," Nature Methods (Oct. 1, 2008): 5 (10):877-879.
Capodieci et al., "Gene expression profiling in single cells within tissue," Nature Methods (Sep. 2005): 2 (9):663-665.
Chou et al., "Colocalization of Different Influenza Viral RNA Segments in the Cytoplasm before Viral Budding as Shown by Single-Molecule Sensitivity FISH Analysis," PLOS pathogens (May 2013) vol. 9, Issue 5, pp. 1-17.

(Continued)

*Primary Examiner* — Neil P Hammell
(74) *Attorney, Agent, or Firm* — Fox Rothschild LLP

(57) ABSTRACT

A method for probing a target sequence of messenger ribonucleic acid molecules (mRNA's) in a fixed, permeabilized cell, said target sequence including at least 30 non-overlapping probe binding regions of 15-100 nucleotides, comprising immersing said cell in an excess of at least 30 nucleic acid hybridization probes, each singly labeled with the same fluorescent label and each containing a nucleic acid sequence that is complementary to a different probe binding region of said target sequence; washing said fixed cell to remove unbound probes; and detecting fluorescence from said probes.

18 Claims, 29 Drawing Sheets

(56) References Cited

OTHER PUBLICATIONS

Hahn et al., "Detection of mRNA in Streptomyces Cells by whole-cell hybridization with digoxigenin-labeled probes," Applied and Evnironmental Microbiology (Aug. 1993): 59(8):2753-2757.
Hönerlage et al., "Detection of mRNA of nprM in Bacillus megaterium ATCC 14582 Grown in soil by whole-cell hybridization," Arch Microbiol (1995) 163:235-241.
Levsky et al., "Single-Cell Gene Expression Profiling," Science (Aug. 2, 2002): vol. 297, pp. 836-840.
Luebke et al., "Prioritized selection of oligodeoxyribonucleotide probes for efficient hybridization to RNA transcripts," Nucleic Acids Research (2003): 31(2):750-758.
Mir et al., "Determining the influence of structure on hybridization using oligonucleotide arrays," Natuer Biotechnology (Aug. 1999): vol. 17, pp. 788-792.
Pozhitkov et al., "Test of rRNA hybridization to microarrays suggest that hybridization characteristics of oligonucleotide probes for species discrimination cannot be predicted," Nucleic Acids Research (2006): 34(9): pp. e66 1-12.
Rahman et al., "Single-molecule resolution fluorescent in situ hybridization (smFISH) in the yeast *S. cerevisiae*" Chapter 3 at pp. 41-42, in Yaron Shav-Tal (ed.) Imaging Gene Expression: Methods and Protocols, Methods in Molecular Biology, vol. 1042, Springer Science+Business Media (2013).
Randolph et al., "Stability, specificity and fluorescence brightness of multiply-labeled fluorescent DNA probes," Nucleic Acids Research (1997): 25(14):2923-2929.
Schwanhäusser et al., "Global quantification of mammalian gene expression control," Nature (May 19, 2011): vol. 473, pp. 337-342.
Wagner et al., "In situ detection fo avirulence factor mRNA and 16S rRNA in Listeria monocytogenes," FEMS Microbiology Letters (1998) vol. 160, pp. 159-168.
Lee et al., "Use of multiple 16S rRNA-targeted fluorescent probes to increase signal strength and measure cellular RNA from natural planktonic bacteria," Marine Ecology Progress Series (1993); vol. 101, pp. 193-201.

Bratu et al., "Visualizing the distribution and transport of mRNAs in living cells," PNAS (Nov. 11, 2003): 100(23):13308-13313.
Holstege et al, "Dissecting the Regulatory Circuitry of a Eukaryotic Genome," Cell (Nov. 25, 1998): vol. 95, 717-728.
Majlessi et al., "Advantages of 2'-O-methyl oligoribonucleotide probes for detecting RNA targets," Nucleic Acids Research (1998): 26(9)2224-2229.
Pritchard et al., "MicroRNA profiling: approaches and considerations," Nature Review Genetics (May 2012): vol. 13, pp. 358-369.
Tyagi et al., "Multicolor molecular beacons for allele discrimination," Nature Biotechnology (Jan. 1998): vol. 16, pp. 49-53.
Schwanhausser et al., Global quantificationof mammalian gene expression control, Nature (May 19, 2011): vol. 473, pp. 337-342.
Vargas et al., Mechanism of mRNA transport in the nucleas, Supporting Information; http://www.pnas.org/content/suppl/2005/11/04/0505580102.DCI.
Hocine et al., "Promoter-Autonomous Functioning in a Controlled Environment Using Single Molecule Fish," Nature/ScientificReports (Published May 28, 2015) pp. 1-11.
Vera et al., "The translation elongation factore eEF1A1 couples transcription to translation during heat shock response," eLIFE (Published Sep. 16, 2014) pp. 1-19.
Dirks et al., "RNAs radiate from gene to cytoplasm as revealed by fluorescence in situ hybridization," Journal of Cell Science (1995); 108:2565-2572.
Taneja et al., "Use of Oligodeoxynucleotide Probes for Quantitative In Situ Hybridization to Actin mRNA," Analytical Biochemistry (1987); 166:389-398.
Femino et al., "Visualization of Single Molecules of mRNA in Situ," Biophotonics, (2003) pp. 245-304.
Taneja et al., "Detection and Localization of Actin mRNA Isoforms in Chicken Muscle Cells by In Situ Hybridization Using Biotinated Oligonucleotide Probes," Journal of Cellular Biochemistry (1990); 44:241-252.
Paillasson et al., "In Situ Hybridization in Living Cells: Detection of RNA Molecules," Experimental Cell Research (1997); 231:226-233 (Article No. EX963464).
Kosman et al., "MUltiplex Detection of RNA Expression in Drosophila Embryos," Science (Aug. 6, 2004); 305:846.

* cited by examiner

A. Probes for the repeated 3'-UTR multiimer sequence(4 oligos):

TCGACGCGGAGACCACGCTC-GGCTTGTCTTTCGCGCGCAA-TGCGACGCACGCGGATAGTT-AGCTG
AGCTGCGCCTCTGGTGCGAG CCGAACAGAAAGCGCGCGTT ACGCTGCGTGCGCCTATCAA TCGAC

CGGCGACGAGGCACC

GCCGCTGCTCCGTGG

FIG. 11A

B. Probes for l3-actin (48 oligos):

```
                ATGGATGACGATATCGCTGCGCTCGTCGTCGACAACGGCTCCGGCATGTGCAAGGCCGGCTTCGC
                                             CAGCTGTTGCCGAGGCCGTA    GTTCCGGCCGAAGCG

GGGCGACGATGCTCCCCGGGCCGTCTTCCCCTCCATCGTGGGCCGCCCTAGGCACCAGGGTGTGATGGTGGGTAT
CCCGC    TACGAGGGGCCCGGCAGAAG    AGGTAGCACCCGGCGGGATC    GGTCCCACACTACCACCCAT

GGGTCAGAAGGACTCCTACGTGGGCGACGAGGCCCAGAGCAAGAGAGGCATCCTGACCCTGAAGTACCCCATTGA
    CAGTCTTCCTGAGGATGCAC    CTGCTCCGGGTCTCGTTCTC    GTAGGACTGGGACTTCATGG    AACT

ACACGGCATTGTCACCAACTGGGACGATATGGAGAAGATTTGGCACCACACTTTCTACAATGAGCTGCGTGTGGC
TGTGCCGTAACAGTGG    ACCCTGCTATACCTCTTCTA    CGTGGTGTGAAAGATGTTAC    ACGCACACCG

CCCTGAGGAGCACCCTGTGCTGCTCACCGAGGCCCCTCTGAACCCTAAGGCCAACCGTGAAAAGATGACCCAGAT
GGGACTCCTC    GGACACGACGAGTGGCTCCG    AGACTTGGGATTCCGGTTGG    TTTTCTACTGGGTCTA

CATGTTTGAGACCTTCAACACCCCAGCCATGTACGTAGCCATCCAGGCTGTGTTGTCCCTGTATGCCTCTGGTCG
GTAC    CTCTGGAAGTTGTGGGGTCG    CATGCATCGGTAGGTCCGAC    ACAGGGACATACGGAGACCA

TACCACTGGCATTGTGATGGACTCCGGAGACGGGGTCACCCACACTGTGCCCATCTATGAGGGTTACGCGCTCCC
    TGGTGACCGTAACACTACCT    GCCTCTGCCCCAGTGGGTGT    ACGGGTAGATACTCCCAATG    GAGGG

TCATGCCATCCTGCGTCTGGACCTGGCTGGCCGGGACCTGACAGACTACCTCATGAAGATCCTGACCGAGCGTGG
AGTACGGTAGGACGC    CCTGGACCGACCGGCCCTGG    GTCTGATGGAGTACTTCTAG    TGGCTCGCACC

CTACAGCTTCACCACCACAGCTGAGAGGGAAATCGTGCGTGACATTAAAGAGAAGCTGTGCTATGTTGCCCTAGA
GATGTCGAA    GTGGTGTCGACTCTCCCTTT    ACGCACTGTAATTTCTCTTC    ACGATACAACGGGATCT

CTTCGAGCAAGAGATGGCCACTGCCGCATCCTCTTCCTCCCTGGAGAAGAGCTATGAGCTGCCTGACGGTCAGGT
GAA    CGTTCTCTACCGGTGACGGC    GGAGAAGGAGGGACCTCTTC    ATACTCGACGGACTGCCAGT

CATCACTATCGGCAATGAGCGGTTCCGATGCCCCGAGGCTCTCTTCCAGCCTTCCTTCCTGGGTATGGAATCCTG
GTAGTGATAGCCGTTACTCG    AGGCTACGGGGCTCCGAGAG    GTCGGAAGGAAGGACCCATA    TAGGAC

TGGCATCCATGAAACTACATTCAATTCCATCATGAAGTGTGACGTTGACATCCGTAAAGACCTCTATGCCAACAC
ACCGTAGGTACTTT    GTAAGTTAAGGTAGTACTTC    CTGCAACTGTAGGCATTTCT    GATACGGTTGTG

AGTGCTGTCTGGTGGCACCACCATGTACCCAGGCATTGCTGACAGGATGCAGAAGGAGATTACTGCCCTGGCTCC
TCACGACA    CACCGTGGTGGTACATGGGT    TAACGACTGTCCTACGTCTT    CTAATGACGGGACCGAGG

TAGCACCATGAAGATCAAGATCATTGCTCCTCCTGAGCGCAAGTACTCTGTGTGGATTGGTGGCTCTATCCTGGC
AT    GGTACTTCTAGTTCTAGTAA    GGAGGACTCGCGTTCATGAG    CACCTAACCACCGAGATAGG    G

CTCACTGTCCACCTTCCAGCAGATGTGGATCAGCAAGCAGGAGTACGATGAGTCCGGCCCCTCCATCGTGCACCG
GAGTGACAGGTGGAAGGTC    TACACCTAGTCGTTCGTCCT    GCTACTCAGGCCGGGAGGT    ACGTGGC

CAAATGCTTCTAG
GTTTACGAAGATC
```

FIG. 11B

C. Probes for COX·2 (48 oligos):

```
             ATGCTCGCCCGCGCCCTGCTGCTGTGCGCGGTCCTGGCGCTCAGCCATACAGCAAATCCTTGCTG
             CGAGCGGGCGCGGGACGACG                              TGTCGTTTAGGAACGAC

TTCCCACCCATGTCAAAACCGAGGTGTATGTATGAGTGTGGGATTTGACCAGTATAAGTGCGATTGTACCCGGAC
AAG              TTGGCTCCACATACATACTC       AACTGGTCATATTCACGCTA

AGGATTCTATGGAGAAAACTGCTCAACACCGGAATTTTTGACAAGAATAAAATTATTTCTGAAACCCACTCCAAA
             ACCTCTTTTGACGAGTTGTG                       AAGACTTTGGGTGAGGTTT

CACAGTGCACTACATACTTACCCACTTCAAGGGATTTTGGAACGTTGTGAATAACATTCCCTTCCTTCGAAATGC
G              TGAATGGGTGAAGTTCCCTA                     AGGGAAGGAAGCTTTACG

AATTATGAGTTATGTGTTGACATCCAGATCACATTTGATTGACAGTCCACCAACTTACAATGCTGACTATGGCTA
TT         ACACAACTGTAGGTCTAGTG        ACTGTCAGGTGGTTGAATGT         ACCGAT

CAAAAGCTGGGAAGCCTTCTCTAACCTCTCCTATTATACTAGAGCCCTTCCTCCTGTGCCTGATGATTGCCCGAC
GTTTTCGACCCTTC             AATATGATCTCGGGAAGGAG

TCCCTTGGGTGTCAAAGGTAAAAAGCAGCTTCCTGATTCAAATGAGATTGTGGAAAAATTGCTTCTAAGAAGAAA
             TCCATTTTTCGTCGAAGGAC       ACTCTAACACCTTTTTAACG     TCTTCTTT

GTTCATCCCTGATCCCCAGGGCTCAAACATGATGTTTGCATTCTTTGCCCAGCACTTCACGCATCAGTTTTTCAA
CAAGTAGGGACT                   ACGTAAGAAACGGGTCGTGA               AAGTT

GACAGATCATAAGCGAGGGCCAGCTTTCACCAACGGGCTGGGCCATGGGGTGGACTTAAATCATATTTACGGTGA
CTGTCTAGTATTCGC           AGTGGTTGCCCGACCCGGTA              TAAATGCCACT

AACTCTGGCTAGACAGCGTAAACTGCGCCTTTTCAAGGATGGAAAAATGAAATATCAGATAATTGATGGAGAGAT
TTGAGACCG           TTGACGCGGAAAAGTTCCTA                     ACTACCTCTCTA

GTATCCTCCCACAGTCAAAGATACTCAGGCAGAGATGATCTACCCTCCTCAAGTCCCTGAGCATCTACGGTTTGC
CATAGGAG           TCTATGAGTCCGTCTCTACT

TGTGGGGCAGGAGGTCTTTGGTCTGGTGCCTGGTCTGATGATGTATGCCACAATCTGGCTGCGGGAACACAACAG
             ACCAGACCACGGACCAGACT                AGACCGACGCCCTTGTGTTG

AGTATGCGATGTGCTTAAACAGGAGCATCCTGAATGGGGTGATGAGCAGTTGTTCCAGACAAGCAGGCTAATACT
    ACGCTACACGAATTTGTCCT         ACCCCACTACTCGTCAACAA            TATGA

GATAGGAGAGACTATTAAGATTGTGATTGAAGATTATGTGCAACACTTGAGTGGCTATCACTTCAAACTGAAATT
CTATCCTCTCTGATA             ATACACGTTGTGAACTCACC             TGACTTTAA

TGACCCAGAACTACTTTTCAACAAACAATTCCAGTACCAAAATCGTATTGCTGCTGAATTTAACACCCTCTATCA
ACTGGGTCTTG      AGTTGTTTGTTAAGGTCATG          ACGACGACTTAAATTGTGGG

CTGGCATCCCCTTCTGCCTGACACCTTTCAAATTCATGACCAGAAATACAACTATCAACAGTTTATCTACAACAA
                                AAGTACTGGTCTTTATGTTG

CTCTATATTGCTGGAACATGGAATTACCCAGTTTGTTGAATCATTCACCAGGCAATTGCTGGCAGGGTTGCTGG
         ACGACCTTGTACCTTAATGG      ACAACTTAGTAAGTGGTCCG
```

FIG. 11C

```
TGGTAGGAATGTTCCACCCGCAGTACAGAAAGTATCACAGGCTTCCATTGACCAGAGCAGGCAGATGAAATACCA
             TCATAGTGTCCGAAGGTAAC

GTCTTTTAATGAGTACCGCAAACGCTTTATGCTGAAGCCCTATGAATCATTTGAAGAACTTACAGGAGAAAAGGA
    AATTACTCATGGCGTTTGCG                     AGTAAACTTCTTGAATGTCC      TCCT

AATGTCTGCAGAGTTGGAAGCACTCTATGGTGACATCGATGCTGTGGAGCTGTATCCTGCCCTTCTGGTAGAAAA
    TTACAGACGTCTCAAC        ACCACTGTAGCTACGACACC      AGGACGGGAAGACCATCTTT

GCCTCGGCCAGATGCCATCTTTGGTGAAACCATGGTAGAAGTTGGAGCACCATTCTCCTTGAAAGGACTTATGGG
                ACCACTTTGGTACCATCTTC            AGAGGAACTTTCCTGAATAC

TAATGTTATATGTTCTCCTGCCTACTGGAAGCCAAGCACTTTTGGTGGAGAAGTGGGTTTTCAAATCATCAACAC
      TATACAAGAGGACGGATGAC              AACCACCTCTTCACCCAAAA

TGCCTCAATTCAGTCTCTCATCTGCAATAACGTGAAGGGCTGTCCCTTTACTTCATTCAGTGTTCCAGATCCAGA
       AAGTCAGAGAGTAGACGTTA                   ATGAAGTAAGTCACAAGGTC

GCTCATTAAAACAGTCACCATCAATGCAAGTTCTTCCCGCTCCGGACTAGATGATATCAATCCCACAGTACTACT
          TGTCAGTGGTAGTTACGTTC

AAAAGAACGTTCGACTGAACTGTAG
  TTCTTGCAAGCTGACTTGAC
```

FIG. 11C (Cont.)

**D. Probes for *d2EGFP* (48 oligos):**

```
            GCGGATGGTGAGCAAGGGCGAGGAGCTGTTCACCGGGGTGGTGCCCATCCTGGTCGAGCTGGACG
              CTACCACTCGTTCCCGC    TCGACAAGTGGCCCCAC    GGGTAGGACCAGCTCGA    GC

GCGACGTAAACGGCCACAAGTTCAGCGTGTCCGGCGAGGGCGAGGGCGATGCCACCTACGGCAAGCTGACCCTGA
CGCTGCATTTGCCGG    TCAAGTCGCACAGGCCG    CCGCTCCCGCTACGGTG    GCCGTTCGACTGGGACT

AGTTCATCTGCACCACCGGCAAGCTGCCCGTGCCCTGGCCCACCCTCGTGACCACCCTGACCTACGGCGTGCAGT
    AGTAGACGTGGTGGCCG    GACGGGCACGGGACCGG    GGAGCACTGGTGGGACT    TGCCGCACGTCA

GCTTCAGCCGCTACCCCGACCACATGAAGCAGCACGACTTCTTCAAGTCCGCCATGCCCGAAGGCTACGTCCAGG
CGAAG    GCGATGGGGCTGGTGTA    CGTCGTGCTGAAGAAGT    GGCGGTACGGGCTTCCG    CAGGTCC

AGCGCACCATCTTCTTCAAGGACGACGGCAACTACAAGACCCGCGCCGAGGTGAAGTTCGAGGGCGACACCCTGG
TCGCGTGGTA    GAAGTTCCTGCTGCCGT    TGTTCTGGGCGCGGCTC    TTCAAGCTCCCGCTGTG    CC

TGAACCGCATCGAGCTGAAGGGCATCGACTTCAAGGAGGACGGCAACATCCTGGGGCACAAGCTGGAGTACAACT
ACTTGGCGTAGCTCG    TCCCGTAGCTGAAGTTC    CTGCCGTTGTAGGACCC    GTTCGACCTCATGTTGA

ACAACAGCCACAACGTCTATATCATGGCCGACAAGCAGAAGAACGGCATCAAGGTGAACTTCAAGATCCGCCACA
    TGTCGGTGTTGCAGATA    TACCGGCTGTTCGTCTT    GCCGTAGTTCCACTTGA    TCTAGGCGGTGT

ACATCGAGGACGGCAGCGTGCAGCTCGCCGACCACTACCAGCAGAACACCCCCATCGGCGACGGCCCCGTGCTGC
TGTAG    CTGCCGTCGCACGTCGA    GCTGGTGATGGTCGTCT    GGGGGTAGCCGCTGCCG    CACGACG

TGCCCGACAACCACTACCTGAGCACCCAGTCCGCCCTGAGCAAAGACCCCAACGAGAAGCGCGATCACATGGTCC
ACGGGCTGTT    GATGGACTCGTGGGTCA    GGGACTCGTTTCTGGGG    CTCTTCGCGCTAGTGTA    GG

TGCTGGAGTTCGTGACCGCCGCCGGGATCACTCTCGGCATGGACGAGCTGTACAAGAAGCTTAGCCATGGCTTCC
ACGACCTCAAGCACT    GGCGGCCCTAGTGAGAG    TACCTGCTCGACATGTT    CGAATCGGTACCGAAGG

CGCCGGAGGTGGAGGAGCAGGATGATGGCACGCTGCCCATGTCTTGTGCCCAGGAGAGCGGGATGGACCGTCACC
      GCCTCCACCTCCTCGTC    CTACCGTGCGACGGGTA    AACACGGGTCCTCTCGC    ACCTGGCAGTGG

CTGCAGCCTGTGCTTCTGCTAGGATCAATGTGTAGGAATTCGTGACATGATAAGATACATTGATGAGTTTGGACA
GACGT    ACACGAAGACGATCCTA    TTACACATCCTTAAGCA    TACTATTCTATGTAACT    CAAACCTGT

AACCACAACTAGAATGCAGTGAAAAAAATGCTTTATTTGTGAAATTTGTGATGCTATTGCTTTATTTG
TTGGTGTT    CTTACGTCACTTTTTTT    AAATAAACACTTTAAAC    ACGATAACGAAATAAAC
```

FIG. 11D

**E. Probes for *dpp* (48 oligos):**

ATGCGCGCATGGCTTCTACTCCTCGCAGTGCTGGCGACTTTTCAAACGATTGTTCGAGTTGCTAG
CGCGCGTACCGAAGATGAGG    CACGACCGCTGAAAAGTTTG    AGCTCAACGATC

CACCGAGGATATATCCCAGAGATTCATCGCCGCCATAGCGCCCGTTGCCGCTCATATTCCGCTGGCATCAGCATC
GTGGCTCC    GTAGCGGCGGTATCGCGGGC    GGCGACCGTAGTCGTAG

AGGATCAGGATCAGGACGATCTGGATCTAGATCGGTAGGAGCCTCGACCAGCACAGCATTAGCAAAAGCATTTAA
TCC    GCCATCCTCGGAGCTGGTCG

TCCATTCAGCGAGCCCGCCTCGTTCAGTGATAGTGATAAAAGCCATCGGAGTAAAACAAACAAAAAACCTAGCAA
GTCGCTCGGGCGGAGCAAGT    TCACTATTTTCGGTAGCCTC

AAGTGACGCGAACCGACAGTTCAACGAAGTGCATAAGCCAAGAACAGACCAATTAGAAAATTCCAAAAATAAGTC
GCGCTTGGCTGTCAAGTTGC

TAAACAATTAGTTAATAAACCCAACCACAACAAAATGGCTGTCAAGGAGCAGAGGAGCCACCACAAGAAGAGCCA
GTTCCTCGTCTCCTCGGTGG    CTCGGT

CCACCATCGCAGCCACCAGCCAAAGCAGGCCAGTGCATCCACAGAATCTCATCAATCCTCGTCGATTGAATCAAT
GGTGGTAGCGTCGG    CGTCCGGTCACGTAGGTGTC

CTTCGTGGAGGAGCCGACGCTGGTGCTCGACCGCGAGGTGGCCTCCATCAACGTGCCCGCCAACGCCAAGGCCAT
GCACCTCCTCGGCTGCGACC    GCACGGGCGGTTGCGGTTCC

CATCGCCGAGCAGGGCCCGTCCACCTACAGCAAGGAGGCGCTCATCAAGGACAAGCTGAAGCCAGACCCCTCCAC
GGCTCGTCCCGGGCAGGTGG    TCGACTTCGGTCTGGGGAGG

TCTAGTCGAGATCGAGAAGAGCCTGCTCTCGCTGTTCAACATGAAGCGGCCGCCCAAGATCGACCGCTCCAAGAT
CTCTTCTCGGACGAGAGCGA    GGCGGGTTCTAGCTGGCGAG

CATCATCCCCGAGCCGATGAAGAAGCTCTACGCCGAGATCATGGGCCACGAGCTCGACTCGGTCAACATCCCCAA
AGTAGGGGCTCGGCTACTTC    CGGCTCTAGTACCCGGTGCT    GTAGGGGTT

GCCGGGTCTGCTGACCAAGTCGGCCAACACAGTGCGAAGTTTTACACACAAAGATAGTAAAATCGACGATCGATT
CGGCCCAGACG    TTCAGCCGGTTGTGTCACGC

TCCGCACCACCACCGGTTTCGGCTGCACTTCGACGTGAAGAGCATTCCCGCCGACGAGAAGCTGAAGGCGGCGGA
GGTGGTGGCCAAAGCCGACG    GCTCTTCGACTTCCGCCGCC

GCTGCAGCTGACCCGGGACGCACTCAGTCAACAGGTGGTGGCCAGCAGATCGTCGGCGAATCGGACGCGCTACCA
GTCGACTGGGCCCTGCGTGA    CCACCGGTCGTCTAGCAGCC    GCCTGCGCGATGGT

GGTGCTTGTCTACGACATCACGCGCGTCGGGGTGCGTGGTCAGCGGGAGCCGAGCTATCTGCTGTTGGACACCAA
CCACGA    GTGCGCGCAGCCCCACGCAC    CCTGTGGTT

GACGGTCCGGCTTAACAGCACGGACACGGTGAGCCTCGATGTCCAGCCGGCCGTGGACCGGTGGCTGGCGAGTCC
CTGCCAGGCCG    CGTGCCTGTGCCACTCGGAG    CGGCACCTGGCCACCGACCG

GCAGCGCAACTACGGACTGCTGGTGGAGGTGCGGACGGTCCGCTCCCTGAAGCCGGCCCCACACCACCATGTACG
TCGCGTTGATGCCTGACGAC    CCACGCCTGCCAGGCGAGGG    GTGTGGTGGTACATGC

FIG. 11E

```
CCTGCGCCGCAGCGCGGACGAGGCGCACGAGCGGTGGCAGCACAAGCAGCCGCTCCTGTTCACCTACACGGACGA
GGAC        GTCGCGCCTGCTCCGCGTGC        CCGTCGTGTTCGTCGGCGAG        GGATGTGCCTGCT

CGGGCGGCACAAGGCGCGCTCCATTCGGGACGTGTCTGGCGGAGAGGGCGGTGGCAAGGGCGGCCGGAACAAGCG
GCCCGCC                         GACCGCCTCTCCCGCCACCG                           C

GCAGCCGAGACGGCCTACGAGGCGCAAGAACCACGACGACACCTGCCGGCGGCACTCGCTGTACGTGGACTTCTC
CGTCGGCTCTGCCGGATGC                 GTGGACGGCCGCCGTGAGCG                     GAG

GGACGTGGGCTGGGACGACTGGATTGTGGCGCCTCTGGGCTACGATGCATATTACTGCCACGGGAAGTGCCCCTT
CCTGCACCCGACCCTGC       ACACCGCGGAGACCCGATGC                         CACGGGGAA

CCCGCTGGCCGACCACTTTAACTCGACCAATCACGCCGTGGTGCAGACCCTGGTCAACAATATGAATCCCGGCAA
GGGCGACCGGC                 AGTGCGGCACCACGTCTGGG                       GGGCCGTT

GGTGCCGAAGGCGTGCTGCGTGCCCACGCAACTGGACAGCGTGGCCATGCTCTATCTCAACGACCAAAGTACGGT
CCACGGCTTCCG        CGCACGGGTGCGTTGACCTG                          GCTGGTTTCATGCCA

GGTGCTGAAGAACTACCAGGAGATGACCGTGGTGGGCTGTGGCTGTCGATAG
CCACG               ACTGGCACCACCCGACACCG
```

FIG. 11E (Cont.)

**F. Probes for *elt-2* (48 oligos):**

```
                    ATGGATAATAACTACAATGATAATGTCAACGGCTGGGCCGAAATGGAACCATCTCAACCAATGGG
                                          GTTGCCGACCCGGCTTTACC    TAGAGTTGGTTACCC

AGGTCTGCGCCTACCAACTCAGAACATGGATCCACCAGAGCAAAATAATGAGTCACAATTGAGTGAACTACCGAG
TCCAG     GGATGGTTGAGTCTTGTACC    TGGTCTCGTTTTATTACTCA     TAACTCACTTGATGGCTC

AATGAAAATTGATAATGATTACGCATCTCCAATTGAACGGCAAAGTGTTATCACAAGTGGCACAAATAACTATGA
TT                          TTAACTTGCCGTTTCACAAT      TTCACCGTGTTTATTGATAC

GCCGAAAGTGGAAACTGTTACATCATTTTTCCATACTGGCATAGACTACTCAAACTTTGGAATGTTGGACCAAAC
    CTTTCACCTTTGACAATGTA    AAAGGTATGACCGTATCTGA     TTTGAAACCTTACAACCTGG

TACCATGCAACCGTTTTATCCTCTTTACAGTGGAATTCCCGTAAACACTCTTGGAACTTTTTCGGATATACAAA
ATGGTACGTTGGCAAAATAG      AATGTCACCTTAAGGGCATT     AGAACCTTGAAAAAGCCCTA    TTT

CTCCATATACGACAAACCCTCTCTGTACGACCCCAGTATTCCTACCATTAACATCCCTTCTACTTATCCAACTGT
GAGGTATATGCTGTTTG     AGACATGCTGGGGTCATAAG     GTAATTGTAGGGAAGATGAA     TTGACA

GGCTCCAACTTACGAATGCGTCAAATGCTCACAAAGTTGTGGGGCCGGGATGAAGGCAGTAAACGGAGGAATGAT
CCGAGGTTGAATGC     GCAGTTTACGAGTGTTTCAA     CCGGCCCTACTTCCGTCATT     TCCTTACTA

GTGCGTCAACTGTTCAACACCAAAAACCACGTATTCTCCTCCAGTCGCGTATAGCACTTCTTTGGGACAACCCCC
CACGCAGTTGA     TTGTGGTTTTGGTGCATAA     AGGTCAGCGCATATCGTGAA     CCCTGTTGGGGG

GATTCTGGAAATACCTTCAGAGCAGCCAACTGCTAAAATTGCCAAGCAATCCTCTAAAAAGTCAAGTAGCTCAAA
CTAAGACC     TGGAAGTCTCGTCGGTTGAC     TTAACGGTTCGTTAGGAGAT     CAGTTCATCGAGTTT

TAGGGGGTCAAACGGATCTGCGTCCCGTCGGCAGGGACTTGTGTGCTCCAATTGCAATGGTACCAACACAACTCT
ATCCC     TTTGCCTAGACGCAGGGCAG     CCCTGAACACACGAGGTTAA     ACCATGGTTGTGTTGAGA

CTGGAGAAGAAATGCTGAAGGAGATCCGGTCTGCAATGCTTGCGGGCTTTACTTCAAACTCCATCACATCCCTCG
GA     TTCTTTACGACTTCCTCTAG     GACGTTACGAACGCCCGAAA     GTTTGAGGTAGTGTAGGGAG

GCCGACCTCAATGAAGAAAGAAGGTGCTTTACAGACAAGAAAGAGAAAATCAAAAAGCGGAGACTCTTCCACACC
    CTGGAGTTACTTCTTTCTTC                          TTTTTCGCCTCTGAGAAGGT

ATCAACGTCACGGGCCCGAGAAAGGAAGTTTGAGAGAGCCTCTTCTTCGACCGAAAAGGCTCAAAGGTCATCTAA
TAGTTGCAGTGCCCGGGCTC     CTTCAAACTCTCTCGGAGAA     CTGGCTTTTCCGAGTTTCCA    ATT

CCGGCGTGCGGGAAGTGCAAAAGCAGACCGAGAACTGAGCACTGCTGCCGTCGCAGCTGCGACTGCCACATATGT
GGCCGCACGCCCTTCAC     TCGTCTGGCTCTTGACTCGT                                TATACA

GTCACATGCCGACTTGTATCCCGTTTCCTCAGCTGCCGTCACCTTGCCAGATCAAACGTACAGTAATTACTATCA
CAGTGTACGGCTGA     AGGGCAAAGGAGTCGACGGC     GAACGGTCTAGTTTGCATGT

ATGGAACACTGCCGCTACAGCTGGGTTGATGATGGTTCCAAACGATCAAAACTACGTGTATGCAGCAACAAACTA
                    ATGTCGACCCAACTACTACC                          TCGTTGTTTGAT

CCAGACTGGCCTAAGACCTGCCGATAACATCCAAGTTCATGTGATGCCAGTTCAGGATGATGAAACCAAAGCTGC
GGTCTGAC    TTCTGGACGGCTATTGTAGG     AGTACACTACGGTCAAGTCC     ACTTTGGTTTCGACG
```

FIG. 11F

```
GGCTCGCGATTTGGAAGCGGTCGACGGAGATTCTTAA
CCGAG     AAACCTTCGCCAGCTGCCTC
```

FIG. 11F (Cont.)

G. Probes for FKBP5 (63 oligos):

```
          ATGACTACTGATGAAGGTGCCAAGAACAATGAAGAAAGCCCCACAGCCACTGTTGCTGAGCAGGG
                        TACTTCCACGGTTCTTG

AGAGGATATTACCTCCAAAAAAGACAGGGGAGTATTAAAGATTGTCAAAAGAGTGGGGAATGGTGAGGAAACGCC
                                                                   TCCTTTGCGG

GATGATTGGAGACAAAGTTTATGTCCATTACAAAGGAAAATTGTCAAATGGAAAGAAGTTTGATTCCAGTCATGA
CTACTAA    CTGTTTCAAATACAGGT    GTTTCCTTTTAACAGTT    CTTTCTTCAAACTAAGG    GTACT

TAGAAATGAACCATTTGTCTTTAGTCTTGGCAAAGGCCAAGTCATCAAGGCATGGGACATTGGGGTGGCTACCAT
ATCTTTACTTGG    ACAGAAATCAGAACCGT    CGGTTCAGTAGTTCCGT    CTGTAACCCCACCGATG

GAAGAAAGGAGAGATATGCCATTTACTGTGCAAACCAGAATATGCATATGGCTCGGCTGGCAGTCTCCCTAAAAT
CTTCTTTCCTCTCTATA    TAAATGACACGTTTGGT    ATACGTATACCGAGCCG    GTCAGAGGGATTTTA

TCCCTCGAATGCAACTCTCTTTTTTGAGATTGAGCTCCTTGATTTCAAAGGAGAGGATTTATTTGAAGATGGAGG
AG    GCTTACGTTGAGAGAAA    CTCTAACTCGAGGAACT    GTTTCCTCTCCTAAATA    TTCTACCTCC

CATTATCCGGAGAACCAAACGGAAAGGAGAGGGATATTCAAATCCAAACGAAGGAGCAACAGTAGAAATCCACCT
GTAATAG    TCTTGGTTTGCCTTTCC    CCCTATAAGTTTAGGTT    TTCCTCGTTGTCATCTT    GTGGA

GGAAGGCCGCTGTGGTGGAAGGATGTTTGACTGCAGAGATGTGGCATTCACTGTGGGCGAAGGAGAAGACCACGA
CCTTCCGGCGAC    ACCTTCCTACAAACTGA    CTCTACACCGTAAGTGA    CCGCTTCCTCTTCTGGT

CATTCCAATTGGAATTGACAAAGCTCTGGAGAAAATGCAGCGGGAAGAACAATGTATTTTATATCTTGGACCAAG
GTAAGGTTAACCTTAAC    TTCGAGACCTCTTTTAC    GCCCTTCTTGTTACATA    TATAGAACCTGGTTC

ATATGGTTTTGGAGAGGCAGGGAAGCCTAAATTTGGCATTGAACCTAATGCTGAGCTTATATATGAAGTTACACT
TA    CAAAACCTCTCCGTCCC    GGATTTAAACCGTAACT    ATTACGACTCGAATATA    TTCAATGTGA

TAAGAGCTTCGAAAAGGCCAAAGAATCCTGGGAGATGGATACCAAAGAAAAATTGGAGCAGGCTGCCATTGTCAA
ATTCTCG    CTTTTCCGGTTTCTTAG    CCTCTACCTATGGTTTC    TTAACCTCGTCCGACGG    CAGTT

AGAGAAGGGAACCGTATACTTCAAGGGAGGCAAATACATGCAGGCGGTGATTCAGTATGGGAAGATAGTGTCCTG
TCTCTTCCCTTG    TATGAAGTTCCCTCCGT    TGTACGTCCGCCACTAA    ATACCCTTCTATCACAG

GTTAGAGATGGAATATGGTTTATCAGAAAAGGAATCGAAAGCTTCTGAATCATTTCTCCTTGCTGCCTTTCTGAA
CAATCTCTACCTTATAC    ATAGTCTTTTCCTTAGC    CGAAGACTTAGTAAAGA    ACGACGGAAAGACTT

CCTGGCCATGTGCTACCTGAAGCTTAGAGAATACACCAAAGCTGTTGAATGCTGTGACAAGGCCCTTGGACTGGA
GG    GGTACACGATGGACTTC    TCTCTTATGTGGTTTCG    ACTTACGACACTGTTCC    AACCTGACCT

CAGTGCCAATGAGAAAGGCTTGTATAGGAGGGGTGAAGCCCAGCTGCTCATGAACGAGTTTGAGTCAGCCAAGGG
GTCACGG    CTCTTTCCGAACATATC    CCCACTTCGGGTCGACG    ACTTGCTCAAACTCAGT    TTCCC

TGACTTTGAGAAAGTGCTGGAAGTAAACCCCCAGAATAAGGCTGCAAGACTGCAGATCTCCATGTGCCAGAAAAA
ACTGAAACTCTT    CGACCTTCATTTGGGGG    TATTCCGACGTTCTGAC    TAGAGGTACACGGTCTT

GGCCAAGGAGCACAACGAGCGGGACCGCAGGATATACGCCAACATGTTCAAGAAGTTTGCAGAGCAGGATGCCAA
CCGGTTCCTCGTGTTGC    CCCTGGCGTCCTATATG    TTGTACAAGTTCTTCAA    TCTCGTCCTACGGTT
```

FIG. 11G

GGAAGAGGCCAATAAAGCAATGGGCAAGAAGACTTCAGAAGGGGTCACTAATGAAAAAGGAACAGACAGTCAAGC
CC    TCCGGTTATTTCGTTAC    TTCTTCTGAAGTCTTCC    GTGATTACTTTTTCCTT    TGTCAGTTCG

AATGGAAGAAGAGAAACCTGAGGGCCACGTATGA
TTACCTT    CTCTTTGGACTCCCGGT

FIG. 11G (Cont.)

H. Probes for FLJ11127 (53 oligos):

```
                ATGGCGGCGACAAGGAGCCCCACGCGGGCAAGGGAGCGGGAGCGGTCTGGCGCTCCCGCCGCAGG
                          TTCCTCGGGGTGCGCCC    CCCTCGCCCTCGCCAGA    CGAGGGCGGCGTCC

AAGTGACCAAGTTCACTCCTGGATGCTAGCTACAAGCCAAGCCTTAGACACTGTCTGGAGAATGGCAAAAGGCTT
TTC    GGTTCAAGTGAGGACCT    ATCGATGTTCGGTCGG    CTGTGACAGACCTCTTA    TTTTCCGAA

TGTGATGTTGGCAGTTTCATTTCTGGTGGCTGCCATCTGCTACTTCCGGAGGCTACATTTATATTCAGGGCACAA
ACACTACA    GTCAAAGTAAAGACCAC    CGGTAGACGATGAAGGC    CGATGTAAATATAAGTC    TGTT

GCTGAAATGGTGGATTGGATATCTGCAGAGAAAATTCAAAAGGAACCTCAGTGTGGAGGCAGAGGTTGATTTACT
CGACTTTACCACC    CCTATAGACGTCTCTTT    GTTTTCCTTGGAGTCAC    TCCGTCTCCAACTAAAT

CAGTTATTGTGCAAGAGAATGGAAAGGAGAGACACCCCGTAACAAGCTGATGAGGAAGGCTTATGAGGAGCTATT
  TCAATAACACGTTCTCT    CTTTCCTCTCTGTGGGG    TGTTCGACTACTCCTTC    ATACTCCTCGATAA

TTGGCGGCATCACATTAAATGTGTTCGACAAGTAAGGAGAGATAACTATGATGCTCTCAGATCAGTGTTATTTCA
AAC    CGTAGTGTAATTTACAC    CTGTTCATTCCTCTCTA    ATACTACGAGAGTCTAG    CAATAAAGT

GATATTCAGCCAGGGCATCTCTTTTCCATCATGGATGAAAGAAAAGGACATTGTTAAGCTTCCTGAAAAACTGCT
CTATAAGT    TCCCGTAGAGAAAAGGT    ACCTACTTTCTTTTCCT    ACAATTCGAAGGACTTT    ACGA

GTTTTCACAAGGTTGTAATTGGATTCAGCAGTACAGTTTTGGTCCTGAGAAGTATACAGGCTCGAATGTGTTTGG
CAAAAGTGTTCCA    TTAACCTAAGTCGTCAT    AAAACCAGGACTCTTCA    GTCCGAGCTTACACAAA

AAAACTACGGAAATATGTGGAATTATTGAAAACACAGTGGACTGAATTTAATGGCATTAGAGATTATCACAAGAG
  TTTGATGCCTTTATACA    TAATAACTTTTGTGTCA    GACTTAAATTACCGTAA    CTAATAGTGTTCTC

AGGAAGTATGTGCAACACCCTTTTTTCAGATGCCATTCTGGAATATAAACTTTATGAAGCTTTAAAGTTCATCAT
TCC    ATACACGTTGTGGGAAA    GTCTACGGTAAGACCTT    TTTGAAATACTTCGAAA    CAAGTAGTA

GCTGTATCAAGTCACTGAAGTTTATGAACAAATGAAGACTAAAAAGGTCATTCCCAGTCTTTTTAGACTCCTGTT
CGACATAG    AGTGACTTCAAATACTT    TACTTCTGATTTTTCCA    AGGGTCAGAAAAATCTG    ACAA

TTCCAGGGAGACATCCTCTGATCCTTTGAGCTTCATGATGAATCACCTGAATTCTGTAGGCGACACATGTGGACT
AAGGTCCCTCTGT    AGACTAGGAAACTCGAA    CTACTTAGTGGACTTAA    ATCCGCTGTGTACACCT

AGAGCAGATTGATATGTTTATACTTGGATACTCCCTTGAAGTAAAGATAAAAGTGTTCAGACTGTTCAAGTTTAA
  CTCGTCTAACTATACAA    TGAACCTATGAGGGAAC    ATTTCTATTTTCACAAG    GACAAGTTCAAATT

CTCCAGAGACTTTGAAGTCTGCTACCCAGAGGAGCCTCTCAGGGACTGGCCGGAGATCTCCCTGCTGACCGAGAA
GAG    TCTGAAACTTCAGACGA    GTCCTCGGAGAGTCC    ACCGGCCTCTAGAGGGA    CTGGCTCTT

CGACCGCCACTACCACATTCCAGTCTTTTAA
GCTGGCGG    TGGTGTAAGGTCAGAAA
```

FIG. 11H

I. Probes for Map2 (72 oligos):

```
              ATGGCTGACGAGAGGAAAGACGAAGGAAAGGCACCACACTGGACATCAGCCTCACTCACAGAGGC
                              CTGCTTCCTTTCCGTGGTGT         CGGAGTGAGTGTCTCCG

AGCTGCACACCCCCACTCGCCAGAGATGAAGGACCAGGGTGGCTCAGGGGAAGGGCTGAGCCGCAGCGCCAATGG
TCG         GTGAGCGGTCTCTACTTCCT         AGTCCCCTTCCCGACTCGGC           CC

ATTTCCATACAGAGAGGAGGAGGAAGGCGCCTTTGGGGAGCACGGGTCACAGGGCACCTATTCAGATACCAAAGA
TAAAGGTATGTCTCTCCT         CGGAAACCCCTCGTGCCCAG         ATAAGTCTATGGTTTCT

GAACGGGATCAACGGAGAGCTGACCTCAGCTGACAGAGAAACAGCAGAGGAAGTGTCTGCAAGGATAGTTCAAGT
CTT         CCTCTCGACTGGAGTCGACT         CGTCTCCTTCACAGACGTTC           CA

AGTCACAGCTGAAGCTGTAGCAGTCCTGAAAGGTGAACAAGAGAAGGAGGCCCAACACAAGGATCAGCCTGCAGC
TCAGTGTCGACTTCGACA         TTTCCACTTGTTCTCTTCCT         TTCCTAGTCGGACGTCG

TCTGCCTTTAGCAGCTGAAGAAACAGTTAATCTGCCACCTTCCCCACCACCATCGCCAGCATCAGAACAAACAGC
AGA         CGACTTCTTTGTCAATTAGA         GGTGGTGGTAGCGGTCGTAG            CG

TGCACTGGAAGAAGCCTCGAAGATGGAATTCCCTGAGCAGCAGAAATTGCCTTCCTCATTCGCTGAGCCTTTAGA
ACGTGACCTTCTTCGGAG         AAGGGACTCGTCGTCTTTAA         AAGCGACTCGGAAATCT

CAAGGAGGAAACGGAGTTTAAGATGCAAAGTAAGCCTGGTGAAGACTTTGAACATGCTGCCTTAGTTCCTCAGCC
GTT         CTCAAATTCTACGTTTCATT         CTGAAACTTGTACGACGGAA            GG

GGACACAAGTAAAACTCCCCAGGATAAAAAGGATCCCCAAGACATGGAAGGAGAAAAGTCGCCTGCCAGTCCATT
CCTGTGTTCATTTTGAGG         TTCCTAGGGGTTCTGTACCT         AGCGGACGGTCAGGTAA

TGCGCAGACTTTCGGTACCAACCTGGAAGACATAAAACAGATCACAGAACCAAGCATAACAGTACCTAGCATTGG
ACG         CCATGGTTGGACCTTCTGTA         TGTCTTGGTTCGTATTGTCA            CC

CCTCTCCGCAGAGCCCCTAGCTCCAAAAGATCAGAAAGACTGGTTCATCGAAATGCCCGTGGAATCAAAGAAGGA
GGAGAGGCGTCTCGGGGA         CTAGTCTTTCTGACCAAGTA         CACCTTAGTTTCTTCCT

TGAATGGGGTTTAGCTGCCCCAATATCTCCTGGCCCCTTGACACCCATGAGGGAAAAAGATGTGCTGGAGGATAT
ACT         CGACGGGGTTATAGAGGACC         GGGTACTCCCTTTTTCTACA            TA

CCCAAGATGGGAAGGAAAGCAGTTTGACTCTCCCATGCCTAGCCCCTTCCACAGTGGAAGTTTCACTCTTCCCTT
GGGTTCTACCCTTCCTTT         AGAGGGTACGGATCGGGGAA         TCAAAGTGAGAAGGGAA

AGATACTGTGAAAGATGAGAGAGTCACAGAAGGGTCACAACCCTTTGCCCCTGTCTTCTTCCAATCAGATGACAA
TCT         CTACTCTCTCAGTGTCTTCC         AAACGGGGACAGAAGAAGGT            TT

AATGTCTCTGCAGGACACCAGTGGTTCAGCTACTTCCAAAGAGAGTTCTAAAGATGAGGAGCCACAGAAAGATAA
TTACAGAGACGTCCTGTG         CGATGAAGGTTTCTCTCAAG         CTCGGTGTCTTTCTATT

AGCAGACAAAGTGGCAGATGTTCCTGTCTCAGAAGCTACCACTGTACTGGGAGATGTTCACAGTCCAGCTGTGGA
TCG         CGTCTACAAGGACAGAGTCT         CATGACCCTCTACAAGTGTC            CT

AGGCTTTGTCGGGGAGAACATTTCAGGAGAAGAAAAGGGTACCACAGATCAAGAGAAAAAGAGACTTCGACACC
TCCGAAACAGCCCCTCTT         CTTCTTTTCCCATGGTGTCT         TTTCTCTGAAGCTGTGG
```

FIG. 11I

```
CAGTGTACAGGAACCTACACTCACTGAAACTGAACCACAGACAAAGCTTGAAGAGACATCAAAGGTTTCCATCGA
GTC           GGATGTGAGTGACTTTGACT           TTCGAACTTCTCTGTAGTTT           CT

AGAAACTGTGGCAAAAGAAGAGGAATCCTTGAAATTAAAAGATGATAAAGCAGGTGTAATTCAGACTTCCACCGA
TCTTTGACACCGTTTTCT         AACTTTAATTTTCTACTATT         TAAGTCTGAAGGTGGCT

GCATTCTTTCTCCAAAGAAGACCAGAAAGGCGAAGAACAGACAATCGAAGCATTAAAACAAGACTCCTTTCCTAT
CGT           TTTCTTCTGGTCTTTCCGCT

AAGTCTAGAACAGGCAGTTACAGATGCAGCCATGGCCACCAAGACCTTGGAAAAGGTTACGTCTGAGCCAGAGGC

AGTAAGTGAAAAGAGAGAAATCCAGGGACTTTTTGAAGAGGATATAGCTGACAAGAGTAAGCTCGAAGGCGCTGG
                                                              CGAGCTTCCGCGACC

GTCTGCAACAGTAGCCGAGGTTGAGATGCCATTTTATGAAGATAAATCAGGGATGTCCAAGTACTTTGAAACATC
CAGAC

TGCATTGAAAGAAGATGTGACCAGAAGCACTGGGTTGGGCAGTGATTACTACGAGCTGAGTGACTCAAGAGGAAA
                     GGTCTTCGTGACCCAACCCG

TGCCCAGGAATCTCTTGATACTGTATCTCCCAAGAACCAACAAGATGAAAAGGAACTTCTGGCAAAAGCTTCCCA
                                                                         AGGGT

GCCTAGTCCTCCAGCACACGAAGCAGGGTACAGCACTCTTGCCCAGAGTTATACATCTGATCATCCGTCCGAGTT
CGGATCAGGAGGTCG

ACCTGAAGAACCAAGTTCTCCTCAAGAAAGAATGTTCACTATTGACCCCAAAGTTTATGGGGAGAAAAGGGACCT

TCATAGTAAGAACAAAGATGATCTGACACTTAGTCGAAGCTTGGGGCTGGGCGGAAGGTCTGCAATAGAACAGAG
                                 GCTTCGAACCCCGACCCGCC

AAGCATGTCCATTAACTTGCCTATGTCTTGCCTTGATTCTATTGCCCTTGGGTTTAACTTTGGCCGGGGCCATGA
                                                               GAAACCGGCCCCGGTACT

TCTTTCCCCTCTGGCTTCTGATATTCTAACCAACACTAGCGGAACGATGGATGAAGGAGATGATTACCTGCCCCC
AG                                                                    GGACGGGGG

CACCACACCTGCAGTGGAGAAGATTCCTTGCTTTCCAATAGAGAGCAAAGAGGAAGAAGATAAGACAGAGCAAGC
GTGGTGTGGAC

AAAAGTGACTGGAGGGCAAACTACCCAAGTTGAAACATCCTCCGAGTCACCCTTCCCAGCCAAAGAATATTACAA
                                     GGCTCAGTGGGAAGGGTCGG

AAATGGCACTGTCATGGCCCCTGACCTGCCTGAGATGCTAGATCTAGCAGGGACCAGGTCCAGATTAGCTTCTGT
         CAGTACCGGGGACTGGACGG          GATCGTCCCTGGTCCAGGTC

GAGTGCAGATGCTGAGGTTGCCAGGAGGAAATCAGTCCCATCGGAGGCTGTGGTTGCAGAGAGCAGTACTGGTTT
                             GTCAGGGTAGCCTCCGACAC
```

FIG. 11I (Cont.)

```
GCCACCTGTTGCTGATGACAGCCAACCCGTAAAACCAGACAGTCAACTTGAAGACATGGGGTACTGTGTGTTCAA

CAAGTACACAGTCCCTCTCCCATCGCCAGTTCAAGACAGTGAGAATTTGTCAGGAGAGAGTGGTTCGTTTTATGA
          GGGAGAGGGTAGCGGTCAAG

AGGAACCGATGACAAAGTCCGTAGAGATTTGGCCACTGACCTTTCACTAATTGAGGTAAAACTTGCAGCTGCTGG

AAGAGTCAAAGATGAATTCACTGCTGAGAAAGAGGCATCTCCACCCTCTTCTGCTGACAAATCAGGACTGAGTAG

GGAGTTTGACCAAGACAGGAAAGCTAATGACAAGCTGGATACTGTCCTAGAAAAGAGCGAAGAGCATGTTGATTC

AAAAGAACATGCCAAGGAGTCAGAAGAGGTTGGGGATAAAGTAGAGCTCTTCGGATTAGGTGTAACCTATGAGCA

AACCTCTGCCAAAGAACTGATAACAACTAAAGAAACAGCACCTGAGAGAGCAGAGAAAGGTCTCAGTTCAGTGCC

AGAGGTAGCTGAGGTAGAAACAACCACAAAAGCTGACCAAGGTCTAGATGTTGCTGCCAAGAAAGATGATCAGAG

TCCATTAGATATAAAAGTCAGTGACTTTGGACAGATGGCTTCTGGGATGAGTGTAGATGCTGGGAAAACCATAGA

GCTTAAGTTCGAGGTTGATCAGCAGCTGACTCTCTCATCCGAAGCACCTCAGGAAACAGATTCATTCATGGGTAT

TGAGTCCAGCCACGTGAAGGATGGTGCCAAAGTCAGTGAAACAGAAGTCAAAGAGAAGGTGGCAAAGCCTGACTT

GGTGCATCAGGAGGCTGTGGACAAAGAAGAGTCCTATGAGTCTAGTGGTGAGCATGAAAGCCTCACCATGGAGTC
                                                                   G

CCTGAAGCCTGATGAGGGCAAGAAAGAAACATCTCCAGAGACATCACTGATACAAGATGAAGTTGCCCTCAAACT
GGACTTCGGACTACTCCCG

GTCTGTAGAAATCCCTTGCCCACCTCCAGTTTCCGAAGCTGATTCATCCATTGATGAGAAGGCGGAGGTCCAGAT
                                                        CTTCCGCCTCCAGGTCTA

GGAATTTATTCAGCTGCCAAAGGAAGAGAGCACAGAGACTCCGGATATACCTGCCATACCTTCTGATGTCACCCA
CC                                                                 CAGTGGGT

GCCACAGCCTGAAGCAGTTGTGTCCGAACCAGCAGAGGTTCGAGGTGAGGAAGAAGAGATCGAAGCTGAGGGAGA
CGGTGTCGGACT

ATATGACAAACTGCTCTTCCGCTCAGACACCCTCCAGATCACCGACCTGCTTGTTCCAGGAAGTAGGGAGGAGTT
              GGCGAGTCTGTGGGAGGTCT

TGTGGAGACCTGCCCAGGGGAGCACAAAGGTGTGGTTGAGTCCGTGGTAACCATCGAGGATGATTTCATCACTGT
     CCTCTGGACGGGTCCCCTCG
```

FIG. 11I (Cont.)

```
AGTACAAACCACGACTGATGAGGGAGAGTTGGGATCCCACAGTGTGCGCTTTGCAGCTCCAGTTCAGCCTGAGGA
                          CCCTAGGGTGTCACACGCGA

AGAAAGGAGACCATACCCTCATGATGAAGAGCTTGAAGTACTGATGGCAGCAGAAGCCCAGGCAGAGCCCAAGGA
                                             CGGGTCCGTCTCGGGTTCCT

TGGCTCTCCAGATGCTCCAGCTACCCCTGAGAAAGAAGAGGTTCCATTCTCAGAATATAAAACAGAAACCTACGA
   CCGAGAGGTCTACGAGGTCG

CGATTACAAAGATGAGACCACCATTGATGACTCCATTATGGATGCCGACAGCCTGTGGGTGGACACTCAAGATGA
                                 CGGCTGTCGGACACCCACCT

TGATAGAAGCATCTTGACAGAGCAGTTAGAAACTATTCCTAAAGAGGAGAGAGCTGAGAAGGAAGCTCGGAGACC
                                                      CCTTCGAGCCTCTGG

GTCTCTCGAGAAACATAGAAAAGAAAAACCTTTTAAAACTGGGAGAGGCAGAATTTCCACTCCTGAAAGAAAAGT
CAGAG

AGCTAAAAAGGAACCTAGCACGGTCTCCAGGGATGAAGTGAGAAGGAAAAAAGCAGTTTATAAGAAGGCTGAACT
              GGATCGTGCCAGAGGTCCCT

TGCTAAAAAATCAGAAGTTCAGGCCCACTCTCCTTCCAGGAAACTCATTTTAAAACCTGCTATCAAATACACTAG

ACCAACTCATCTCTCCTGTGTTAAGCGGAAAACCACAGCAACAAGTGGTGAATCAGCTCAGGCTCCCAGTGCGTT
                                             GTCGAGTCCGAGGGTCACGC

TAAACAGGCGAAGGACAAAGTCACTGATGGAATAACCAAGAGCCCAGAAAAACGTTCTTCCCTCCCAAGACCTTC
                                                      GGGAGGGTTCTGGAAG

CTCCATCCTCCCTCCTCGCAGGGGCGTATCAGGAGACAGGGAGGAGAACTCGTTCTCTCTGAACAGCTCCATCTC
GAGG

TTCAGCACGACGGACCACCAGGTCAGAACCAATTCGCAGAGCAGGAAAAAGCGGCACCTCAACACCTACTACCCC

TGGATCTACTGCAATCACCCCTGGCACTCCTCCAAGCTACTCTTCACGTACCCCAGGCACCCCTGGAACCCCGAG

CTATCCCAGGACACCAGGAACCCCCAAATTTGGCATCTTGGTGCCCAGTGAGAAGAAAGTTGCCATCATTCGCAC

TCCTCCAAAGTCCCCAGCTACTCCCAAGCAGCTTCGGCTCATTAACCAACCTCTGCCAGACCTGAAGAACGTCAA

GTCCAAAATCGGATCAACCGACAACATCAAATACCAGCCTAAGGGGGGTCAGGTACAAATTGTTACTAAGAAGAT

AGACTTAAGCCATGTGACTTCCAAATGTGGCTCTCTAAAGAACATCCGTCACAGGCCAGGTGGTGGACGCGTGAA

GATTGAGAGTGTAAAGCTGGATTTCAAGGAGAAGGCCCAAGCTAAAGTTGGCTCACTTGACAATGCTCACCATGT
```

FIG. 11I (Cont.)

```
ACCTGGAGGTGGTAACGTGAAGATTGACAGCCAAAAGCTGAACTTCCGAGAGCATGCAAAGGCCCGCGTCGACCA

CGGGGCTGAGATCATCACACAGTCGCCAAGCAGGTCAAGCGTGGCGTCTCCCCGGCGACTCAGCAATGTCTCCTC

TTCTGGAAGCATCAACCTGCTCGAATCCCCTCAGCTGGCCACTTTGGCTGAGGACGTCACTGCGGCGCTCGCTAA

GCAGGGCTTGTGA
```

FIG. 11I (Cont.)

**J. Probes for *STL*1 (48 oligos):**

ATGAAGGATTTAAAATTATCGAATTTCAAAGGCAAATTTATAAGCAGAACCAGTCACTGGGGACT
TTAATAGCTTAAAGTTTCCG TATTCGTCTTGGTCAGTGAC

TACGGGTAAGAAGTTGCGGTATTTCATCACTATCGCATCTATGACGGGCTTCTCCCTGTTTGGATACGACCAAGG
TGCCCATTCTTCAACGCCAT AGCGTAGATACTGCCCGAAG ACCTATGCTGGTTCC

GTTGATGGCAAGTCTAATTACTGGTAAACAGTTCAACTATGAATTTCCAGCAACCAAAGAAAATGGCGATCATGA
CAACT AATGACCATTTGTCAAGTTG TTACCGCTAGTACT

CAGACACGCAACTGTAGTGCAGGGCGCTACAACCTCCTGTTATGAATTAGGTTGTTTCGCAGGTTCTCTATTCGT
GTCTGT AATCCAACAAGCGTCCAAG AGCA

TATGTTCTGCGGTGAAAGAATTGGTAGAAAACCATTAATCCTGATGGGTTCCGTAATAACCATCATTGGTGCCGT
ATACAAGACGCCACTT ATTAGGACTACCCAAGGCAT

TATTTCTACATGCGCATTTCGTGGTTACTGGGCATTAGGCCAGTTTATCATCGGAAGAGTCGTCACCGGTGTTGG
AAGATGTACGCGTAAAGCAC ATCCGGTCAAATAGTAGCCT

AACAGGGTTGAATACATCTACTATTCCCGTTTGGCAATCAGAAATGTCAAAAGCTGAAAATAGAGGGTTGCTGGT
AAGGGCAAACCGTTAGTCTT TCGACTTTTATCTCCCAACG

CAATTTAGAAGGTTCCACAATTGCTTTTGGTACTATGATTGCTTATTGGATTGATTTTGGGTTGTCTTATACCAA
AATCTTCCAAGGTGTTAACG TAACCTAACTAAAACCCAAC TGGTT

CAGTTCTGTTCAGTGGAGATTCCCCGTGTCAATGCAAATCGTTTTTGCTCTCTTCCTGCTTGCTTTCATGATTAA
GTCAAGACAAGTCAC AGCAAAAACGAGAGAAGGAC ATT

ACTACCTGAATCGCCACGTTGGCTGATTTCTCAAAGTCGAACAGAAGAAGCTCGCTACTTGGTAGGAACACTAGA
TGATGGACTTAGCGGTG AAGAGTTTCAGCTTGTCTTC

CGACGCGGATCCAAATGATGAGGAAGTTATAACAGAAGTTGCTATGCTTCACGATGCTGTTAACAGGACCAAACA
ACTACTCCTTCAATATTGTC ACGAAGTGCTACGACAATTG TGT

CGAGAAACATTCACTGTCAAGTTTGTTCTCCAGAGGCAGGTCCCAAAATCTTCAGAGGGCTTTGATTGCAGCTTC
GCTCTTTGTAAGTGACA ACAAGAGGTCTCCGTCCAGG AGAAGTCTCCCGAAACTAAC

AACGCAATTTTTCCAGCAATTTACTGGTTGTAACGCTGCCATATACTACTCTACTGTATTATTCAACAAAACAAT
AAATGACCAACATTGCGACG TGATGAGATGACATAATAAG

TAAATTAGACTATAGATTATCAATGATCATAGGTGGGGTCTTCGCAACAATCTACGCCTTATCTACTATTGGTTC
TAGTTACTAGTATCCACCCC AGATGCGGAATAGATGATAA

ATTTTTTCTAATTGAAAAGCTAGGTAGACGTAAGCTGTTTTTATTAGGTGCCACAGGTCAAGCAGTTTCATTCAC
TTCGATCCATCTGCATTCGA ATAATCCACGGTGTCCAGTT

AATTACATTTGCATGCTTGGTCAAAGAAAATAAAGAAAACGCAAGAGGTGCTGCCGTCGGCTTATTTTTGTTCAT
AATGTAAACGTACGAACCAG TTTCTTTTGCGTTCTCCACG AACAAGTA

TACATTCTTTGGTTTGTCTTTGCTATCATTACCATGGATATACCCACCAGAAATTGCATCAATGAAAGTTCGTGC
ATGTAAGAAACC ATGGTACCTATATGGTGGT TCAAGCACG

FIG. 11J

```
ATCAACAAACGCTTTCTCCACATGTACTAATTGGTTGTGTAACTTTGCGGTTGTCATGTTCACCCCAATATTTAT
TAGTTGTTTGC            AACCAACACATTGAAACGCC                            AAATA

TGGACAGTCCGGTTGGGGTTGCTACTTATTTTTTGCTGTTATGAATTATTTATACATTCCAGTTATCTTCTTTTT
ACCTGTCAGGCCAAC         TAAAAAACGACAATACTTAA                      TAGAAGAAAAA

CTACCCTGAAACCGCCGGAAGAAGTTTGGAGGAAATCGACATCATCTTTGCTAAAGCATACGAGGATGGCACTCA
GATGGGACT             ACCTCCTTTAGCTGTAGTAG         TTCGTATGCTCCTACCGTGA

ACCATGGAGAGTTGCTAACCATTTGCCCAAGTTATCCCTACAAGAAGTCGAAGATCATGCCAATGCATTGGGCTC
              TGGTAAACGGGTTCAATAGG                              ACGTAACCCGAG

TTATGACGACGAAATGGAAAAAGAGGACTTTGGTGAAGATAGAGTAGAAGACACCTATAACCAAATTAACGGCGA
AATACTGC      TACCTTTTTCTCCTGAAACC     TCTCATCTTCTGTGGATATT           TTGCCGCT

TAATTCGTCTAGTTCTTCAAACATCAAAAATGAAGATACAGTGAACGATAAAGCAAATTTTGAGGGTTGA
ATTAAGCAGATC              TTTACTTCTATGTCACTTGC
```

FIG. 11J (Cont.)

SEQUENCE LISTING

```
<160> NUMBER OF SEQ ID NOS: 487

<210> SEQ ID NO 1
<211> LENGTH: 1128
<212> TYPE: DNA
<213> ORGANISM: Artificial Sequence
<220> FEATURE:
<223> OTHER INFORMATION: Probe for Beta-actin

<400> SEQUENCE: 1
atggatgacg atatcgctgc gctcgtcgtc gacaacggct ccggcatgtg caaggccggc      60
ttcgcgggcg acgatgctcc ccgggccgtc ttcccctcca tcgtgggccg ccctaggcac     120
cagggtgtga tggtgggtat gggtcagaag gactcctacg tgggcgacga ggcccagagc     180
aagagaggca tcctgaccct gaagtacccc attgaacacg gcattgtcac caactgggac     240
gatatggaga agatttggca ccacactttc tacaatgagc tgcgtgtggc ccctgaggag     300 cacctgtgc tgctcaccga ggcccctctg aaccctaagg ccaaccgtga aaagatgacc      360
cagatcatgt ttgagacctt caacacccca gccatgtacg tagccatcca ggctgtgttg     420
tccctgtatg cctctggtcg taccactggc attgtgatga ctccggaga cggggtcacc      480 cacactgtgc ccatctatga gggttacgcg ctccctcatg ccatcctgcg tctggacctg     540
gctggccggg acctgacaga ctacctcatg aagatcctga ccgagcgtgg ctacagcttc     600
accaccacag ctgagaggga aatcgtgcgt gacattaaag agaagctgtg ctatgttgcc     660
ctagacttcg agcaagagat ggccactgcc gcatcctctt cctccctgga gaagagctat     720
gagctgcctg acggtcaggt catcactatc ggcaatgagc ggttccgatg ccccgaggct     780
ctcttccagc cttccttcct gggtatggaa tcctgtggca tccatgaaac tacattcaat     840
tccatcatga agtgtgacgt tgacatccgt aaagacctct atgccaacac agtgctgtct     900
```

```
ggtggcacca ccatgtaccc aggcattgct gacaggatgc agaaggagat tactgccctg    960
gctcctagca ccatgaagat caagatcatt gctcctcctg agcgcaagta ctctgtgtgg   1020
attggtggct ctatcctggc ctcactgtcc accttccagc agatgtggat cagcaagcag   1080
gagtacgatg agtccggccc ctccatcgtg caccgcaaat gcttctag                1128
```

<210> SEQ ID NO 2
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 2
atgccggagc cgttgtcgac                                                  20

<210> SEQ ID NO 3
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 3
cgcccgcgaa gccggccttg                                                  20

<210> SEQ ID NO 4
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 4
gaagacggcc cggggagcat                                                  20

<210> SEQ ID NO 5
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 5
ctagggcggc ccacgatgga                                                  20

<210> SEQ ID NO 6
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 6
tacccaccat cacaccctgg                                                  20

<210> SEQ ID NO 7
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 7

```
tacccaccat cacaccctgg                                              20

<210> SEQ ID NO 8
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 8
cacgtaggag tccttctgac                                              20

<210> SEQ ID NO 9
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 9
ggtacttcag ggtcaggatg                                              20

<210> SEQ ID NO 10
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 10
ggtgacaatg ccgtgttcaa                                              20

<210> SEQ ID NO 11
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 11
atcttctcca tatcgtccca                                              20

<210> SEQ ID NO 12
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 12
cattgtagaa agtgtggtgc                                              20

<210> SEQ ID NO 13
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 13
ctcctcaggg gccacacgca                                              20

<210> SEQ ID NO 14
<211> LENGTH: 20
<212> TYPE: DNA
<213> ORGANISM: Artificial Sequence
```

-continued

```
<220> FEATURE:
<223> OTHER INFORMATION: Probe for Beta-actin

<400> SEQUENCE: 14
gcctcggtga gcagcacagg                                               20

<210> SEQ ID NO 15
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 15
ggttggcctt agggttcaga                                               20

<210> SEQ ID NO 16
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 16
catgatctgg gtcatctttt                                               20

<210> SEQ ID NO 17
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 17
gctggggtgt tgaaggtctc                                               20

<210> SEQ ID NO 18
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 18
cagcctggat ggctacgtac                                               20

<210> SEQ ID NO 19
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 19
accagaggca tacagggaca                                               20

<210> SEQ ID NO 20
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 20
tccatcacaa tgccagtggt                                               20
```

```
<210> SEQ ID NO 21
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 21
tgtgggtgac cccgtctccg                                                   20

<210> SEQ ID NO 22
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 22
gtaaccctca tagatgggca                                                   20

<210> SEQ ID NO 23
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 23
cgcaggatgg catgagggag                                                   20

<210> SEQ ID NO 24
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 24
ggtcccggcc agccaggtcc                                                   20

<210> SEQ ID NO 25
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 25
gatcttcatg aggtagtctg                                                   20

<210> SEQ ID NO 26
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 26
aagctgtagc cacgctcggt                                                   20

<210> SEQ ID NO 27
<211> LENGTH: 20
<212> TYPE: DNA
<213> ORGANISM: Artificial Sequence
<220> FEATURE:
<223> OTHER INFORMATION: Probe for Beta-actin
```

```
<400> SEQUENCE: 27
tttccctctc agctgtggtg                                               20

<210> SEQ ID NO 28
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 28
cttctcttta atgtcacgca                                               20

<210> SEQ ID NO 29
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 29
aagtctaggg caacatagca                                               20

<210> SEQ ID NO 30
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 30
cggcagtggc catctcttgc                                               20

<210> SEQ ID NO 31
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 31
cttctccagg gaggaagagg                                               20

<210> SEQ ID NO 32
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 32
tgaccgtcag gcagctcata                                               20

<210> SEQ ID NO 33
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 33
gctcattgcc gatagtgatg                                               20

<210> SEQ ID NO 34
```

```
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 34
gagagcctcg gggcatcgga                                               20

<210> SEQ ID NO 35
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 35
atacccagga aggaaggctg                                               20

<210> SEQ ID NO 36
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 36
tttcatggat gccacaggat                                               20

<210> SEQ ID NO 37
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 37
cttcatgatg gaattgaatg                                               20

<210> SEQ ID NO 38
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 38
tctttacgga tgtcaacgtc                                               20

<210> SEQ ID NO 39
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 39
acagcactgt gttggcatag                                               20

<210> SEQ ID NO 40
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 40
```
tgggtacatg gtggtgccac                                        20

<210> SEQ ID NO 41
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 41
ttctgcatcc tgtcagcaat                                        20

<210> SEQ ID NO 42
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 42
taggagccag ggcagtaatc                                        20

<210> SEQ ID NO 43
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 43
aatgatcttg atcttcatgg                                        20

<210> SEQ ID NO 44
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 44
gagtacttgc gctcaggagg                                        20

<210> SEQ ID NO 45
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 45
ggatagagcc accaatccac                                        20

<210> SEQ ID NO 46
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 46
ctggaaggtg gacagtgagg                                        20

<210> SEQ ID NO 47
<211> LENGTH: 20
<212> TYPE: DNA

```
<213> ORGANISM: Artificial Sequence
<220> FEATURE:
<223> OTHER INFORMATION: Probe for Beta-actin

<400> SEQUENCE: 47
tcctgcttgc tgatccacat                                                    20

<210> SEQ ID NO 48
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 48
tggaggggcc ggactcatcg                                                    20

<210> SEQ ID NO 49
<211> LENGTH: 20
<212> TYPE: DNA
<213> ORGANISM: Artificial Sequence
<220> FEATURE:
<223> OTHER INFORMATION: Probe for Beta-actin

<400> SEQUENCE: 49
ctagaagcat ttgcggtgca                                                    20

<210> SEQ ID NO 50
<211> LENGTH: 1815
<212> TYPE: DNA
<213> ORGANISM: Artificial Sequence
<220> FEATURE:
<223> OTHER INFORMATION: Probe of COX-2

<400> SEQUENCE: 50
atgctcgccc gcgccctgct gctgtgcgcg gtcctggcgc tcagccatac agcaaatcct        60
tgctgttccc acccatgtca aaaccgaggt gtatgtatga gtgtgggatt tgaccagtat       120
aagtgcgatt gtacccggac aggattctat ggagaaaact gctcaacacc ggaattttg        180
acaagaataa aattatttct gaaacccact ccaaacacag tgcactacat acttacccac       240
ttcaagggat tttggaacgt tgtgaataac attcccttcc ttcgaaatgc aattatgagt       300
tatgtgttga catccagatc acatttgatt gacagtccac caacttacaa tgctgactat       360
ggctacaaaa gctgggaagc cttctctaac ctctcctatt atactagagc ccttcctcct       420
gtgcctgatg attgcccgac tcccttgggt gtcaaaggta aaagcagct tcctgattca        480
aatgagattg tggaaaaatt gcttctaaga agaaagttca tccctgatcc ccagggctca       540
aacatgatgt ttgcattctt tgcccagcac ttcacgcatc agttttttca gacagatcat       600
aagcgagggc cagctttcac caacgggctg gccatgggg tggacttaaa tcatatttac        660
ggtgaaactc tggctagaca gcgtaaactg cgccttttca aggatggaaa aatgaaatat       720
cagataattg atggagagat gtatcctccc acagtcaaag atactcaggc agagatgatc       780
taccctcctc aagtccctga gcatctacgg tttgctgtgg ggcaggaggt ctttggtctg       840
gtgcctggtc tgatgatgta tgccacaatc tggctgcggg aacacaacag agtatgcgat       900
gtgcttaaac aggagcatcc tgaatggggt gatgagcagt tgttccagac aagcaggcta       960
atactgatag gagagactat taagattgtg attgaagatt atgtgcaaca cttgagtggc      1020
tatcacttca aactgaaatt tgacccagaa ctacttttca caaacaatt ccagtaccaa       1080
aatcgtattg ctgctgaatt taacacctc tatcactggc atcccctct gcctgacacc       1140
```

```
tttcaaattc atgaccagaa atacaactat caacagttta tctacaacaa ctctatattg    1200
ctggaacatg gaattaccca gtttgttgaa tcattcacca ggcaaattgc tggcagggtt    1260
gctggtggta ggaatgttcc acccgcagta cagaaagtat cacaggcttc cattgaccag    1320
agcaggcaga tgaaatacca gtcttttaat gagtaccgca aacgctttat gctgaagccc    1380
tatgaatcat ttgaagaact tacaggagaa aaggaaatgt ctgcagagtt ggaagcactc    1440
tatggtgaca tcgatgctgt ggagctgtat cctgcccttc tggtagaaaa gcctcggcca    1500
gatgccatct ttggtgaaac catggtagaa gttggagcac cattctcctt gaaaggactt    1560
atgggtaatg ttatatgttc tcctgcctac tggaagccaa gcactttggg tgagaagtg     1620 ggttttcaaa tcatcaacac tgcctcaatt cagtctctca tctgcaataa cgtgaagggc    1680
tgtcccttta cttcattcag tgttccagat ccagagctca ttaaaacagt caccatcaat    1740
gcaagttctt cccgctccgg actagatgat atcaatccca cagtactact aaaagaacgt    1800
tcgactgaac tgtag                                                      1815

<210> SEQ ID NO 51
<211> LENGTH: 20
<212> TYPE: DNA
<213> ORGANISM: Artificial Sequence
<220> FEATURE:
<223> OTHER INFORMATION: Probe of COX-2

<400> SEQUENCE: 51
gcagcagggc gcgggcgagc                                                   20

<210> SEQ ID NO 52
<211> LENGTH: 40
<212> TYPE: DNA
<213> ORGANISM: Artificial Sequence
<220> FEATURE:
<223> OTHER INFORMATION: Probe of COX-2

<400> SEQUENCE: 52
cgcaggatgg catgagggac gcaggatggc atgagggagg                              40

<210> SEQ ID NO 53
<211> LENGTH: 20
<212> TYPE: DNA
<213> ORGANISM: Artificial Sequence
<220> FEATURE:
<223> OTHER INFORMATION: Probe of COX-2

<400> SEQUENCE: 53
ctcatacata cacctcggtt                                                   20

<210> SEQ ID NO 54
<211> LENGTH: 20
<212> TYPE: DNA
<213> ORGANISM: Artificial Sequence
<220> FEATURE:
<223> OTHER INFORMATION: Probe of COX-2

<400> SEQUENCE: 54
atcgcactta tactggtcaa                                                   20

<210> SEQ ID NO 55
<211> LENGTH: 20
<212> TYPE: DNA
<213> ORGANISM: Artificial Sequence
<220> FEATURE:
```

<223> OTHER INFORMATION: Probe of COX-2

<400> SEQUENCE: 55
gtgttgagca gttttctcca                                              20

<210> SEQ ID NO 56
<211> LENGTH: 20
<212> TYPE: DNA
<213> ORGANISM: Artificial Sequence
<220> FEATURE:
<223> OTHER INFORMATION: Probe of COX-2

<400> SEQUENCE: 56
gtttggagtg ggtttcagaa                                              20

<210> SEQ ID NO 57
<211> LENGTH: 20
<212> TYPE: DNA
<213> ORGANISM: Artificial Sequence
<220> FEATURE:
<223> OTHER INFORMATION: Probe of COX-2

<400> SEQUENCE: 57
atcccttgaa gtgggtaagt                                              20

<210> SEQ ID NO 58
<211> LENGTH: 20
<212> TYPE: DNA
<213> ORGANISM: Artificial Sequence
<220> FEATURE:
<223> OTHER INFORMATION: Probe of COX-2

<400> SEQUENCE: 58
ttgcatttcg aaggaaggga                                              20

<210> SEQ ID NO 59
<211> LENGTH: 20
<212> TYPE: DNA
<213> ORGANISM: Artificial Sequence
<220> FEATURE:
<223> OTHER INFORMATION: Probe of COX-2

<400> SEQUENCE: 59
gtgatctgga tgtcaacaca                                              20

<210> SEQ ID NO 60
<211> LENGTH: 20
<212> TYPE: DNA
<213> ORGANISM: Artificial Sequence
<220> FEATURE:
<223> OTHER INFORMATION: Probe of COX-2

<400> SEQUENCE: 60
tgtaagttgg tggactgtca                                              20

<210> SEQ ID NO 61
<211> LENGTH: 20
<212> TYPE: DNA
<213> ORGANISM: Artificial Sequence
<220> FEATURE:
<223> OTHER INFORMATION: Probe of COX-2

<400> SEQUENCE: 61
cttcccagct tttgtagcca                                              20

-continued

```
<210> SEQ ID NO 62
<211> LENGTH: 20
<212> TYPE: DNA
<213> ORGANISM: Artificial Sequence
<220> FEATURE:
<223> OTHER INFORMATION: Probe of COX-2

<400> SEQUENCE: 62
gaggaagggc tctagtataa                                         20

<210> SEQ ID NO 63
<211> LENGTH: 20
<212> TYPE: DNA
<213> ORGANISM: Artificial Sequence
<220> FEATURE:
<223> OTHER INFORMATION: Probe of COX-2

<400> SEQUENCE: 63
caggaagctg cttttacct                                          20

<210> SEQ ID NO 64
<211> LENGTH: 20
<212> TYPE: DNA
<213> ORGANISM: Artificial Sequence
<220> FEATURE:
<223> OTHER INFORMATION: Probe of COX-2

<400> SEQUENCE: 64 gcaattttc cacaatctca                                          20

<210> SEQ ID NO 65
<211> LENGTH: 20
<212> TYPE: DNA
<213> ORGANISM: Artificial Sequence
<220> FEATURE:
<223> OTHER INFORMATION: Probe of COX-2

<400> SEQUENCE: 65
tcagggatga actttcttct                                         20

<210> SEQ ID NO 66
<211> LENGTH: 20
<212> TYPE: DNA
<213> ORGANISM: Artificial Sequence
<220> FEATURE:
<223> OTHER INFORMATION: Probe of COX-2

<400> SEQUENCE: 66
agtgctgggc aaagaatgca                                         20

<210> SEQ ID NO 67
<211> LENGTH: 20
<212> TYPE: DNA
<213> ORGANISM: Artificial Sequence
<220> FEATURE:
<223> OTHER INFORMATION: Probe of COX-2

<400> SEQUENCE: 67
cgcttatgat ctgtcttgaa                                         20

<210> SEQ ID NO 68
<211> LENGTH: 20
<212> TYPE: DNA
<213> ORGANISM: Artificial Sequence
<220> FEATURE:
<223> OTHER INFORMATION: Probe of COX-2
```

```
<400> SEQUENCE: 68
atggcccagc ccgttggtga                                           20

<210> SEQ ID NO 69
<211> LENGTH: 20
<212> TYPE: DNA
<213> ORGANISM: Artificial Sequence
<220> FEATURE:
<223> OTHER INFORMATION: Probe of COX-2

<400> SEQUENCE: 69
gccagagttt caccgtaaat                                           20

<210> SEQ ID NO 70
<211> LENGTH: 20
<212> TYPE: DNA
<213> ORGANISM: Artificial Sequence
<220> FEATURE:
<223> OTHER INFORMATION: Probe of COX-2

<400> SEQUENCE: 70
atccttgaaa aggcgcagtt                                           20

<210> SEQ ID NO 71
<211> LENGTH: 20
<212> TYPE: DNA
<213> ORGANISM: Artificial Sequence
<220> FEATURE:
<223> OTHER INFORMATION: Probe for COX-2

<400> SEQUENCE: 71
gaggatacat ctctccatca                                           20

<210> SEQ ID NO 72
<211> LENGTH: 20
<212> TYPE: DNA
<213> ORGANISM: Artificial Sequence
<220> FEATURE:
<223> OTHER INFORMATION: Probe for COX-2

<400> SEQUENCE: 72
tcatctctgc ctgagtatct                                           20

<210> SEQ ID NO 73
<211> LENGTH: 20
<212> TYPE: DNA
<213> ORGANISM: Artificial Sequence
<220> FEATURE:
<223> OTHER INFORMATION: Probe for COX-2

<400> SEQUENCE: 73
tcagaccagg caccagacca                                           20

<210> SEQ ID NO 74
<211> LENGTH: 20
<212> TYPE: DNA
<213> ORGANISM: Artificial Sequence
<220> FEATURE:
<223> OTHER INFORMATION: Probe for COX-2

<400> SEQUENCE: 74
gttgtgttcc cgcagccaga                                           20

<210> SEQ ID NO 75
<211> LENGTH: 20
```

<212> TYPE: DNA
<213> ORGANISM: Artificial Sequence
<220> FEATURE:
<223> OTHER INFORMATION: Probe for COX-2

<400> SEQUENCE: 75
tcctgtttaa gcacatcgca                                                  20

<210> SEQ ID NO 76
<211> LENGTH: 20
<212> TYPE: DNA
<213> ORGANISM: Artificial Sequence
<220> FEATURE:
<223> OTHER INFORMATION: Probe for COX-2

<400> SEQUENCE: 76
aacaactgct catcacccca                                                  20

<210> SEQ ID NO 77
<211> LENGTH: 20
<212> TYPE: DNA
<213> ORGANISM: Artificial Sequence
<220> FEATURE:
<223> OTHER INFORMATION: Probe for COX-2

<400> SEQUENCE: 77
atagtctctc ctatcagtat                                                  20

<210> SEQ ID NO 78
<211> LENGTH: 20
<212> TYPE: DNA
<213> ORGANISM: Artificial Sequence
<220> FEATURE:
<223> OTHER INFORMATION: Probe for COX-2

<400> SEQUENCE: 78
ccactcaagt gttgcacata                                                  20

<210> SEQ ID NO 79
<211> LENGTH: 20
<212> TYPE: DNA
<213> ORGANISM: Artificial Sequence
<220> FEATURE:
<223> OTHER INFORMATION: Probe for COX-2

<400> SEQUENCE: 79
gttctgggtc aaatttcagt                                                  20

<210> SEQ ID NO 80
<211> LENGTH: 20
<212> TYPE: DNA
<213> ORGANISM: Artificial Sequence
<220> FEATURE:
<223> OTHER INFORMATION: Probe for COX-2

<400> SEQUENCE: 80
gtactggaat tgtttgttga                                                  20

<210> SEQ ID NO 81
<211> LENGTH: 20
<212> TYPE: DNA
<213> ORGANISM: Artificial Sequence
<220> FEATURE:
<223> OTHER INFORMATION: Probe for COX-2

<400> SEQUENCE: 81
gggtgttaaa ttcagcagca                                          20

<210> SEQ ID NO 82
<211> LENGTH: 20
<212> TYPE: DNA
<213> ORGANISM: Artificial Sequence
<220> FEATURE:
<223> OTHER INFORMATION: Probe for COX-2

<400> SEQUENCE: 82
gttgtatttc tggtcatgaa                                          20

<210> SEQ ID NO 83
<211> LENGTH: 20
<212> TYPE: DNA
<213> ORGANISM: Artificial Sequence
<220> FEATURE:
<223> OTHER INFORMATION: Probe for COX-2

<400> SEQUENCE: 83
ggtaattcca tgttccagca                                          20

<210> SEQ ID NO 84
<211> LENGTH: 20
<212> TYPE: DNA
<213> ORGANISM: Artificial Sequence
<220> FEATURE:
<223> OTHER INFORMATION: Probe for COX-2

<400> SEQUENCE: 84
gcctggtgaa tgattcaaca                                          20

<210> SEQ ID NO 85
<211> LENGTH: 20
<212> TYPE: DNA
<213> ORGANISM: Artificial Sequence
<220> FEATURE:
<223> OTHER INFORMATION: Probe for COX-2

<400> SEQUENCE: 85
caatggaagc ctgtgatact                                          20

<210> SEQ ID NO 86
<211> LENGTH: 20
<212> TYPE: DNA
<213> ORGANISM: Artificial Sequence
<220> FEATURE:
<223> OTHER INFORMATION: Probe for COX-2

<400> SEQUENCE: 86
gcgtttgcgg tactcattaa                                          20

<210> SEQ ID NO 87
<211> LENGTH: 20
<212> TYPE: DNA
<213> ORGANISM: Artificial Sequence
<220> FEATURE:
<223> OTHER INFORMATION: Probe for COX-2

<400> SEQUENCE: 87
cctgtaagtt cttcaaatga                                          20

<210> SEQ ID NO 88
<211> LENGTH: 20
<212> TYPE: DNA
<213> ORGANISM: Artificial Sequence

```
<220> FEATURE:
<223> OTHER INFORMATION: Probe for COX-2

<400> SEQUENCE: 88
caactctgca gacatttcct                                                    20

<210> SEQ ID NO 89
<211> LENGTH: 20
<212> TYPE: DNA
<213> ORGANISM: Artificial Sequence
<220> FEATURE:
<223> OTHER INFORMATION: Probe for COX-2

<400> SEQUENCE: 89
ccacagcatc gatgtcacca                                                    20

<210> SEQ ID NO 90
<211> LENGTH: 20
<212> TYPE: DNA
<213> ORGANISM: Artificial Sequence
<220> FEATURE:
<223> OTHER INFORMATION: Probe for COX-2

<400> SEQUENCE: 90
tttctaccag aagggcagga                                                    20

<210> SEQ ID NO 91
<211> LENGTH: 20
<212> TYPE: DNA
<213> ORGANISM: Artificial Sequence
<220> FEATURE:
<223> OTHER INFORMATION: Probe for COX-2

<400> SEQUENCE: 91
cttctaccat ggtttcacca                                                    20

<210> SEQ ID NO 92
<211> LENGTH: 20
<212> TYPE: DNA
<213> ORGANISM: Artificial Sequence
<220> FEATURE:
<223> OTHER INFORMATION: Probe for COX-2

<400> SEQUENCE: 92
cataagtcct ttcaaggaga                                                    20

<210> SEQ ID NO 93
<211> LENGTH: 20
<212> TYPE: DNA
<213> ORGANISM: Artificial Sequence
<220> FEATURE:
<223> OTHER INFORMATION: Probe for COX-2

<400> SEQUENCE: 93
cagtaggcag gagaacatat                                                    20

<210> SEQ ID NO 94
<211> LENGTH: 20
<212> TYPE: DNA
<213> ORGANISM: Artificial Sequence
<220> FEATURE:
<223> OTHER INFORMATION: Probe for COX-2

<400> SEQUENCE: 94 aaacccact tctccaccaa                                                     20
```

-continued

```
<210> SEQ ID NO 95
<211> LENGTH: 20
<212> TYPE: DNA
<213> ORGANISM: Artificial Sequence
<220> FEATURE:
<223> OTHER INFORMATION: Probe for COX-2

<400> SEQUENCE: 95
attgcagatg agagactgaa                                                   20

<210> SEQ ID NO 96
<211> LENGTH: 20
<212> TYPE: DNA
<213> ORGANISM: Artificial Sequence
<220> FEATURE:
<223> OTHER INFORMATION: Probe for COX-2

<400> SEQUENCE: 96
ctggaacact gaatgaagta                                                   20

<210> SEQ ID NO 97
<211> LENGTH: 20
<212> TYPE: DNA
<213> ORGANISM: Artificial Sequence
<220> FEATURE:
<223> OTHER INFORMATION: Probe for COX-2

<400> SEQUENCE: 97
cttgcattga tggtgactgt                                                   20

<210> SEQ ID NO 98
<211> LENGTH: 20
<212> TYPE: DNA
<213> ORGANISM: Artificial Sequence
<220> FEATURE:
<223> OTHER INFORMATION: Probe for COX-2

<400> SEQUENCE: 98
cagttcagtc gaacgttctt                                                   20

<210> SEQ ID NO 99
<211> LENGTH: 958
<212> TYPE: DNA
<213> ORGANISM: Artificial Sequence
<220> FEATURE:
<223> OTHER INFORMATION: Probe for d2EGFP

<400> SEQUENCE: 99
gcggatggtg agcaagggcg aggagctgtt caccggggtg gtgcccatcc tggtcgagct        60
ggacggcgac gtaaacggcc acaagttcag cgtgtccggc gagggcgagg gcgatgccac       120
ctacggcaag ctgaccctga agttcatctg caccaccggc aagctgcccg tgccctggcc       180
caccctcgtg accaccctga cctacggcgt gcagtgcttc agccgctacc ccgaccacat       240
gaagcagcac gacttcttca gtccgccat gcccgaaggc tacgtccagg agcgcaccat        300
cttcttcaag gacgacggca actacaagac ccgcgccgag gtgaagttcg agggcgacac       360
cctggtgaac cgcatcgagc tgaagggcat cgacttcaag gaggacggca acatcctggg       420
gcacaagctg gagtacaact acaacagcca caacgtctat atcatggccg acaagcagaa       480
gaacggcatc aaggtgaact tcaagatccg ccacaacatc gaggacggca gcgtgcagct       540
cgccgaccac taccagcaga acaccccat cggcgacggc ccgtgctgc tgcccgacaa        600 ccactacctg agcacccagt ccgccctgag caaagacccc aacgagaagc gcgatcacat       660
```

```
ggtcctgctg gagttcgtga ccgccgccgg gatcactctc ggcatggacg agctgtacaa    720
gaagcttagc catggcttcc cgccggaggt ggaggagcag gatgatggca cgctgcccat    780
gtcttgtgcc caggagagcg ggatggaccg tcaccctgca gcctgtgctt ctgctaggat    840
caatgtgtag gaattcgtga catgataaga tacattgatg agtttggaca aaccacaact    900
agaatgcagt gaaaaaaatg ctttatttgt gaaatttgtg atgctattgc tttatttg     958
```

<210> SEQ ID NO 100
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 100
cgcccttgct caccatc                                                   17

<210> SEQ ID NO 101
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 101
caccccggtg aacagct                                                   17

<210> SEQ ID NO 102
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 102
agctcgacca ggatggg                                                   17

<210> SEQ ID NO 103
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 103
ggccgtttac gtcgccg                                                   17

<210> SEQ ID NO 104
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 104
gccggacacg ctgaact                                                   17

<210> SEQ ID NO 105
<211> LENGTH: 17
<212> TYPE: DNA
<213> ORGANISM: Artificial Sequence
<220> FEATURE:
<223> OTHER INFORMATION: Probe of d2EGFP -continued

```
<400> SEQUENCE: 105
gtggcatcgc cctcgcc                                                17

<210> SEQ ID NO 106
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 106
tcagggtcag cttgccg                                                17

<210> SEQ ID NO 107
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 107
gccggtggtg cagatga                                                17

<210> SEQ ID NO 108
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 108
ggccagggca cgggcag                                                17

<210> SEQ ID NO 109
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 109
tcagggtggt cacgagg                                                17

<210> SEQ ID NO 110
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 110
gaagcactgc acgccgt                                                17

<210> SEQ ID NO 111
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 111
atgtggtcgg ggtagcg                                                17

<210> SEQ ID NO 112
<211> LENGTH: 17
```

```
<212> TYPE: DNA
<213> ORGANISM: Artificial Sequence
<220> FEATURE:
<223> OTHER INFORMATION: Probe of d2EGFP

<400> SEQUENCE: 112
tgaagaagtc gtgctgc                                                    17

<210> SEQ ID NO 113
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 113
gccttcgggc atggcgg                                                    17

<210> SEQ ID NO 114
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 114
atggtgcgct cctggac                                                    17

<210> SEQ ID NO 115
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 115
tgccgtcgtc cttgaag                                                    17

<210> SEQ ID NO 116
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 116
ctcggcgcgg gtcttgt                                                    17

<210> SEQ ID NO 117
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 117
gtgtcgccct cgaactt                                                    17

<210> SEQ ID NO 118
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 118
```
gctcgatgcg gttcacc                                                    17

<210> SEQ ID NO 119
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 119
cttgaagtcg atgccct                                                    17

<210> SEQ ID NO 120
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 120
cccaggatgt tgccgtc                                                    17

<210> SEQ ID NO 121
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 121
agttgtactc cagcttg                                                    17

<210> SEQ ID NO 122
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 122
atagacgttg tggctgt                                                    17

<210> SEQ ID NO 123
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 123
ttctgcttgt cggccat                                                    17

<210> SEQ ID NO 124
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 124
agttcacctt gatgccg                                                    17

<210> SEQ ID NO 125
<211> LENGTH: 17
<212> TYPE: DNA
<213> ORGANISM: Artificial Sequence

```
<220> FEATURE:
<223> OTHER INFORMATION: Probe of d2EGFP

<400> SEQUENCE: 125
gatgttgtgg cggatct                                                      17

<210> SEQ ID NO 126
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 126
agctgcacgc tgccgtc                                                      17

<210> SEQ ID NO 127
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 127
tctgctggta gtggtcg                                                      17

<210> SEQ ID NO 128
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 128
gccgtcgccg atggggg                                                      17

<210> SEQ ID NO 129
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 129
ttgtcgggca gcagcac                                                      17

<210> SEQ ID NO 130
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 130
actgggtgct caggtag                                                      17

<210> SEQ ID NO 131
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 131
ggggtctttg ctcaggg                                                      17
```

<210> SEQ ID NO 132
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 132
atgtgatcgc gcttctc                                                17

<210> SEQ ID NO 133
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 133
tcacgaactc cagcagg                                                17

<210> SEQ ID NO 134
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 134
gagagtgatc ccggcgg                                                17

<210> SEQ ID NO 135
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 135
ttgtacagct cgtccat                                                17

<210> SEQ ID NO 136
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 136
ggaagccatg gctaagc                                                17

<210> SEQ ID NO 137
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 137
ctgctcctcc acctccg                                                17

<210> SEQ ID NO 138
<211> LENGTH: 17
<212> TYPE: DNA
<213> ORGANISM: Artificial Sequence
<220> FEATURE:
<223> OTHER INFORMATION: Probe of d2EGFP

```
<400> SEQUENCE: 138
atgggcagcg tgccatc                                              17

<210> SEQ ID NO 139
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 139
cgctctcctg ggcacaa                                              17

<210> SEQ ID NO 140
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 140
tgcagggtga cggtcca                                              17

<210> SEQ ID NO 141
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 141
atcctagcag aagcaca                                              17

<210> SEQ ID NO 142
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 142
acgaattcct acacatt                                              17

<210> SEQ ID NO 143
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 143
tcaatgtatc ttatcat                                              17

<210> SEQ ID NO 144
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 144
ttgtggtttg tccaaac                                              17

<210> SEQ ID NO 145
```

```
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 145
tttttttcac tgcattc                                                    17

<210> SEQ ID NO 146
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 146
caaatttcac aaataaa                                                    17

<210> SEQ ID NO 147
<211> LENGTH: 17
<212> TYPE: DNA
<213> ORGANISM: Artificial Sequence
<220> FEATURE:
<223> OTHER INFORMATION: Probe of d2EGFP

<400> SEQUENCE: 147
caaataaagc aatagca                                                    17

<210> SEQ ID NO 148
<211> LENGTH: 1767
<212> TYPE: DNA
<213> ORGANISM: Artificial Sequence
<220> FEATURE:
<223> OTHER INFORMATION: Probe for dpp

<400> SEQUENCE: 148
atgcgcgcat ggcttctact cctcgcagtg ctggcgactt ttcaaacgat tgttcgagtt      60
gctagcaccg aggatatatc ccagagattc atcgccgcca tagcgcccgt tgccgctcat     120
attccgctgg catcagcatc aggatcagga tcaggacgat ctggatctag atcggtagga     180
gcctcgacca gcacagcatt agcaaaagca tttaatccat tcagcgagcc cgcctcgttc     240
agtgatagtg ataaaagcca tcggagtaaa acaaacaaaa aacctagcaa aagtgacgcg     300
aaccgacagt tcaacgaagt gcataagcca agaacagacc aattagaaaa ttccaaaaat     360
aagtctaaac aattagttaa taaacccaac cacaacaaaa tggctgtcaa ggagcagagg     420
agccaccaca agaagagcca ccaccatcgc agccaccagc caaagcaggc cagtgcatcc     480
acagaatctc atcaatcctc gtcgattgaa tcaatcttcg tggaggagcc gacgctggtg     540
ctcgaccgcg aggtggcctc catcaacgtg cccgccaacg ccaaggccat catcgccgag     600
cagggccccgt ccacctacag caaggaggcg ctcatcaagg acaagctgaa gccagaccccc     660
tccactctag tcgagatcga aagagcctg ctctcgctgt tcaacatgaa gcggccgccc     720
aagatcgacc gctccaagat catcatcccc gagccgatga agaagctcta cgccgagatc     780
atgggccacg agctcgactc ggtcaacatc cccaagccgg tctgctgac caagtcggcc     840
aacacagtgc gaagttttac acacaaagat agtaaaatcg acgatcgatt tccgcaccac     900
caccggtttc ggctgcactt cgacgtgaag agcattcccg ccgacgagaa gctgaaggcg     960
gcggagctgc agctgacccg ggacgcactc agtcaacagg tggtggccag cagatcgtcg    1020
gcgaatcgga cgcgctacca ggtgcttgtc tacgacatca cgcgcgtcgg ggtgcgtggt    1080
```

```
cagcgggagc cgagctatct gctgttggac accaagacgg tccggcttaa cagcacggac    1140
acggtgagcc tcgatgtcca gccggccgtg gaccggtggc tggcgagtcc gcagcgcaac    1200
tacggactgc tggtggaggt gcggacggtc cgctccctga agccggcccc acaccaccat    1260
gtacgcctgc gccgcagcgc ggacgaggcg cacgagcggt ggcagcacaa gcagccgctc    1320
ctgttcacct acacggacga cgggcggcac aaggcgcgct ccattcggga cgtgtctggc    1380
ggagagggcg gtggcaaggg cggccggaac aagcggcagc cgagacgcc tacgaggcgc     1440 aagaaccacg acgacacctg ccggcggcac tcgctgtacg tggacttctc ggacgtgggc    1500
tgggacgact ggattgtggc gcctctgggc tacgatgcat attactgcca cgggaagtgc    1560
cccttcccgc tggccgacca ctttaactcg accaatcacg ccgtggtgca gaccctggtc    1620
aacaatatga atcccggcaa ggtgccgaag gcgtgctgcg tgcccacgca actggacagc    1680
gtggccatgc tctatctcaa cgaccaaagt acggtggtgc tgaagaacta ccaggagatg    1740
accgtggtgg gctgtggctg tcgatag                                        1767
```

<210> SEQ ID NO 149
<211> LENGTH: 20
<212> TYPE: DNA
<213> ORGANISM: Artificial Sequence
<220> FEATURE:
<223> OTHER INFORMATION: Probe for dpp

<400> SEQUENCE: 149
ggagtagaag ccatgcgcgc                                                20

<210> SEQ ID NO 150
<211> LENGTH: 20
<212> TYPE: DNA
<213> ORGANISM: Artificial Sequence
<220> FEATURE:
<223> OTHER INFORMATION: Probe for dpp

<400> SEQUENCE: 150
gtttgaaaag tcgccagcac                                                20

<210> SEQ ID NO 151
<211> LENGTH: 20
<212> TYPE: DNA
<213> ORGANISM: Artificial Sequence
<220> FEATURE:
<223> OTHER INFORMATION: Probe for dpp

<400> SEQUENCE: 151
cctcggtgct agcaactcga                                                20

<210> SEQ ID NO 152
<211> LENGTH: 20
<212> TYPE: DNA
<213> ORGANISM: Artificial Sequence
<220> FEATURE:
<223> OTHER INFORMATION: Probe for dpp

<400> SEQUENCE: 152
cgggcgctat ggcggcgatg                                                20

<210> SEQ ID NO 153
<211> LENGTH: 19
<212> TYPE: DNA
<213> ORGANISM: Artificial Sequence
<220> FEATURE:

<223> OTHER INFORMATION: Probe for dpp

<400> SEQUENCE: 153
ctgatgctga tgccagcgg                                                    19

<210> SEQ ID NO 154
<211> LENGTH: 20
<212> TYPE: DNA
<213> ORGANISM: Artificial Sequence
<220> FEATURE:
<223> OTHER INFORMATION: Probe for dpp

<400> SEQUENCE: 154
gctggtcgag gctcctaccg                                                   20

<210> SEQ ID NO 155
<211> LENGTH: 20
<212> TYPE: DNA
<213> ORGANISM: Artificial Sequence
<220> FEATURE:
<223> OTHER INFORMATION: Probe for dpp

<400> SEQUENCE: 155
tgaacgaggc gggctcgctg                                                   20

<210> SEQ ID NO 156
<211> LENGTH: 20
<212> TYPE: DNA
<213> ORGANISM: Artificial Sequence
<220> FEATURE:
<223> OTHER INFORMATION: Probe for dpp

<400> SEQUENCE: 156
ctccgatggc ttttatcact                                                   20

<210> SEQ ID NO 157
<211> LENGTH: 20
<212> TYPE: DNA
<213> ORGANISM: Artificial Sequence
<220> FEATURE:
<223> OTHER INFORMATION: Probe for dpp

<400> SEQUENCE: 157
cgttgaactg tcggttcgcg                                                   20

<210> SEQ ID NO 158
<211> LENGTH: 20
<212> TYPE: DNA
<213> ORGANISM: Artificial Sequence
<220> FEATURE:
<223> OTHER INFORMATION: Probe for dpp

<400> SEQUENCE: 158
ggtggctcct ctgctccttg                                                   20

<210> SEQ ID NO 159
<211> LENGTH: 20
<212> TYPE: DNA
<213> ORGANISM: Artificial Sequence
<220> FEATURE:
<223> OTHER INFORMATION: Probe for dpp

<400> SEQUENCE: 159
ggctgcgatg gtggtggctc                                                   20

```
<210> SEQ ID NO 160
<211> LENGTH: 20
<212> TYPE: DNA
<213> ORGANISM: Artificial Sequence
<220> FEATURE:
<223> OTHER INFORMATION: Probe for dpp

<400> SEQUENCE: 160
ctgtggatgc actggcctgc                                              20

<210> SEQ ID NO 161
<211> LENGTH: 20
<212> TYPE: DNA
<213> ORGANISM: Artificial Sequence
<220> FEATURE:
<223> OTHER INFORMATION: Probe for dpp

<400> SEQUENCE: 161
ccagcgtcgg ctcctccacg                                              20

<210> SEQ ID NO 162
<211> LENGTH: 20
<212> TYPE: DNA
<213> ORGANISM: Artificial Sequence
<220> FEATURE:
<223> OTHER INFORMATION: Probe for dpp

<400> SEQUENCE: 162
ccttggcgtt ggcgggcacg                                              20

<210> SEQ ID NO 163
<211> LENGTH: 20
<212> TYPE: DNA
<213> ORGANISM: Artificial Sequence
<220> FEATURE:
<223> OTHER INFORMATION: Probe for dpp

<400> SEQUENCE: 163
ggtggacggg ccctgctcgg                                              20

<210> SEQ ID NO 164
<211> LENGTH: 20
<212> TYPE: DNA
<213> ORGANISM: Artificial Sequence
<220> FEATURE:
<223> OTHER INFORMATION: Probe for dpp

<400> SEQUENCE: 164
ggaggggtct ggcttcagct                                              20

<210> SEQ ID NO 165
<211> LENGTH: 20
<212> TYPE: DNA
<213> ORGANISM: Artificial Sequence
<220> FEATURE:
<223> OTHER INFORMATION: Probe for dpp

<400> SEQUENCE: 165
agcgagagca ggctcttctc                                              20

<210> SEQ ID NO 166
<211> LENGTH: 20
<212> TYPE: DNA
<213> ORGANISM: Artificial Sequence
<220> FEATURE:
<223> OTHER INFORMATION: Probe for dpp
```

```
<400> SEQUENCE: 166
gagcggtcga tcttgggcgg                                         20

<210> SEQ ID NO 167
<211> LENGTH: 20
<212> TYPE: DNA
<213> ORGANISM: Artificial Sequence
<220> FEATURE:
<223> OTHER INFORMATION: Probe for dpp

<400> SEQUENCE: 167
cttcatcggc tcggggatga                                         20

<210> SEQ ID NO 168
<211> LENGTH: 20
<212> TYPE: DNA
<213> ORGANISM: Artificial Sequence
<220> FEATURE:
<223> OTHER INFORMATION: Probe for dpp

<400> SEQUENCE: 168
tcgtggccca tgatctcggc                                         20

<210> SEQ ID NO 169
<211> LENGTH: 20
<212> TYPE: DNA
<213> ORGANISM: Artificial Sequence
<220> FEATURE:
<223> OTHER INFORMATION: Probe for dpp

<400> SEQUENCE: 169
gcagacccgg cttggggatg                                         20

<210> SEQ ID NO 170
<211> LENGTH: 20
<212> TYPE: DNA
<213> ORGANISM: Artificial Sequence
<220> FEATURE:
<223> OTHER INFORMATION: Probe for dpp

<400> SEQUENCE: 170
cgcactgtgt tggccgactt                                         20

<210> SEQ ID NO 171
<211> LENGTH: 20
<212> TYPE: DNA
<213> ORGANISM: Artificial Sequence
<220> FEATURE:
<223> OTHER INFORMATION: Probe for dpp

<400> SEQUENCE: 171
gcagccgaaa ccggtggtgg                                         20

<210> SEQ ID NO 172
<211> LENGTH: 20
<212> TYPE: DNA
<213> ORGANISM: Artificial Sequence
<220> FEATURE:
<223> OTHER INFORMATION: Probe for dpp

<400> SEQUENCE: 172
ccgccgcctt cagcttctcg                                         20

<210> SEQ ID NO 173
<211> LENGTH: 20
```

```
<212> TYPE: DNA
<213> ORGANISM: Artificial Sequence
<220> FEATURE:
<223> OTHER INFORMATION: Probe for dpp

<400> SEQUENCE: 173
agtgcgtccc gggtcagctg                                                   20

<210> SEQ ID NO 174
<211> LENGTH: 20
<212> TYPE: DNA
<213> ORGANISM: Artificial Sequence
<220> FEATURE:
<223> OTHER INFORMATION: Probe for dpp

<400> SEQUENCE: 174
ccgacgatct gctggccacc                                                   20

<210> SEQ ID NO 175
<211> LENGTH: 20
<212> TYPE: DNA
<213> ORGANISM: Artificial Sequence
<220> FEATURE:
<223> OTHER INFORMATION: Probe for dpp

<400> SEQUENCE: 175
agcacctggt agcgcgtccg                                                   20

<210> SEQ ID NO 176
<211> LENGTH: 20
<212> TYPE: DNA
<213> ORGANISM: Artificial Sequence
<220> FEATURE:
<223> OTHER INFORMATION: Probe for dpp

<400> SEQUENCE: 176
cacgcacccc gacgcgcgtg                                                   20

<210> SEQ ID NO 177
<211> LENGTH: 20
<212> TYPE: DNA
<213> ORGANISM: Artificial Sequence
<220> FEATURE:
<223> OTHER INFORMATION: Probe for dpp

<400> SEQUENCE: 177
gccggaccgt cttggtgtcc                                                   20

<210> SEQ ID NO 178
<211> LENGTH: 20
<212> TYPE: DNA
<213> ORGANISM: Artificial Sequence
<220> FEATURE:
<223> OTHER INFORMATION: Probe for dpp

<400> SEQUENCE: 178
gaggctcacc gtgtccgtgc                                                   20

<210> SEQ ID NO 179
<211> LENGTH: 20
<212> TYPE: DNA
<213> ORGANISM: Artificial Sequence
<220> FEATURE:
<223> OTHER INFORMATION: Probe for dpp

<400> SEQUENCE: 179
```
gccagccacc ggtccacggc                                                    20

<210> SEQ ID NO 180
<211> LENGTH: 20
<212> TYPE: DNA
<213> ORGANISM: Artificial Sequence
<220> FEATURE:
<223> OTHER INFORMATION: Probe for dpp

<400> SEQUENCE: 180
cagcagtccg tagttgcgct                                                    20

<210> SEQ ID NO 181
<211> LENGTH: 20
<212> TYPE: DNA
<213> ORGANISM: Artificial Sequence
<220> FEATURE:
<223> OTHER INFORMATION: Probe for dpp

<400> SEQUENCE: 181
gggagcggac cgtccgcacc                                                    20

<210> SEQ ID NO 182
<211> LENGTH: 20
<212> TYPE: DNA
<213> ORGANISM: Artificial Sequence
<220> FEATURE:
<223> OTHER INFORMATION: Probe for dpp

<400> SEQUENCE: 182
caggcgtaca tggtggtgtg                                                    20

<210> SEQ ID NO 183
<211> LENGTH: 20
<212> TYPE: DNA
<213> ORGANISM: Artificial Sequence
<220> FEATURE:
<223> OTHER INFORMATION: Probe for dpp

<400> SEQUENCE: 183
cgtgcgcctc gtccgcgctg                                                    20

<210> SEQ ID NO 184
<211> LENGTH: 20
<212> TYPE: DNA
<213> ORGANISM: Artificial Sequence
<220> FEATURE:
<223> OTHER INFORMATION: Probe for dpp

<400> SEQUENCE: 184
gagcggctgc ttgtgctgcc                                                    20

<210> SEQ ID NO 185
<211> LENGTH: 20
<212> TYPE: DNA
<213> ORGANISM: Artificial Sequence
<220> FEATURE:
<223> OTHER INFORMATION: Probe for dpp

<400> SEQUENCE: 185
ccgcccgtcg tccgtgtagg                                                    20

<210> SEQ ID NO 186
<211> LENGTH: 20
<212> TYPE: DNA
<213> ORGANISM: Artificial Sequence
<220> FEATURE:
<223> OTHER INFORMATION: Probe for dpp

<400> SEQUENCE: 186
gccaccgccc tctccgccag                                            20

<210> SEQ ID NO 187
<211> LENGTH: 20
<212> TYPE: DNA
<213> ORGANISM: Artificial Sequence
<220> FEATURE:
<223> OTHER INFORMATION: Probe for dpp

<400> SEQUENCE: 187
cgtaggccgt ctcggctgcc                                            20

<210> SEQ ID NO 188
<211> LENGTH: 20
<212> TYPE: DNA
<213> ORGANISM: Artificial Sequence
<220> FEATURE:
<223> OTHER INFORMATION: Probe for dpp

<400> SEQUENCE: 188
gcgagtgccg ccggcaggtg                                            20

<210> SEQ ID NO 189
<211> LENGTH: 20
<212> TYPE: DNA
<213> ORGANISM: Artificial Sequence
<220> FEATURE:
<223> OTHER INFORMATION: Probe for dpp

<400> SEQUENCE: 189
cgtcccagcc cacgtccgag                                            20

<210> SEQ ID NO 190
<211> LENGTH: 20
<212> TYPE: DNA
<213> ORGANISM: Artificial Sequence
<220> FEATURE:
<223> OTHER INFORMATION: Probe for dpp

<400> SEQUENCE: 190
cgtagcccag aggcgccaca                                            20

<210> SEQ ID NO 191
<211> LENGTH: 20
<212> TYPE: DNA
<213> ORGANISM: Artificial Sequence
<220> FEATURE:
<223> OTHER INFORMATION: Probe for dpp

<400> SEQUENCE: 191
cggccagcgg gaaggggcac                                            20

<210> SEQ ID NO 192
<211> LENGTH: 20
<212> TYPE: DNA
<213> ORGANISM: Artificial Sequence
<220> FEATURE:
<223> OTHER INFORMATION: Probe for dpp

<400> SEQUENCE: 192
gggtctgcac cacggcgtga                                            20

<210> SEQ ID NO 193
<211> LENGTH: 20
<212> TYPE: DNA
<213> ORGANISM: Artificial Sequence
<220> FEATURE:
<223> OTHER INFORMATION: Probe for dpp

<400> SEQUENCE: 193
gccttcggca ccttgccggg                                            20

<210> SEQ ID NO 194
<211> LENGTH: 20
<212> TYPE: DNA
<213> ORGANISM: Artificial Sequence
<220> FEATURE:
<223> OTHER INFORMATION: Probe for dpp

<400> SEQUENCE: 194
gtccagttgc gtgggcacgc                                            20

<210> SEQ ID NO 195
<211> LENGTH: 20
<212> TYPE: DNA
<213> ORGANISM: Artificial Sequence
<220> FEATURE:
<223> OTHER INFORMATION: Probe for dpp

<400> SEQUENCE: 195
gcaccaccgt actttggtcg                                            20

<210> SEQ ID NO 196
<211> LENGTH: 20
<212> TYPE: DNA
<213> ORGANISM: Artificial Sequence
<220> FEATURE:
<223> OTHER INFORMATION: Probe for dpp

<400> SEQUENCE: 196
gccacagccc accacggtca                                            20

<210> SEQ ID NO 197
<211> LENGTH: 1302
<212> TYPE: DNA
<213> ORGANISM: Artificial Sequence
<220> FEATURE:
<223> OTHER INFORMATION: Probe for elt-2

<400> SEQUENCE: 197
atggataata actacaatga taatgtcaac ggctgggccg aaatggaacc atctcaacca    60
atgggaggtc tgcgcctacc aactcagaac atggatccac cagagcaaaa taatgagtca   120
caattgagtg aactaccgag aatgaaaatt gataatgatt acgcatctcc aattgaacgg   180
caaagtgtta tcacaagtgg cacaaataac tatgagccga agtggaaac tgttacatca    240 tttttccata ctggcataga ctactcaaac tttggaatgt ggaccaaac taccatgcaa    300 ccgttttatc ctctttacag tggaattccc gtaaacactc ttggaacttt ttcgggatat   360
acaaactcca tatcgacaa accctctctg tacgacccca gtattcctac cattaacatc    420
ccttctactt atccaactgt ggctccaact tacgaatgcg tcaaatgctc acaaagttgt   480
ggggccggga tgaaggcagt aaacggagga atgatgtgcg tcaactgttc aacaccaaaa   540
accacgtatt ctcctccagt cgcgtatagc acttctttgg gacaaccccc gattctggaa    600 atacctttcag agcagccaac tgctaaaatt gccaagcaat cctctaaaaa gtcaagtagc    660

-continued

```
tcaaataggg ggtcaaacgg atctgcgtcc cgtcggcagg gacttgtgtg ctccaattgc      720
aatggtacca acacaactct ctggagaaga aatgctgaag gagatccggt ctgcaatgct      780
tgcgggcttt acttcaaact ccatcacatc cctcggccga cctcaatgaa gaaagaaggt      840
gctttacaga caagaaagag aaaatcaaaa agcggagact cttccacacc atcaacgtca      900
cgggcccgag aaaggaagtt tgagagagcc tcttcttcga ccgaaaaggc tcaaaggtca      960
tctaaccggc gtgcgggaag tgcaaaagca gaccgagaac tgagcactgc tgccgtcgca     1020
gctgcgactg ccacatatgt gtcacatgcc gacttgtatc ccgtttcctc agctgccgtc     1080
accttgccag atcaaacgta cagtaattac tatcaatgga acactgccgc tacagctggg     1140
ttgatgatgg ttccaaacga tcaaaactac gtgtatgcag caacaaacta ccagactggc     1200
ctaagacctg ccgataacat ccaagttcat gtgatgccag ttcaggatga tgaaaccaaa     1260
gctgcggctc gcgatttgga agcggtcgac ggagattctt aa                       1302
```

<210> SEQ ID NO 198
<211> LENGTH: 20
<212> TYPE: DNA
<213> ORGANISM: Artificial Sequence
<220> FEATURE:
<223> OTHER INFORMATION: Probe for elt-2

<400> SEQUENCE: 198
ccatttcggc ccagccgttg                                                    20

<210> SEQ ID NO 199
<211> LENGTH: 20
<212> TYPE: DNA
<213> ORGANISM: Artificial Sequence
<220> FEATURE:
<223> OTHER INFORMATION: Probe for elt-2

<400> SEQUENCE: 199
gacctcccat tggttgagat                                                    20

<210> SEQ ID NO 200
<211> LENGTH: 20
<212> TYPE: DNA
<213> ORGANISM: Artificial Sequence
<220> FEATURE:
<223> OTHER INFORMATION: Probe for elt-2

<400> SEQUENCE: 200
ccatgttctg agttggtagg                                                    20

<210> SEQ ID NO 201
<211> LENGTH: 20
<212> TYPE: DNA
<213> ORGANISM: Artificial Sequence
<220> FEATURE:
<223> OTHER INFORMATION: Probe for elt-2

<400> SEQUENCE: 201
actcattatt ttgctctggt                                                    20

<210> SEQ ID NO 202
<211> LENGTH: 20
<212> TYPE: DNA
<213> ORGANISM: Artificial Sequence
<220> FEATURE:
<223> OTHER INFORMATION: Probe for elt-2

```
<400> SEQUENCE: 202
ttctcggtag ttcactcaat                                               20

<210> SEQ ID NO 203
<211> LENGTH: 20
<212> TYPE: DNA
<213> ORGANISM: Artificial Sequence
<220> FEATURE:
<223> OTHER INFORMATION: Probe for elt-2

<400> SEQUENCE: 203
taacactttg ccgttcaatt                                               20

<210> SEQ ID NO 204
<211> LENGTH: 20
<212> TYPE: DNA
<213> ORGANISM: Artificial Sequence
<220> FEATURE:
<223> OTHER INFORMATION: Probe for elt-2

<400> SEQUENCE: 204
catagttatt tgtgccactt                                               20

<210> SEQ ID NO 205
<211> LENGTH: 20
<212> TYPE: DNA
<213> ORGANISM: Artificial Sequence
<220> FEATURE:
<223> OTHER INFORMATION: Probe for elt-2

<400> SEQUENCE: 205
atgtaacagt ttccactttc                                               20

<210> SEQ ID NO 206
<211> LENGTH: 20
<212> TYPE: DNA
<213> ORGANISM: Artificial Sequence
<220> FEATURE:
<223> OTHER INFORMATION: Probe for elt-2

<400> SEQUENCE: 206
agtctatgcc agtatggaaa                                               20

<210> SEQ ID NO 207
<211> LENGTH: 20
<212> TYPE: DNA
<213> ORGANISM: Artificial Sequence
<220> FEATURE:
<223> OTHER INFORMATION: Probe for elt-2

<400> SEQUENCE: 207
ggtccaacat tccaaagttt                                               20

<210> SEQ ID NO 208
<211> LENGTH: 20
<212> TYPE: DNA
<213> ORGANISM: Artificial Sequence
<220> FEATURE:
<223> OTHER INFORMATION: Probe for elt-2

<400> SEQUENCE: 208
gataaaacgg ttgcatggta                                               20

<210> SEQ ID NO 209
<211> LENGTH: 20
```

```
<212> TYPE: DNA
<213> ORGANISM: Artificial Sequence
<220> FEATURE:
<223> OTHER INFORMATION: Probe for elt-2

<400> SEQUENCE: 209
ttacgggaat tccactgtaa                                                    20

<210> SEQ ID NO 210
<211> LENGTH: 20
<212> TYPE: DNA
<213> ORGANISM: Artificial Sequence
<220> FEATURE:
<223> OTHER INFORMATION: Probe for elt-2

<400> SEQUENCE: 210
atcccgaaaa agttccaaga                                                    20

<210> SEQ ID NO 211
<211> LENGTH: 20
<212> TYPE: DNA
<213> ORGANISM: Artificial Sequence
<220> FEATURE:
<223> OTHER INFORMATION: Probe for elt-2

<400> SEQUENCE: 211
gtttgtcgta tatggagttt                                                    20

<210> SEQ ID NO 212
<211> LENGTH: 20
<212> TYPE: DNA
<213> ORGANISM: Artificial Sequence
<220> FEATURE:
<223> OTHER INFORMATION: Probe for elt-2

<400> SEQUENCE: 212
gaatactggg gtcgtacaga                                                    20

<210> SEQ ID NO 213
<211> LENGTH: 20
<212> TYPE: DNA
<213> ORGANISM: Artificial Sequence
<220> FEATURE:
<223> OTHER INFORMATION: Probe for elt-2

<400> SEQUENCE: 213
aagtagaagg gatgttaatg                                                    20

<210> SEQ ID NO 214
<211> LENGTH: 20
<212> TYPE: DNA
<213> ORGANISM: Artificial Sequence
<220> FEATURE:
<223> OTHER INFORMATION: Probe for elt-2

<400> SEQUENCE: 214
cgtaagttgg agccacagtt                                                    20

<210> SEQ ID NO 215
<211> LENGTH: 20
<212> TYPE: DNA
<213> ORGANISM: Artificial Sequence
<220> FEATURE:
<223> OTHER INFORMATION: Probe for elt-2

<400> SEQUENCE: 215
```
aactttgtga gcatttgacg                                          20

<210> SEQ ID NO 216
<211> LENGTH: 20
<212> TYPE: DNA
<213> ORGANISM: Artificial Sequence
<220> FEATURE:
<223> OTHER INFORMATION: Probe for elt-2

<400> SEQUENCE: 216
ttactgcctt catcccggcc                                          20

<210> SEQ ID NO 217
<211> LENGTH: 20
<212> TYPE: DNA
<213> ORGANISM: Artificial Sequence
<220> FEATURE:
<223> OTHER INFORMATION: Probe for elt-2

<400> SEQUENCE: 217
agttgacgca catcattcct                                          20

<210> SEQ ID NO 218
<211> LENGTH: 20
<212> TYPE: DNA
<213> ORGANISM: Artificial Sequence
<220> FEATURE:
<223> OTHER INFORMATION: Probe for elt-2

<400> SEQUENCE: 218
aatacgtggt ttttggtgtt                                          20

<210> SEQ ID NO 219
<211> LENGTH: 20
<212> TYPE: DNA
<213> ORGANISM: Artificial Sequence
<220> FEATURE:
<223> OTHER INFORMATION: Probe for elt-2

<400> SEQUENCE: 219
aagtgctata cgcgactgga                                          20

<210> SEQ ID NO 220
<211> LENGTH: 20
<212> TYPE: DNA
<213> ORGANISM: Artificial Sequence
<220> FEATURE:
<223> OTHER INFORMATION: Probe for elt-2

<400> SEQUENCE: 220
ccagaatcgg gggttgtccc                                          20

<210> SEQ ID NO 221
<211> LENGTH: 20
<212> TYPE: DNA
<213> ORGANISM: Artificial Sequence
<220> FEATURE:
<223> OTHER INFORMATION: Probe for elt-2

<400> SEQUENCE: 221
cagttggctg ctctgaaggt                                          20

<210> SEQ ID NO 222
<211> LENGTH: 20
<212> TYPE: DNA
<213> ORGANISM: Artificial Sequence
<220> FEATURE:
<223> OTHER INFORMATION: Probe for elt-2

<400> SEQUENCE: 222
tagaggattg cttggcaatt                    20

<210> SEQ ID NO 223
<211> LENGTH: 20
<212> TYPE: DNA
<213> ORGANISM: Artificial Sequence
<220> FEATURE:
<223> OTHER INFORMATION: Probe for elt-2

<400> SEQUENCE: 223
ccctatttga gctacttgac                    20

<210> SEQ ID NO 224
<211> LENGTH: 20
<212> TYPE: DNA
<213> ORGANISM: Artificial Sequence
<220> FEATURE:
<223> OTHER INFORMATION: Probe for elt-2

<400> SEQUENCE: 224
gacgggacgc agatccgttt                    20

<210> SEQ ID NO 225
<211> LENGTH: 20
<212> TYPE: DNA
<213> ORGANISM: Artificial Sequence
<220> FEATURE:
<223> OTHER INFORMATION: Probe for elt-2

<400> SEQUENCE: 225
aattggagca cacaagtccc                    20

<210> SEQ ID NO 226
<211> LENGTH: 20
<212> TYPE: DNA
<213> ORGANISM: Artificial Sequence
<220> FEATURE:
<223> OTHER INFORMATION: Probe for elt-2

<400> SEQUENCE: 226
agagagttgt gttggtacca                    20

<210> SEQ ID NO 227
<211> LENGTH: 20
<212> TYPE: DNA
<213> ORGANISM: Artificial Sequence
<220> FEATURE:
<223> OTHER INFORMATION: Probe for elt-2

<400> SEQUENCE: 227
gatctccttc agcatttctt                    20

<210> SEQ ID NO 228
<211> LENGTH: 20
<212> TYPE: DNA
<213> ORGANISM: Artificial Sequence
<220> FEATURE:
<223> OTHER INFORMATION: Probe for elt-2

<400> SEQUENCE: 228
aaagcccgca agcattgcag                    20

```
<210> SEQ ID NO 229
<211> LENGTH: 20
<212> TYPE: DNA
<213> ORGANISM: Artificial Sequence
<220> FEATURE:
<223> OTHER INFORMATION: Probe for elt-2

<400> SEQUENCE: 229
gagggatgtg atggagtttg                                               20

<210> SEQ ID NO 230
<211> LENGTH: 20
<212> TYPE: DNA
<213> ORGANISM: Artificial Sequence
<220> FEATURE:
<223> OTHER INFORMATION: Probe for elt-2

<400> SEQUENCE: 230
cttctttctt cattgaggtc                                               20

<210> SEQ ID NO 231
<211> LENGTH: 20
<212> TYPE: DNA
<213> ORGANISM: Artificial Sequence
<220> FEATURE:
<223> OTHER INFORMATION: Probe for elt-2

<400> SEQUENCE: 231
tggaagagtc tccgcttttt                                               20

<210> SEQ ID NO 232
<211> LENGTH: 20
<212> TYPE: DNA
<213> ORGANISM: Artificial Sequence
<220> FEATURE:
<223> OTHER INFORMATION: Probe for elt-2

<400> SEQUENCE: 232
ctcgggcccg tgacgttgat                                               20

<210> SEQ ID NO 233
<211> LENGTH: 20
<212> TYPE: DNA
<213> ORGANISM: Artificial Sequence
<220> FEATURE:
<223> OTHER INFORMATION: Probe for elt-2

<400> SEQUENCE: 233
aagaggctct ctcaaacttc                                               20

<210> SEQ ID NO 234
<211> LENGTH: 20
<212> TYPE: DNA
<213> ORGANISM: Artificial Sequence
<220> FEATURE:
<223> OTHER INFORMATION: Probe for elt-2

<400> SEQUENCE: 234
acctttgagc cttttcggtc                                               20

<210> SEQ ID NO 235
<211> LENGTH: 20
<212> TYPE: DNA
<213> ORGANISM: Artificial Sequence
<220> FEATURE:
<223> OTHER INFORMATION: Probe for elt-2
```

-continued

<400> SEQUENCE: 235
cacttcccgc acgccggtta                                              20

<210> SEQ ID NO 236
<211> LENGTH: 20
<212> TYPE: DNA
<213> ORGANISM: Artificial Sequence
<220> FEATURE:
<223> OTHER INFORMATION: Probe for elt-2

<400> SEQUENCE: 236
tgctcagttc tcggtctgct                                              20

<210> SEQ ID NO 237
<211> LENGTH: 20
<212> TYPE: DNA
<213> ORGANISM: Artificial Sequence
<220> FEATURE:
<223> OTHER INFORMATION: Probe for elt-2

<400> SEQUENCE: 237
agtcggcatg tgacacatat                                              20

<210> SEQ ID NO 238
<211> LENGTH: 20
<212> TYPE: DNA
<213> ORGANISM: Artificial Sequence
<220> FEATURE:
<223> OTHER INFORMATION: Probe for elt-2

<400> SEQUENCE: 238
cggcagctga ggaaacggga                                              20

<210> SEQ ID NO 239
<211> LENGTH: 20
<212> TYPE: DNA
<213> ORGANISM: Artificial Sequence
<220> FEATURE:
<223> OTHER INFORMATION: Probe for elt-2

<400> SEQUENCE: 239
tgtacgtttg atctggcaag                                              20

<210> SEQ ID NO 240
<211> LENGTH: 20
<212> TYPE: DNA
<213> ORGANISM: Artificial Sequence
<220> FEATURE:
<223> OTHER INFORMATION: Probe for elt-2

<400> SEQUENCE: 240
ccatcatcaa cccagctgta                                              20

<210> SEQ ID NO 241
<211> LENGTH: 20
<212> TYPE: DNA
<213> ORGANISM: Artificial Sequence
<220> FEATURE:
<223> OTHER INFORMATION: Probe for elt-2

<400> SEQUENCE: 241
cagtctggta gtttgttgct                                              20

<210> SEQ ID NO 242

-continued

```
<211> LENGTH: 20
<212> TYPE: DNA
<213> ORGANISM: Artificial Sequence
<220> FEATURE:
<223> OTHER INFORMATION: Probe for elt-2

<400> SEQUENCE: 242
ggatgttatc ggcaggtctt                                            20

<210> SEQ ID NO 243
<211> LENGTH: 20
<212> TYPE: DNA
<213> ORGANISM: Artificial Sequence
<220> FEATURE:
<223> OTHER INFORMATION: Probe for elt-2

<400> SEQUENCE: 243
cctgaactgg catcacatga                                            20

<210> SEQ ID NO 244
<211> LENGTH: 20
<212> TYPE: DNA
<213> ORGANISM: Artificial Sequence
<220> FEATURE:
<223> OTHER INFORMATION: Probe for elt-2

<400> SEQUENCE: 244
gagccgcagc tttggtttca                                            20

<210> SEQ ID NO 245
<211> LENGTH: 20
<212> TYPE: DNA
<213> ORGANISM: Artificial Sequence
<220> FEATURE:
<223> OTHER INFORMATION: Probe for elt-2

<400> SEQUENCE: 245
ctccgtcgac cgcttccaaa                                            20

<210> SEQ ID NO 246
<211> LENGTH: 1374
<212> TYPE: DNA
<213> ORGANISM: Artificial Sequence
<220> FEATURE:
<223> OTHER INFORMATION: Probe for FKBP5

<400> SEQUENCE: 246
atgactactg atgaaggtgc caagaacaat gaagaaagcc ccacagccac tgttgctgag    60
cagggagagg atattaccct caaaaaagac aggggagtat taaagattgt caaaagagtg   120
gggaatggtg aggaaacgcc gatgattgga gacaaagttt atgtccatta caaggaaaa    180 ttgtcaaatg gaaagaagtt tgattccagt catgatagaa atgaaccatt tgtctttagt   240
cttggcaaag gccaagtcat caaggcatgg gacattgggg tggctaccat gaagaaagga   300
gagatatgcc atttactgtg caaaccagaa tatgcatatg gctcggctgg cagtctccct   360
aaaattccct cgaatgcaac tctctttttt gagattgagc tccttgattt caaaggagag   420
gatttatttg aagatggagg cattatccgg agaaccaaac ggaaaggaga gggatattca   480
aatccaaacg aaggagcaac agtagaaatc cacctggaag gccgctgtgg tggaaggatg   540
tttgactgca gagatgtggc attcactgtg ggcgaaggag aagaccacga cattccaatt   600
ggaattgaca agctctggga gaaatgcag cgggaagaac aatgtatttt atatcttgga   660
ccaagatatg gttttggaga ggcagggaag cctaaatttg gcattgaacc taatgctgag   720
```

-continued

```
cttatatatg aagttacact taagagcttc gaaaaggcca aagaatcctg ggagatggat      780
accaaagaaa aattggagca ggctgccatt gtcaaagaga agggaaccgt atacttcaag      840
ggaggcaaat acatgcaggc ggtgattcag tatgggaaga tagtgtcctg gttagagatg     900
gaatatggtt tatcagaaaa ggaatcgaaa gcttctgaat catttctcct tgctgccttt     960
ctgaacctgg ccatgtgcta cctgaagctt agagaataca ccaaagctgt tgaatgctgt    1020
gacaaggccc ttggactgga cagtgccaat gagaaaggct tgtataggag gggtgaagcc    1080
cagctgctca tgaacgagtt tgagtcagcc aagggtgact ttgagaaagt gctggaagta    1140 aaccccccaga ataaggctgc aagactgcag atctccatgt gccagaaaaa ggccaaggag   1200
cacaacgagc gggaccgcag gatatacgcc aacatgttca agaagtttgc agagcaggat    1260
gccaaggaag aggccaataa agcaatgggc aagaagactt cagaaggggt cactaatgaa    1320
aaaggaacag acagtcaagc aatggaagaa gagaaacctg agggccacgt atga           1374
```

<210> SEQ ID NO 247
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 247
gttcttggca ccttcat                                                    17

<210> SEQ ID NO 248
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 248
aatcatcggc gtttcct                                                    17

<210> SEQ ID NO 249
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 249
tggacataaa ctttgtc                                                    17

<210> SEQ ID NO 250
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 250
ttgacaattt tcctttg                                                    17

<210> SEQ ID NO 251
<211> LENGTH: 17
<212> TYPE: DNA
<213> ORGANISM: Artificial Sequence
<220> FEATURE:
<223> OTHER INFORMATION: Probe for FKBP5

```
<400> SEQUENCE: 251
ggaatcaaac ttctttc                                                   17

<210> SEQ ID NO 252
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 252
ggttcatttc tatcatg                                                   17

<210> SEQ ID NO 253
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 253
tgccaagact aaagaca                                                   17

<210> SEQ ID NO 254
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 254
tgccttgatg acttggc                                                   17

<210> SEQ ID NO 255
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 255
gtagccaccc caatgtc                                                   17

<210> SEQ ID NO 256
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 256
atatctctcc tttcttc                                                   17

<210> SEQ ID NO 257
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 257
tggtttgcac agtaaat                                                   17

<210> SEQ ID NO 258
<211> LENGTH: 17
```

```
<212> TYPE: DNA
<213> ORGANISM: Artificial Sequence
<220> FEATURE:
<223> OTHER INFORMATION: Probe for FKBP5

<400> SEQUENCE: 258
gccgagccat atgcata                                                    17

<210> SEQ ID NO 259
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 259
gaattttagg gagactg                                                    17

<210> SEQ ID NO 260
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 260
aaagagagtt gcattcg                                                    17

<210> SEQ ID NO 261
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 261
tcaaggagct caatctc                                                    17

<210> SEQ ID NO 262
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 262
ataaatcctc tcctttg                                                    17

<210> SEQ ID NO 263
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 263
gataatgcct ccatctt                                                    17

<210> SEQ ID NO 264
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 264
```

```
cctttccgtt tggttct                                            17

<210> SEQ ID NO 265
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 265
ttggatttga atatccc                                            17

<210> SEQ ID NO 266
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 266
ttctactgtt gctcctt                                            17

<210> SEQ ID NO 267
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 267
cagcggcctt ccaggtg                                            17

<210> SEQ ID NO 268
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 268
agtcaaacat ccttcca                                            17

<210> SEQ ID NO 269
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 269
agtgaatgcc acatctc                                            17

<210> SEQ ID NO 270
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 270
tggtcttctc cttcgcc                                            17

<210> SEQ ID NO 271
<211> LENGTH: 17
<212> TYPE: DNA
<213> ORGANISM: Artificial Sequence
```

```
<220> FEATURE:
<223> OTHER INFORMATION: Probe for FKBP5

<400> SEQUENCE: 271
caattccaat tggaatg                                                  17

<210> SEQ ID NO 272
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 272
cattttctcc agagctt                                                  17

<210> SEQ ID NO 273
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 273
atacattgtt cttcccg                                                  17

<210> SEQ ID NO 274
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 274
atcttggtcc aagatat                                                  17

<210> SEQ ID NO 275
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 275
ccctgcctct ccaaaac                                                  17

<210> SEQ ID NO 276
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 276
tcaatgccaa atttagg                                                  17

<210> SEQ ID NO 277
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 277
atataagctc agcatta                                                  17
```

<210> SEQ ID NO 278
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 278
gctcttaagt gtaactt                                                17

<210> SEQ ID NO 279
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 279
gattctttgg ccttttc                                                17

<210> SEQ ID NO 280
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 280
ctttggtatc catctcc                                                17

<210> SEQ ID NO 281
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 281
ggcagcctgc tccaatt                                                17

<210> SEQ ID NO 282
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 282
gttcccttct ctttgac                                                17

<210> SEQ ID NO 283
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 283
tgcctccctt gaagtat                                                17

<210> SEQ ID NO 284
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 284
aatcaccgcc tgcatgt                                          17

<210> SEQ ID NO 285
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 285
gacactatct tcccata                                          17

<210> SEQ ID NO 286
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 286
catattccat ctctaac                                          17

<210> SEQ ID NO 287
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 287
cgattccttt tctgata                                          17

<210> SEQ ID NO 288
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 288
agaaatgatt cagaagc                                          17

<210> SEQ ID NO 289
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 289
ggttcagaaa ggcagca                                          17

<210> SEQ ID NO 290
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 290
cttcaggtag cacatgg                                          17

<210> SEQ ID NO 291

```
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 291
gctttggtgt attctct                                                    17

<210> SEQ ID NO 292
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 292
ccttgtcaca gcattca                                                    17

<210> SEQ ID NO 293
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 293
ggcactgtcc agtccaa                                                    17

<210> SEQ ID NO 294
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 294
ctatacaagc ctttctc                                                    17

<210> SEQ ID NO 295
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 295
gcagctgggc ttcaccc                                                    17

<210> SEQ ID NO 296
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 296
tgactcaaac tcgttca                                                    17

<210> SEQ ID NO 297
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 297
```

```
ttctggcaca tggagat                                                    17
```

<210> SEQ ID NO 298
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 298

```
cgttgtgctc cttggcc                                                    17
```

<210> SEQ ID NO 299
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 299

```
gtatatcctg cggtccc                                                    17
```

<210> SEQ ID NO 300
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 300

```
aacttcttga acatgtt                                                    17
```

<210> SEQ ID NO 301
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 301

```
ccttggcatc ctgctct                                                    17
```

<210> SEQ ID NO 302
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 302

```
cattgcttta ttggcct                                                    17
```

<210> SEQ ID NO 303
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 303

```
ccttctgaag tcttctt                                                    17
```

<210> SEQ ID NO 304
<211> LENGTH: 17
<212> TYPE: DNA

```
<213> ORGANISM: Artificial Sequence
<220> FEATURE:
<223> OTHER INFORMATION: Probe for FKBP5

<400> SEQUENCE: 304
ttcctttttc attagtg                                                    17

<210> SEQ ID NO 305
<211> LENGTH: 17
<212> TYPE: DNA
<213> ORGANISM: Artificial Sequence
<220> FEATURE:
<223> OTHER INFORMATION: Probe for FKBP5

<400> SEQUENCE: 305
ttccattgct tgactgt                                                    17

<210> SEQ ID NO 306
<211> LENGTH: 18
<212> TYPE: DNA
<213> ORGANISM: Artificial Sequence
<220> FEATURE:
<223> OTHER INFORMATION: Probe for FKBP5

<400> SEQUENCE: 306
stggccctca ggtttctc                                                   18

<210> SEQ ID NO 307
<211> LENGTH: 1071
<212> TYPE: DNA
<213> ORGANISM: Artificial Sequence
<220> FEATURE:
<223> OTHER INFORMATION: Probe for FLJ11127

<400> SEQUENCE: 307
atggcggcga caaggagccc cacgcgggca agggagcggg agcggtctgg cgctcccgcc     60
gcaggaagtg accaagttca ctcctggatg ctagctacaa gccaagcctt agacactgtc    120
tggagaatgg caaaaggctt tgtgatgttg gcagtttcat ttctggtggc tgccatctgc    180
tacttccgga ggctacattt atattcaggg cacaagctga atggtggat tggatatctg     240
cagagaaaat tcaaaaggaa cctcagtgtg gaggcagagg ttgatttact cagttattgt    300
gcaagagaat ggaaaggaga gacacccgt aacaagctga tgaggaaggc ttatgaggag     360
ctattttggc ggcatcacat taaatgtgtt cgacaagtaa ggagagataa ctatgatgct    420
ctcagatcag tgttatttca gatattcagc cagggcatct cttttccatc atggatgaaa    480
gaaaaggaca ttgttaagct tcctgaaaaa ctgctgtttt cacaaggttg taattggatt    540
cagcagtaca gttttggtcc tgagaagtat acaggctcga atgtgtttgg aaaactacgg    600
aaatatgtgg aattattgaa aacacagtgg actgaattta atggcattag agattatcac    660
aagagaggaa gtatgtgcaa caccctttt tcagatgcca ttctggaata taaactttat    720
gaagctttaa agttcatcat gctgtatcaa gtcactgaag tttatgaaca aatgaagact    780
aaaaaggtca ttcccagtct ttttagactc ctgttttcca gggagacatc ctctgatcct    840
ttgagcttca tgatgaatca cctgaattct gtaggcgaca catgtggact agagcagatt    900
gatatgttta tacttggata ctcccttgaa gtaaagataa agtgttcag actgttcaag    960
tttaactcca gagactttga agtctgctac ccagaggagc ctctcaggga ctggccggag   1020
atctcctgc tgaccgagaa cgaccgccac taccacattc cagtctttta a            1071
```

```
<210> SEQ ID NO 308
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 308
cccgcgtggg gctcctt                                                   17

<210> SEQ ID NO 309
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 309
agaccgctcc cgctccc                                                   17

<210> SEQ ID NO 310
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 310
cttcctgcgg cgggagc                                                   17

<210> SEQ ID NO 311
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 311
tccaggagtg aacttgg                                                   17

<210> SEQ ID NO 312
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 312
ggcttggctt gtagcta                                                   17

<210> SEQ ID NO 313
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 313
attctccaga cagtgtc                                                   17

<210> SEQ ID NO 314
<211> LENGTH: 17
<212> TYPE: DNA
<213> ORGANISM: Artificial Sequence
<220> FEATURE:
<223> OTHER INFORMATION: Probe for FLJ11127
```

<400> SEQUENCE: 314
acatcacaaa gcctttt                                                17

<210> SEQ ID NO 315
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 315
caccagaaat gaaactg                                                17

<210> SEQ ID NO 316
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 316
cggaagtagc agatggc                                                17

<210> SEQ ID NO 317
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 317
ctgaatataa atgtagc                                                17

<210> SEQ ID NO 318
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 318
ccaccatttc agcttgt                                                17

<210> SEQ ID NO 319
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 319
tttctctgca gatatcc                                                17

<210> SEQ ID NO 320
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 320
cactgaggtt cctttttg                                               17

<210> SEQ ID NO 321
<211> LENGTH: 17

-continued

```
<212> TYPE: DNA
<213> ORGANISM: Artificial Sequence
<220> FEATURE:
<223> OTHER INFORMATION: Probe for FLJ11127

<400> SEQUENCE: 321
taaatcaacc tctgcct                                                17

<210> SEQ ID NO 322
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 322
tctcttgcac aataact                                                17

<210> SEQ ID NO 323
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 323
ggggtgtctc tcctttc                                                17

<210> SEQ ID NO 324
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 324
cttcctcatc agcttgt                                                17

<210> SEQ ID NO 325
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 325
caaaatagct cctcata                                                17

<210> SEQ ID NO 326
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 326
cacatttaat gtgatgc                                                17

<210> SEQ ID NO 327
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 327
```

```
atctctcctt acttgtc                                                17

<210> SEQ ID NO 328
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 328
gatctgagag catcata                                                17

<210> SEQ ID NO 329
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 329
tgaatatctg aaataac                                                17

<210> SEQ ID NO 330
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 330
tggaaaagag atgccct                                                17

<210> SEQ ID NO 331
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 331 tcctttctt tcatcca                                                 17

<210> SEQ ID NO 332
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 332
tttcaggaag cttaaca                                                17

<210> SEQ ID NO 333
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 333
accttgtgaa aacagca                                                17

<210> SEQ ID NO 334
<211> LENGTH: 17
<212> TYPE: DNA
<213> ORGANISM: Artificial Sequence
```

```
<220> FEATURE:
<223> OTHER INFORMATION: Probe for FLJ11127

<400> SEQUENCE: 334
tactgctgaa tccaatt                                                17

<210> SEQ ID NO 335
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 335
acttctcagg accaaaa                                                17

<210> SEQ ID NO 336
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 336
aaacacattc gagcctg                                                17

<210> SEQ ID NO 337
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 337
acatatttcc gtagttt                                                17

<210> SEQ ID NO 338
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 338
actgtgtttt caataat                                                17

<210> SEQ ID NO 339
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 339
aatgccatta aattcag                                                17

<210> SEQ ID NO 340
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 340
cctctcttgt gataatc                                                17
```

```
<210> SEQ ID NO 341
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 341
aaagggtgtt gcacata                                                17

<210> SEQ ID NO 342
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 342
ttccagaatg gcatctg                                                17

<210> SEQ ID NO 343
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 343
aaagcttcat aaagttt                                                17

<210> SEQ ID NO 344
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 344
gatacagcat gatgaac                                                17

<210> SEQ ID NO 345
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 345
ttcataaact tcagtga                                                17

<210> SEQ ID NO 346
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 346 accttttag tcttcat                                                 17

<210> SEQ ID NO 347
<211> LENGTH: 17
<212> TYPE: DNA
<213> ORGANISM: Artificial Sequence
<220> FEATURE:
<223> OTHER INFORMATION: Probe for FLJ11127
```

```
<400> SEQUENCE: 347
gtctaaaaag actggga                                              17

<210> SEQ ID NO 348
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 348
tgtctccctg gaaaaca                                              17

<210> SEQ ID NO 349
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 349
aagctcaaag gatcaga                                              17

<210> SEQ ID NO 350
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 350
aattcaggtg attcatc                                              17

<210> SEQ ID NO 351
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 351
tccacatgtg tcgccta                                              17

<210> SEQ ID NO 352
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 352
aacatatcaa tctgctc                                              17

<210> SEQ ID NO 353
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 353
caagggagta tccaagt                                              17

<210> SEQ ID NO 354
```

```
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 354
gaacactttt atcttta                                                    17

<210> SEQ ID NO 355
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 355
gagttaaact tgaacag                                                    17

<210> SEQ ID NO 356
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 356
agcagacttc aaagtct                                                    17

<210> SEQ ID NO 357
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 357
cctgagaggc tcctctg                                                    17

<210> SEQ ID NO 358
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 358
agggagatct ccggcca                                                    17

<210> SEQ ID NO 359
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 359
ggcggtcgtt ctcggtc                                                    17

<210> SEQ ID NO 360
<211> LENGTH: 17
<212> TYPE: DNA
<213> ORGANISM: Artificial Sequence
<220> FEATURE:
<223> OTHER INFORMATION: Probe for FLJ11127

<400> SEQUENCE: 360
```
aaagactgga atgtggt                                                       17

<210> SEQ ID NO 361
<211> LENGTH: 5478
<212> TYPE: DNA
<213> ORGANISM: Artificial Sequence
<220> FEATURE:
<223> OTHER INFORMATION: Probe for Map2

<400> SEQUENCE: 361

| | | |
|---|---|---|
| atggctgacg agaggaaaga cgaaggaaag gcaccacact ggacatcagc ctcactcaca | 60 |
| gaggcagctg cacacccca ctcgccagag atgaaggacc agggtggctc aggggaaggg | 120 |
| ctgagccgca gcgccaatgg atttccatac agagaggagg aggaaggcgc ctttggggag | 180 |
| cacgggtcac agggcaccta ttcagatacc aaagagaacg ggatcaacgg agagctgacc | 240 |
| tcagctgaca gagaaacagc agaggaagtg tctgcaagga tagttcaagt agtcacagct | 300 |
| gaagctgtag cagtcctgaa aggtgaacaa gagaaggagg cccaacacaa ggatcagcct | 360 |
| gcagctctgc ctttagcagc tgaagaaaca gttaatctgc caccttcccc accaccatcg | 420 |
| ccagcatcag aacaaacagc tgcactggaa gaagcctcga agatgaatt ccctgagcag | 480 |
| cagaaattgc cttcctcatt cgctgagcct ttagacaagg aggaaacgga gtttaagatg | 540 |
| caaagtaagc ctggtgaaga cttttgaacat gctgccttag ttcctcagcc ggacacaagt | 600 |
| aaaactcccc aggataaaaa ggatcccaa gacatggaag agaaaagtc gcctgccagt | 660 |
| ccatttgcgc agacttcgg taccaacctg gaagacataa aacagatcac agaaccaagc | 720 |
| ataacagtac ctagcattgg cctctccgca gagcccctag ctccaaaaga tcagaaagac | 780 |
| tggttcatcg aaatgcccgt ggaatcaaag aaggatgaat ggggtttagc tgccccaata | 840 |
| tctcctggcc ccttgacacc catgagggaa aaagatgtgc tggaggatat cccaagatgg | 900 |
| gaaggaaagc agtttgactc tcccatgcct agccccttcc acagtggaag tttcactctt | 960 |
| cccttagata ctgtgaaaga tgagagagtc acagaagggt cacaaccctt tgcccctgtc | 1020 |
| ttcttccaat cagatgacaa aatgtctctg caggacacca gtggttcagc tacttccaaa | 1080 |
| gagagttcta aagatgagga gccacagaaa gataaagcag acaaagtggc agatgttcct | 1140 |
| gtctcagaag ctaccactgt actgggagat gttcacagtc cagctgtgga aggctttgtc | 1200 |
| ggggagaaca tttcaggaga agaaaagggt accacagatc aagagaaaaa agagacttcg | 1260 |
| acacccagtg tacaggaacc tacactcact gaaactgaac cacagacaaa gcttgaagag | 1320 |
| acatcaaagg tttccatcga agaaactgtg gcaaagaag aggaatcctt gaaattaaaa | 1380 |
| gatgataaag caggtgtaat tcagacttcc accgagcatt ctttctccaa agaagaccag | 1440 |
| aaaggcgaag aacagacaat cgaagcatta aaacaagact cctttcctat aagtctagaa | 1500 |
| caggcagtta cagatgcagc catggccacc aagaccttgg aaaaggttac gtctgagcca | 1560 |
| gaggcagtaa gtgaaaagag agaaatccag ggacttttg aagaggatat agctgacaag | 1620 |
| agtaagctcg aaggcgctgg gtctgcaaca gtagccgagg ttgagatgcc attttatgaa | 1680 |
| gataaatcag ggatgtccaa gtactttgaa acatctgcat tgaaagaaga tgtgaccaga | 1740 |
| agcactgggt tgggcagtga ttactacgag ctgagtgact caagaggaaa tgcccaggaa | 1800 |
| tctcttgata ctgtatctcc caagaaccaa caagatgaaa aggaacttct ggcaaaagct | 1860 |
| tcccagccta gtcctccagc acacgaagca gggtacagca ctcttgccca gagttataca | 1920 |
| tctgatcatc cgtccgagtt acctgaagaa ccaagttctc ctcaagaaag aatgttcact | 1980 |

```
attgacccca aagtttatgg ggagaaaagg gaccttcata gtaagaacaa agatgatctg   2040
acacttagtc gaagcttggg gctgggcgga aggtctgcaa tagaacagag aagcatgtcc   2100
attaacttgc ctatgtcttg ccttgattct attgcccttg ggtttaactt tggccggggc   2160
catgatcttt cccctctggc ttctgatatt ctaaccaaca ctagcggaac gatggatgaa   2220
ggagatgatt acctgccccc caccacacct gcagtggaga agattccttg ctttccaata   2280
gagagcaaag aggaagaaga taagacagag caagcaaaag tgactggagg gcaaactacc   2340
caagttgaaa catcctccga gtcacccttc ccagccaaag aatattacaa aaatggcact   2400
gtcatggccc ctgacctgcc tgagatgcta gatctagcag ggaccaggtc cagattagct   2460
tctgtgagtg cagatgctga ggttgccagg aggaaatcag tcccatcgga ggctgtggtt   2520
gcagagagca gtactggttt gccacctgtt gctgatgaca gccaacccgt aaaaccagac   2580
agtcaacttg aagacatggg gtactgtgtg ttcaacaagt acacagtccc tctcccatcg   2640
ccagttcaag acagtgagaa tttgtcagga gagagtggtt cgttttatga aggaaccgat   2700
gacaaagtcc gtagagattt ggccactgac ctttcactaa ttgaggtaaa acttgcagct   2760
gctggaagag tcaaagatga attcactgct gagaagagg catctccacc ctcttctgct   2820
gacaaatcag gactgagtag ggagtttgac caagacagga aagctaatga caagctggat   2880
actgtcctag aaaagagcga agagcatgtt gattcaaaag aacatgccaa ggagtcagaa   2940
gaggttgggg ataaagtaga gctcttcgga ttaggtgtaa cctatgagca aacctctgcc   3000
aaagaactga taacaactaa agaaacagca cctgagagag cagagaaagg tctcagttca   3060
gtgccagagg tagctgaggt agaaacaacc acaaaagctg accaaggtct agatgttgct   3120
gccaagaaag atgatcagag tccattagat ataaaagtca gtgactttgg acagatggct   3180
tctgggatga gtgtagatgc tgggaaaacc atagagctta agttcgaggt tgatcagcag   3240
ctgactctct catccgaagc acctcaggaa acagattcat tcatgggtat tgagtccagc   3300
cacgtgaagg atggtgccaa agtcagtgaa acagaagtca aagagaaggt ggcaaagcct   3360
gacttggtgc atcaggaggc tgtggacaaa gaagagtcct atgagtctag tggtgagcat   3420
gaaagcctca ccatggagtc cctgaagcct gatgagggca agaaagaaac atctccagag   3480
acatcactga tacaagatga agttgccctc aaactgtctg tagaaatccc ttgcccacct   3540
ccagtttccg aagctgattc atccattgat gagaaggcgg aggtccagat ggaattatt   3600 cagctgccaa aggaagagag cacagagact ccggatatac ctgccatacc ttctgatgtc   3660
acccagccac agcctgaagc agttgtgtcc gaaccagcag aggttcgagg tgaggaagaa   3720
gagatcgaag ctgagggaga atatgacaaa ctgctcttcc gctcagacac cctccagatc   3780
accgacctgc ttgttccagg aagtagggag gagtttgtgg agacctgccc aggggagcac   3840
aaaggtgtgg ttgagtccgt ggtaaccatc gaggatgatt tcatcactgt agtacaaacc   3900
acgactgatg agggagagtt gggatcccac agtgtgcgct tgcagctcc agttcagcct   3960 gaggaagaaa ggagaccata ccctcatgat gaagagcttg aagtactgat ggcagcagaa   4020
gcccaggcag agcccaagga tggctctcca gatgctccag ctaccctga aaagaagag   4080 gttccattct cagaatataa aacagaaacc tacgacgatt acaaagatga gaccaccatt   4140
gatgactcca ttatggatgc cgacagcctg tgggtggaca ctcaagatga tgatagaagc   4200
atcttgacag agcagttaga aactattcct aaagaggaga gagctgagaa ggaagctcgg   4260
agaccgtctc tcgagaaaca tagaaaagaa aaacctttta aaactgggag aggcagaatt   4320
tccactcctg aaagaaaagt agctaaaaag gaacctagca cggtctccag ggatgaagtg   4380
```

```
agaaggaaaa aagcagttta taagaaggct gaacttgcta aaaaatcaga agttcaggcc    4440
cactctcctt ccaggaaact cattttaaaa cctgctatca aatacactag accaactcat    4500
ctctcctgtg ttaagcggaa accacagca acaagtggtg aatcagctca ggctcccagt    4560
gcgtttaaac aggcgaagga caaagtcact gatggaataa ccaagagccc agaaaaacgt    4620
tcttccctcc caagaccttc ctccatcctc cctcctcgca ggggcgtatc aggagacagg    4680
gaggagaact cgttctctct gaacagctcc atctcttcag cacgcggac caccaggtca    4740 gaaccaattc gcagagcagg aaaaagcggc acctcaacac ctactacccc tggatctact    4800
gcaatcaccc ctggcactcc tccaagctac tcttcacgta ccccaggcac ccctggaacc    4860
ccgagctatc ccaggacacc aggaaccccc aaatttggca tcttggtgcc cagtgagaag    4920
aaagttgcca tcattcgcac tcctccaaag tccccagcta ctcccaagca gcttcggctc    4980
attaaccaac ctctgccaga cctgaagaac gtcaagtcca aaatcggatc aaccgacaac    5040
atcaaatacc agcctaaggg gggtcaggta caaattgtta ctaagaagat agacttaagc    5100
catgtgactt ccaaatgtgg ctctctaaag aacatccgtc acaggccagg tggtggacgc    5160
gtgaagattg agagtgtaaa gctggatttc aaggagaagg cccaagctaa agttggctca    5220
cttgacaatg ctcaccatgt acctggaggt ggtaacgtga agattgacag ccaaaagctg    5280
aacttccgag agcatgcaaa ggcccgcgtc gaccacgggg ctgagatcat cacacagtcg    5340
ccaagcaggt caagcgtggc gtctccccgg cgactcagca atgtctcctc ttctggaagc    5400
atcaacctgc tcgaatcccc tcagctggcc actttggctg aggacgtcac tgcggcgctc    5460
gctaagcagg gcttgtga                                                 5478
```

<210> SEQ ID NO 362
<211> LENGTH: 20
<212> TYPE: DNA
<213> ORGANISM: Artificial Sequence
<220> FEATURE:
<223> OTHER INFORMATION: Probe for Map2

<400> SEQUENCE: 362
tgtggtgcct ttccttcgtc                                               20

<210> SEQ ID NO 363
<211> LENGTH: 20
<212> TYPE: DNA
<213> ORGANISM: Artificial Sequence
<220> FEATURE:
<223> OTHER INFORMATION: Probe for Map2

<400> SEQUENCE: 363
gctgcctctg tgagtgaggc                                               20

<210> SEQ ID NO 364
<211> LENGTH: 20
<212> TYPE: DNA
<213> ORGANISM: Artificial Sequence
<220> FEATURE:
<223> OTHER INFORMATION: Probe for Map2

<400> SEQUENCE: 364
tccttcatct ctggcgagtg                                               20

<210> SEQ ID NO 365
<211> LENGTH: 20
<212> TYPE: DNA

```
<213> ORGANISM: Artificial Sequence
<220> FEATURE:
<223> OTHER INFORMATION: Probe for Map2

<400> SEQUENCE: 365
cggctcagcc cttcccctga                                               20

<210> SEQ ID NO 366
<211> LENGTH: 18
<212> TYPE: DNA
<213> ORGANISM: Artificial Sequence
<220> FEATURE:
<223> OTHER INFORMATION: Probe for Map2

<400> SEQUENCE: 366
tcctctctgt atggaaat                                                 18

<210> SEQ ID NO 367
<211> LENGTH: 20
<212> TYPE: DNA
<213> ORGANISM: Artificial Sequence
<220> FEATURE:
<223> OTHER INFORMATION: Probe for Map2

<400> SEQUENCE: 367
gacccgtgct ccccaaaggc                                               20

<210> SEQ ID NO 368
<211> LENGTH: 20
<212> TYPE: DNA
<213> ORGANISM: Artificial Sequence
<220> FEATURE:
<223> OTHER INFORMATION: Probe for Map2

<400> SEQUENCE: 368
ttctctttgg tatctgaata                                               20

<210> SEQ ID NO 369
<211> LENGTH: 20
<212> TYPE: DNA
<213> ORGANISM: Artificial Sequence
<220> FEATURE:
<223> OTHER INFORMATION: Probe for Map2

<400> SEQUENCE: 369
tcagctgagg tcagctctcc                                               20

<210> SEQ ID NO 370
<211> LENGTH: 20
<212> TYPE: DNA
<213> ORGANISM: Artificial Sequence
<220> FEATURE:
<223> OTHER INFORMATION: Probe for Map2

<400> SEQUENCE: 370
cttgcagaca cttcctctgc                                               20

<210> SEQ ID NO 371
<211> LENGTH: 20
<212> TYPE: DNA
<213> ORGANISM: Artificial Sequence
<220> FEATURE:
<223> OTHER INFORMATION: Probe for Map2

<400> SEQUENCE: 371
acagcttcag ctgtgactac                                               20
```

```
<210> SEQ ID NO 372
<211> LENGTH: 20
<212> TYPE: DNA
<213> ORGANISM: Artificial Sequence
<220> FEATURE:
<223> OTHER INFORMATION: Probe for Map2

<400> SEQUENCE: 372
tccttctctt gttcaccttt                                               20

<210> SEQ ID NO 373
<211> LENGTH: 20
<212> TYPE: DNA
<213> ORGANISM: Artificial Sequence
<220> FEATURE:
<223> OTHER INFORMATION: Probe for Map2

<400> SEQUENCE: 373
agagctgcag gctgatcctt                                               20

<210> SEQ ID NO 374
<211> LENGTH: 20
<212> TYPE: DNA
<213> ORGANISM: Artificial Sequence
<220> FEATURE:
<223> OTHER INFORMATION: Probe for Map2

<400> SEQUENCE: 374
agattaactg tttcttcagc                                               20

<210> SEQ ID NO 375
<211> LENGTH: 20
<212> TYPE: DNA
<213> ORGANISM: Artificial Sequence
<220> FEATURE:
<223> OTHER INFORMATION: Probe for Map2

<400> SEQUENCE: 375
gatgctggcg atggtggtgg                                               20

<210> SEQ ID NO 376
<211> LENGTH: 20
<212> TYPE: DNA
<213> ORGANISM: Artificial Sequence
<220> FEATURE:
<223> OTHER INFORMATION: Probe for Map2

<400> SEQUENCE: 376
gaggcttctt ccagtgcagc                                               20

<210> SEQ ID NO 377
<211> LENGTH: 20
<212> TYPE: DNA
<213> ORGANISM: Artificial Sequence
<220> FEATURE:
<223> OTHER INFORMATION: Probe for Map2

<400> SEQUENCE: 377
aatttctgct gctcagggaa                                               20

<210> SEQ ID NO 378
<211> LENGTH: 20
<212> TYPE: DNA
<213> ORGANISM: Artificial Sequence
<220> FEATURE:
```

```
<223> OTHER INFORMATION: Probe for Map2

<400> SEQUENCE: 378
ttgtctaaag gctcagcgaa                                              20

<210> SEQ ID NO 379
<211> LENGTH: 20
<212> TYPE: DNA
<213> ORGANISM: Artificial Sequence
<220> FEATURE:
<223> OTHER INFORMATION: Probe for Map2

<400> SEQUENCE: 379
ttactttgca tcttaaactc                                              20

<210> SEQ ID NO 380
<211> LENGTH: 20
<212> TYPE: DNA
<213> ORGANISM: Artificial Sequence
<220> FEATURE:
<223> OTHER INFORMATION: Probe for Map2

<400> SEQUENCE: 380
ctgaaacttg tacgacggaa                                              20

<210> SEQ ID NO 381
<211> LENGTH: 20
<212> TYPE: DNA
<213> ORGANISM: Artificial Sequence
<220> FEATURE:
<223> OTHER INFORMATION: Probe for Map2

<400> SEQUENCE: 381
ggagttttac ttgtgtccgg                                              20

<210> SEQ ID NO 382
<211> LENGTH: 20
<212> TYPE: DNA
<213> ORGANISM: Artificial Sequence
<220> FEATURE:
<223> OTHER INFORMATION: Probe for Map2

<400> SEQUENCE: 382
tccatgtctt ggggatcctt                                              20

<210> SEQ ID NO 383
<211> LENGTH: 20
<212> TYPE: DNA
<213> ORGANISM: Artificial Sequence
<220> FEATURE:
<223> OTHER INFORMATION: Probe for Map2

<400> SEQUENCE: 383
gcaaatggac tggcaggcga                                              20

<210> SEQ ID NO 384
<211> LENGTH: 20
<212> TYPE: DNA
<213> ORGANISM: Artificial Sequence
<220> FEATURE:
<223> OTHER INFORMATION: Probe for Map2

<400> SEQUENCE: 384
atgtcttcca ggttggtacc                                              20
```

-continued

```
<210> SEQ ID NO 385
<211> LENGTH: 20
<212> TYPE: DNA
<213> ORGANISM: Artificial Sequence
<220> FEATURE:
<223> OTHER INFORMATION: Probe for Map2

<400> SEQUENCE: 385
actgttatgc ttggttctgt                                                   20

<210> SEQ ID NO 386
<211> LENGTH: 20
<212> TYPE: DNA
<213> ORGANISM: Artificial Sequence
<220> FEATURE:
<223> OTHER INFORMATION: Probe for Map2

<400> SEQUENCE: 386
aggggctctg cggagaggcc                                                   20

<210> SEQ ID NO 387
<211> LENGTH: 20
<212> TYPE: DNA
<213> ORGANISM: Artificial Sequence
<220> FEATURE:
<223> OTHER INFORMATION: Probe for Map2

<400> SEQUENCE: 387
atgaaccagt ctttctgatc                                                   20

<210> SEQ ID NO 388
<211> LENGTH: 20
<212> TYPE: DNA
<213> ORGANISM: Artificial Sequence
<220> FEATURE:
<223> OTHER INFORMATION: Probe for Map2

<400> SEQUENCE: 388
tcatccttct ttgattccac                                                   20

<210> SEQ ID NO 389
<211> LENGTH: 20
<212> TYPE: DNA
<213> ORGANISM: Artificial Sequence
<220> FEATURE:
<223> OTHER INFORMATION: Probe for Map2

<400> SEQUENCE: 389
ccaggagata ttggggcagc                                                   20

<210> SEQ ID NO 390
<211> LENGTH: 20
<212> TYPE: DNA
<213> ORGANISM: Artificial Sequence
<220> FEATURE:
<223> OTHER INFORMATION: Probe for Map2

<400> SEQUENCE: 390 acatctttt ccctcatggg                                                    20

<210> SEQ ID NO 391
<211> LENGTH: 20
<212> TYPE: DNA
<213> ORGANISM: Artificial Sequence
<220> FEATURE:
<223> OTHER INFORMATION: Probe for Map2
```

<400> SEQUENCE: 391
tttccttccc atcttgggat                                               20

<210> SEQ ID NO 392
<211> LENGTH: 20
<212> TYPE: DNA
<213> ORGANISM: Artificial Sequence
<220> FEATURE:
<223> OTHER INFORMATION: Probe for Map2

<400> SEQUENCE: 392
aaggggctag gcatgggaga                                               20

<210> SEQ ID NO 393
<211> LENGTH: 20
<212> TYPE: DNA
<213> ORGANISM: Artificial Sequence
<220> FEATURE:
<223> OTHER INFORMATION: Probe for Map2

<400> SEQUENCE: 393
tctaagggaa gagtgaaact                                               20

<210> SEQ ID NO 394
<211> LENGTH: 20
<212> TYPE: DNA
<213> ORGANISM: Artificial Sequence
<220> FEATURE:
<223> OTHER INFORMATION: Probe for Map2

<400> SEQUENCE: 394
ccttctgtga ctctctcatc                                               20

<210> SEQ ID NO 395
<211> LENGTH: 20
<212> TYPE: DNA
<213> ORGANISM: Artificial Sequence
<220> FEATURE:
<223> OTHER INFORMATION: Probe for Map2

<400> SEQUENCE: 395
tggaagaaga cagggggcaaa                                              20

<210> SEQ ID NO 396
<211> LENGTH: 20
<212> TYPE: DNA
<213> ORGANISM: Artificial Sequence
<220> FEATURE:
<223> OTHER INFORMATION: Probe for Map2

<400> SEQUENCE: 396
gtgtcctgca gagacatttt                                               20

<210> SEQ ID NO 397
<211> LENGTH: 20
<212> TYPE: DNA
<213> ORGANISM: Artificial Sequence
<220> FEATURE:
<223> OTHER INFORMATION: Probe for Map2

<400> SEQUENCE: 397
gaactctctt tggaagtagc                                               20

<210> SEQ ID NO 398
<211> LENGTH: 20

```
<212> TYPE: DNA
<213> ORGANISM: Artificial Sequence
<220> FEATURE:
<223> OTHER INFORMATION: Probe for Map2

<400> SEQUENCE: 398
gctttatctt tctgtggctc                                               20

<210> SEQ ID NO 399
<211> LENGTH: 20
<212> TYPE: DNA
<213> ORGANISM: Artificial Sequence
<220> FEATURE:
<223> OTHER INFORMATION: Probe for Map2

<400> SEQUENCE: 399
tctgagacag gaacatctgc                                               20

<210> SEQ ID NO 400
<211> LENGTH: 20
<212> TYPE: DNA
<213> ORGANISM: Artificial Sequence
<220> FEATURE:
<223> OTHER INFORMATION: Probe for Map2

<400> SEQUENCE: 400
ctgtgaacat ctcccagtac                                               20

<210> SEQ ID NO 401
<211> LENGTH: 20
<212> TYPE: DNA
<213> ORGANISM: Artificial Sequence
<220> FEATURE:
<223> OTHER INFORMATION: Probe for Map2

<400> SEQUENCE: 401
ttctccccga caaagccttc                                               20

<210> SEQ ID NO 402
<211> LENGTH: 20
<212> TYPE: DNA
<213> ORGANISM: Artificial Sequence
<220> FEATURE:
<223> OTHER INFORMATION: Probe for Map2

<400> SEQUENCE: 402
tctgtggtac cctttcttc                                                20

<210> SEQ ID NO 403
<211> LENGTH: 20
<212> TYPE: DNA
<213> ORGANISM: Artificial Sequence
<220> FEATURE:
<223> OTHER INFORMATION: Probe for Map2

<400> SEQUENCE: 403
ctgggtgtcg aagtctcttt                                               20

<210> SEQ ID NO 404
<211> LENGTH: 20
<212> TYPE: DNA
<213> ORGANISM: Artificial Sequence
<220> FEATURE:
<223> OTHER INFORMATION: Probe for Map2

<400> SEQUENCE: 404
```
tcagtttcag tgagtgtagg                                              20

<210> SEQ ID NO 405
<211> LENGTH: 20
<212> TYPE: DNA
<213> ORGANISM: Artificial Sequence
<220> FEATURE:
<223> OTHER INFORMATION: Probe for Map2

<400> SEQUENCE: 405
tttgatgtct cttcaagctt                                              20

<210> SEQ ID NO 406
<211> LENGTH: 20
<212> TYPE: DNA
<213> ORGANISM: Artificial Sequence
<220> FEATURE:
<223> OTHER INFORMATION: Probe for Map2

<400> SEQUENCE: 406
tcttttgcca cagtttcttc                                              20

<210> SEQ ID NO 407
<211> LENGTH: 20
<212> TYPE: DNA
<213> ORGANISM: Artificial Sequence
<220> FEATURE:
<223> OTHER INFORMATION: Probe for Map2

<400> SEQUENCE: 407
ttatcatctt ttaatttcaa                                              20

<210> SEQ ID NO 408
<211> LENGTH: 20
<212> TYPE: DNA
<213> ORGANISM: Artificial Sequence
<220> FEATURE:
<223> OTHER INFORMATION: Probe for Map2

<400> SEQUENCE: 408
tgctcggtgg aagtctgaat                                              20

<210> SEQ ID NO 409
<211> LENGTH: 20
<212> TYPE: DNA
<213> ORGANISM: Artificial Sequence
<220> FEATURE:
<223> OTHER INFORMATION: Probe for Map2

<400> SEQUENCE: 409
tcgcctttct ggtcttcttt                                              20

<210> SEQ ID NO 410
<211> LENGTH: 20
<212> TYPE: DNA
<213> ORGANISM: Artificial Sequence
<220> FEATURE:
<223> OTHER INFORMATION: Probe for Map2

<400> SEQUENCE: 410
cagacccagc gccttcgagc                                              20

<210> SEQ ID NO 411
<211> LENGTH: 20
<212> TYPE: DNA
<213> ORGANISM: Artificial Sequence

```
<220> FEATURE:
<223> OTHER INFORMATION: Probe for Map2

<400> SEQUENCE: 411 gcccaacccà gtgcttctgg                                              20

<210> SEQ ID NO 412
<211> LENGTH: 20
<212> TYPE: DNA
<213> ORGANISM: Artificial Sequence
<220> FEATURE:
<223> OTHER INFORMATION: Probe for Map2

<400> SEQUENCE: 412
gctggaggac taggctggga                                              20

<210> SEQ ID NO 413
<211> LENGTH: 20
<212> TYPE: DNA
<213> ORGANISM: Artificial Sequence
<220> FEATURE:
<223> OTHER INFORMATION: Probe for Map2

<400> SEQUENCE: 413
ccgcccagcc ccaagcttcg                                              20

<210> SEQ ID NO 414
<211> LENGTH: 20
<212> TYPE: DNA
<213> ORGANISM: Artificial Sequence
<220> FEATURE:
<223> OTHER INFORMATION: Probe for Map2

<400> SEQUENCE: 414
gatcatggcc ccggccaaag                                              20

<210> SEQ ID NO 415
<211> LENGTH: 20
<212> TYPE: DNA
<213> ORGANISM: Artificial Sequence
<220> FEATURE:
<223> OTHER INFORMATION: Probe for Map2

<400> SEQUENCE: 415
caggtgtggt gggggggcagg                                             20

<210> SEQ ID NO 416
<211> LENGTH: 20
<212> TYPE: DNA
<213> ORGANISM: Artificial Sequence
<220> FEATURE:
<223> OTHER INFORMATION: Probe for Map2

<400> SEQUENCE: 416
ggctgggaag ggtgactcgg                                              20

<210> SEQ ID NO 417
<211> LENGTH: 20
<212> TYPE: DNA
<213> ORGANISM: Artificial Sequence
<220> FEATURE:
<223> OTHER INFORMATION: Probe for Map2

<400> SEQUENCE: 417
ggcaggtcag gggccatgac                                              20
```

<210> SEQ ID NO 418
<211> LENGTH: 20
<212> TYPE: DNA
<213> ORGANISM: Artificial Sequence
<220> FEATURE:
<223> OTHER INFORMATION: Probe for Map2

<400> SEQUENCE: 418
ctggacctgg tccctgctag            20

<210> SEQ ID NO 419
<211> LENGTH: 20
<212> TYPE: DNA
<213> ORGANISM: Artificial Sequence
<220> FEATURE:
<223> OTHER INFORMATION: Probe for Map2

<400> SEQUENCE: 419
cacagcctcc gatgggactg            20

<210> SEQ ID NO 420
<211> LENGTH: 20
<212> TYPE: DNA
<213> ORGANISM: Artificial Sequence
<220> FEATURE:
<223> OTHER INFORMATION: Probe for Map2

<400> SEQUENCE: 420
gaactggcga tgggagaggg            20

<210> SEQ ID NO 421
<211> LENGTH: 20
<212> TYPE: DNA
<213> ORGANISM: Artificial Sequence
<220> FEATURE:
<223> OTHER INFORMATION: Probe for Map2

<400> SEQUENCE: 421
gccctcatca ggcttcaggg            20

<210> SEQ ID NO 422
<211> LENGTH: 20
<212> TYPE: DNA
<213> ORGANISM: Artificial Sequence
<220> FEATURE:
<223> OTHER INFORMATION: Probe for Map2

<400> SEQUENCE: 422
ccatctggac ctccgccttc            20

<210> SEQ ID NO 423
<211> LENGTH: 20
<212> TYPE: DNA
<213> ORGANISM: Artificial Sequence
<220> FEATURE:
<223> OTHER INFORMATION: Probe for Map2

<400> SEQUENCE: 423
tcaggctgtg gctgggtgac            20

<210> SEQ ID NO 424
<211> LENGTH: 20
<212> TYPE: DNA
<213> ORGANISM: Artificial Sequence
<220> FEATURE:
<223> OTHER INFORMATION: Probe for Map2

<400> SEQUENCE: 424
tctggagggt gtctgagcgg					20

<210> SEQ ID NO 425
<211> LENGTH: 20
<212> TYPE: DNA
<213> ORGANISM: Artificial Sequence
<220> FEATURE:
<223> OTHER INFORMATION: Probe for Map2

<400> SEQUENCE: 425
gctcccctgg gcaggtctcc					20

<210> SEQ ID NO 426
<211> LENGTH: 20
<212> TYPE: DNA
<213> ORGANISM: Artificial Sequence
<220> FEATURE:
<223> OTHER INFORMATION: Probe for Map2

<400> SEQUENCE: 426
agcgcacact gtgggatccc					20

<210> SEQ ID NO 427
<211> LENGTH: 20
<212> TYPE: DNA
<213> ORGANISM: Artificial Sequence
<220> FEATURE:
<223> OTHER INFORMATION: Probe for Map2

<400> SEQUENCE: 427
tccttgggct ctgcctgggc					20

<210> SEQ ID NO 428
<211> LENGTH: 20
<212> TYPE: DNA
<213> ORGANISM: Artificial Sequence
<220> FEATURE:
<223> OTHER INFORMATION: Probe for Map2

<400> SEQUENCE: 428
gctggagcat ctggagagcc					20

<210> SEQ ID NO 429
<211> LENGTH: 20
<212> TYPE: DNA
<213> ORGANISM: Artificial Sequence
<220> FEATURE:
<223> OTHER INFORMATION: Probe for Map2

<400> SEQUENCE: 429
tccacccaca ggctgtcggc					20

<210> SEQ ID NO 430
<211> LENGTH: 20
<212> TYPE: DNA
<213> ORGANISM: Artificial Sequence
<220> FEATURE:
<223> OTHER INFORMATION: Probe for Map2

<400> SEQUENCE: 430
gagacggtct ccgagcttcc					20

<210> SEQ ID NO 431

<211> LENGTH: 20
<212> TYPE: DNA
<213> ORGANISM: Artificial Sequence
<220> FEATURE:
<223> OTHER INFORMATION: Probe for Map2

<400> SEQUENCE: 431
tccctggaga ccgtgctagg                                              20

<210> SEQ ID NO 432
<211> LENGTH: 20
<212> TYPE: DNA
<213> ORGANISM: Artificial Sequence
<220> FEATURE:
<223> OTHER INFORMATION: Probe for Map2

<400> SEQUENCE: 432
cgcactggga gcctgagctg                                              20

<210> SEQ ID NO 433
<211> LENGTH: 20
<212> TYPE: DNA
<213> ORGANISM: Artificial Sequence
<220> FEATURE:
<223> OTHER INFORMATION: Probe for Map2

<400> SEQUENCE: 433
ggaggaaggt cttgggaggg                                              20

<210> SEQ ID NO 434
<211> LENGTH: 1710
<212> TYPE: DNA
<213> ORGANISM: Artificial Sequence
<220> FEATURE:
<223> OTHER INFORMATION: Probe for STL1

<400> SEQUENCE: 434
atgaaggatt taaaattatc gaatttcaaa ggcaaattta taagcagaac cagtcactgg      60
ggacttacgg gtaagaagtt gcggtatttc atcactatcg catctatgac gggcttctcc     120
ctgtttggat acgaccaagg gttgatggca agtctaatta ctggtaaaca gttcaactat     180
gaatttccag caaccaaaga aaatggcgat catgacagac acgcaactgt agtgcagggc     240
gctacaacct cctgttatga attaggttgt ttcgcaggtt ctctattcgt tatgttctgc     300
ggtgaaagaa ttggtagaaa accattaatc ctgatgggtt ccgtaataac catcattggt     360
gccgttattt ctacatgcgc atttcgtggt tactgggcat taggccagtt tatcatcgga     420
agagtcgtca ccggtgttgg aacagggttg aatacatcta ctattcccgt ttggcaatca     480
gaaatgtcaa aagctgaaaa tagagggttg ctggtcaatt tagaaggttc cacaattgct     540
tttggtacta tgattgctta ttggattgat tttgggttgt cttataccaa cagttctgtt     600
cagtggagat tccccgtgtc aatgcaaatc gttttttgctc tcttcctgct tgctttcatg     660
attaaactac ctgaatcgcc acgttggctg atttctcaaa gtcgaacaga agaagctcgc     720
tacttggtag gaacactaga cgacgcggat ccaaatgatg aggaagttat aacagaagtt     780
gctatgcttc acgatgctgt taacaggacc aaacacgaga acattcact gtcaagtttg     840
ttctccagag gcaggtccca aaatcttcag agggctttga ttgcagcttc aacgcaattt     900
ttccagcaat ttactggttg taacgctgcc atatactact ctactgtatt attcaacaaa     960
acaattaaat tagactatag attatcaatg atcataggtg gggtcttcgc aacaatctac    1020
gccttatcta ctattggttc atttttctct attgaaaagc taggtagacg taagctgttt    1080

-continued

```
ttattaggtg ccacaggtca agcagtttca ttcacaatta catttgcatg cttggtcaaa    1140
gaaaataaag aaaacgcaag aggtgctgcc gtcggcttat ttttgttcat tacattcttt    1200
ggtttgtctt tgctatcatt accatggata tacccaccag aaattgcatc aatgaaagtt    1260
cgtgcatcaa caaacgcttt ctccacatgt actaattggt tgtgtaactt tgcggttgtc    1320
atgttcaccc caatatttat tggacagtcc ggttggggtt gctacttatt ttttgctgtt    1380
atgaattatt tatacattcc agttatcttc tttttctacc ctgaaaccgc cggaagaagt    1440
ttggaggaaa tcgacatcat ctttgctaaa gcatacgagg atggcactca accatggaga    1500
gttgctaacc atttgcccaa gttatcccta caagaagtcg aagatcatgc caatgcattg    1560
ggctcttatg acgacgaaat ggaaaaagag gactttggtg aagatagagt agaagacacc    1620
tataaccaaa ttaacggcga taattcgtct agttcttcaa acatcaaaaa tgaagataca    1680
gtgaacgata aagcaaattt tgagggttga                                     1710
```

<210> SEQ ID NO 435
<211> LENGTH: 20
<212> TYPE: DNA
<213> ORGANISM: Artificial Sequence
<220> FEATURE:
<223> OTHER INFORMATION: Probe for STL1

<400> SEQUENCE: 435
gcctttgaaa ttcgataatt                                                20

<210> SEQ ID NO 436
<211> LENGTH: 20
<212> TYPE: DNA
<213> ORGANISM: Artificial Sequence
<220> FEATURE:
<223> OTHER INFORMATION: Probe for STL1

<400> SEQUENCE: 436
cagtgactgg ttctgcttat                                                20

<210> SEQ ID NO 437
<211> LENGTH: 20
<212> TYPE: DNA
<213> ORGANISM: Artificial Sequence
<220> FEATURE:
<223> OTHER INFORMATION: Probe for STL1

<400> SEQUENCE: 437
taccgcaact tcttacccgt                                                20

<210> SEQ ID NO 438
<211> LENGTH: 20
<212> TYPE: DNA
<213> ORGANISM: Artificial Sequence
<220> FEATURE:
<223> OTHER INFORMATION: Probe for STL1

<400> SEQUENCE: 438
gaagcccgtc atagatgcga                                                20

<210> SEQ ID NO 439
<211> LENGTH: 20
<212> TYPE: DNA
<213> ORGANISM: Artificial Sequence
<220> FEATURE:
<223> OTHER INFORMATION: Probe for STL1

```
<400> SEQUENCE: 439
tcaacccttg gtcgtatcca                                               20

<210> SEQ ID NO 440
<211> LENGTH: 20
<212> TYPE: DNA
<213> ORGANISM: Artificial Sequence
<220> FEATURE:
<223> OTHER INFORMATION: Probe for STL1

<400> SEQUENCE: 440
gttgaactgt ttaccagtaa                                               20

<210> SEQ ID NO 441
<211> LENGTH: 20
<212> TYPE: DNA
<213> ORGANISM: Artificial Sequence
<220> FEATURE:
<223> OTHER INFORMATION: Probe for STL1

<400> SEQUENCE: 441
tgtctgtcat gatcgccatt                                               20

<210> SEQ ID NO 442
<211> LENGTH: 20
<212> TYPE: DNA
<213> ORGANISM: Artificial Sequence
<220> FEATURE:
<223> OTHER INFORMATION: Probe for STL1

<400> SEQUENCE: 442
gaacctgcga aacaacctaa                                               20

<210> SEQ ID NO 443
<211> LENGTH: 20
<212> TYPE: DNA
<213> ORGANISM: Artificial Sequence
<220> FEATURE:
<223> OTHER INFORMATION: Probe for STL1

<400> SEQUENCE: 443
ttcaccgcag aacataacga                                               20

<210> SEQ ID NO 444
<211> LENGTH: 20
<212> TYPE: DNA
<213> ORGANISM: Artificial Sequence
<220> FEATURE:
<223> OTHER INFORMATION: Probe for STL1

<400> SEQUENCE: 444
tacggaaccc atcaggatta                                               20

<210> SEQ ID NO 445
<211> LENGTH: 20
<212> TYPE: DNA
<213> ORGANISM: Artificial Sequence
<220> FEATURE:
<223> OTHER INFORMATION: Probe for STL1

<400> SEQUENCE: 445
cacgaaatgc gcatgtagaa                                               20

<210> SEQ ID NO 446
<211> LENGTH: 20
```

-continued

<210> SEQ ID NO 446
<211> LENGTH: 20
<212> TYPE: DNA
<213> ORGANISM: Artificial Sequence
<220> FEATURE:
<223> OTHER INFORMATION: Probe for STL1

<400> SEQUENCE: 446
tccgatgata aactggccta                20

<210> SEQ ID NO 447
<211> LENGTH: 20
<212> TYPE: DNA
<213> ORGANISM: Artificial Sequence
<220> FEATURE:
<223> OTHER INFORMATION: Probe for STL1

<400> SEQUENCE: 447
ttctgattgc caaacgggaa                20

<210> SEQ ID NO 448
<211> LENGTH: 20
<212> TYPE: DNA
<213> ORGANISM: Artificial Sequence
<220> FEATURE:
<223> OTHER INFORMATION: Probe for STL1

<400> SEQUENCE: 448
gcaaccctct attttcagct                20

<210> SEQ ID NO 449
<211> LENGTH: 20
<212> TYPE: DNA
<213> ORGANISM: Artificial Sequence
<220> FEATURE:
<223> OTHER INFORMATION: Probe for STL1

<400> SEQUENCE: 449
gcaattgtgg aaccttctaa                20

<210> SEQ ID NO 450
<211> LENGTH: 20
<212> TYPE: DNA
<213> ORGANISM: Artificial Sequence
<220> FEATURE:
<223> OTHER INFORMATION: Probe for STL1

<400> SEQUENCE: 450
caacccaaaa tcaatccaat                20

<210> SEQ ID NO 451
<211> LENGTH: 20
<212> TYPE: DNA
<213> ORGANISM: Artificial Sequence
<220> FEATURE:
<223> OTHER INFORMATION: Probe for STL1

<400> SEQUENCE: 451
cactgaacag aactgttggt                20

<210> SEQ ID NO 452
<211> LENGTH: 20
<212> TYPE: DNA
<213> ORGANISM: Artificial Sequence
<220> FEATURE:
<223> OTHER INFORMATION: Probe for STL1

<400> SEQUENCE: 452
caggaagaga gcaaaaacga                                               20

<210> SEQ ID NO 453
<211> LENGTH: 20
<212> TYPE: DNA
<213> ORGANISM: Artificial Sequence
<220> FEATURE:
<223> OTHER INFORMATION: Probe for STL1

<400> SEQUENCE: 453
gtggcgattc aggtagttta                                               20

<210> SEQ ID NO 454
<211> LENGTH: 20
<212> TYPE: DNA
<213> ORGANISM: Artificial Sequence
<220> FEATURE:
<223> OTHER INFORMATION: Probe for STL1

<400> SEQUENCE: 454
cttctgttcg actttgagaa                                               20

<210> SEQ ID NO 455
<211> LENGTH: 20
<212> TYPE: DNA
<213> ORGANISM: Artificial Sequence
<220> FEATURE:
<223> OTHER INFORMATION: Probe for STL1

<400> SEQUENCE: 455
ctgttataac ttcctcatca                                               20

<210> SEQ ID NO 456
<211> LENGTH: 20
<212> TYPE: DNA
<213> ORGANISM: Artificial Sequence
<220> FEATURE:
<223> OTHER INFORMATION: Probe for STL1

<400> SEQUENCE: 456
gttaacagca tcgtgaagca                                               20

<210> SEQ ID NO 457
<211> LENGTH: 20
<212> TYPE: DNA
<213> ORGANISM: Artificial Sequence
<220> FEATURE:
<223> OTHER INFORMATION: Probe for STL1

<400> SEQUENCE: 457
acagtgaatg tttctcgtgt                                               20

<210> SEQ ID NO 458
<211> LENGTH: 20
<212> TYPE: DNA
<213> ORGANISM: Artificial Sequence
<220> FEATURE:
<223> OTHER INFORMATION: Probe for STL1

<400> SEQUENCE: 458
ggacctgcct ctggagaaca                                               20

<210> SEQ ID NO 459
<211> LENGTH: 20
<212> TYPE: DNA
<213> ORGANISM: Artificial Sequence
<220> FEATURE:
<223> OTHER INFORMATION: Probe for STL1

<400> SEQUENCE: 459
caatcaaagc cctctgaaga                                              20

<210> SEQ ID NO 460
<211> LENGTH: 20
<212> TYPE: DNA
<213> ORGANISM: Artificial Sequence
<220> FEATURE:
<223> OTHER INFORMATION: Probe for STL1

<400> SEQUENCE: 460
gcagcgttac aaccagtaaa                                              20

<210> SEQ ID NO 461
<211> LENGTH: 20
<212> TYPE: DNA
<213> ORGANISM: Artificial Sequence
<220> FEATURE:
<223> OTHER INFORMATION: Probe for STL1

<400> SEQUENCE: 461
gaataataca gtagagtagt                                              20

<210> SEQ ID NO 462
<211> LENGTH: 20
<212> TYPE: DNA
<213> ORGANISM: Artificial Sequence
<220> FEATURE:
<223> OTHER INFORMATION: Probe for STL1

<400> SEQUENCE: 462
ccccacctat gatcattgat                                              20

<210> SEQ ID NO 463
<211> LENGTH: 20
<212> TYPE: DNA
<213> ORGANISM: Artificial Sequence
<220> FEATURE:
<223> OTHER INFORMATION: Probe for STL1

<400> SEQUENCE: 463
aatagtagat aaggcgtaga                                              20

<210> SEQ ID NO 464
<211> LENGTH: 20
<212> TYPE: DNA
<213> ORGANISM: Artificial Sequence
<220> FEATURE:
<223> OTHER INFORMATION: Probe for STL1

<400> SEQUENCE: 464
agcttacgtc tacctagctt                                              20

<210> SEQ ID NO 465
<211> LENGTH: 20
<212> TYPE: DNA
<213> ORGANISM: Artificial Sequence
<220> FEATURE:
<223> OTHER INFORMATION: Probe for STL1

<400> SEQUENCE: 465
ttgacctgtg gcacctaata                                              20

```
<210> SEQ ID NO 466
<211> LENGTH: 20
<212> TYPE: DNA
<213> ORGANISM: Artificial Sequence
<220> FEATURE:
<223> OTHER INFORMATION: Probe for STL1

<400> SEQUENCE: 466
gaccaagcat gcaaatgtaa                                                     20

<210> SEQ ID NO 467
<211> LENGTH: 20
<212> TYPE: DNA
<213> ORGANISM: Artificial Sequence
<220> FEATURE:
<223> OTHER INFORMATION: Probe for STL1

<400> SEQUENCE: 467
gcacctcttg cgttttcttt                                                     20

<210> SEQ ID NO 468
<211> LENGTH: 20
<212> TYPE: DNA
<213> ORGANISM: Artificial Sequence
<220> FEATURE:
<223> OTHER INFORMATION: Probe for STL1

<400> SEQUENCE: 468
ccaaagaatg taatgaacaa                                                     20

<210> SEQ ID NO 469
<211> LENGTH: 20
<212> TYPE: DNA
<213> ORGANISM: Artificial Sequence
<220> FEATURE:
<223> OTHER INFORMATION: Probe for STL1

<400> SEQUENCE: 469
tggtgggtat atccatggta                                                     20

<210> SEQ ID NO 470
<211> LENGTH: 20
<212> TYPE: DNA
<213> ORGANISM: Artificial Sequence
<220> FEATURE:
<223> OTHER INFORMATION: Probe for STL1

<400> SEQUENCE: 470
cgtttgttga tgcacgaact                                                     20

<210> SEQ ID NO 471
<211> LENGTH: 20
<212> TYPE: DNA
<213> ORGANISM: Artificial Sequence
<220> FEATURE:
<223> OTHER INFORMATION: Probe for STL1

<400> SEQUENCE: 471
ccgcaaagtt acacaaccaa                                                     20

<210> SEQ ID NO 472
<211> LENGTH: 20
<212> TYPE: DNA
<213> ORGANISM: Artificial Sequence
<220> FEATURE:
<223> OTHER INFORMATION: Probe for STL1
```

-continued

<400> SEQUENCE: 472
caaccggact gtccaataaa                                              20

<210> SEQ ID NO 473
<211> LENGTH: 20
<212> TYPE: DNA
<213> ORGANISM: Artificial Sequence
<220> FEATURE:
<223> OTHER INFORMATION: Probe for STL1

<400> SEQUENCE: 473
aattcataac agcaaaaaat                                              20

<210> SEQ ID NO 474
<211> LENGTH: 20
<212> TYPE: DNA
<213> ORGANISM: Artificial Sequence
<220> FEATURE:
<223> OTHER INFORMATION: Probe for STL1

<400> SEQUENCE: 474
tcagggtaga aaagaagat                                               20

<210> SEQ ID NO 475
<211> LENGTH: 20
<212> TYPE: DNA
<213> ORGANISM: Artificial Sequence
<220> FEATURE:
<223> OTHER INFORMATION: Probe for STL1

<400> SEQUENCE: 475
gatgatgtcg atttcctcca                                              20

<210> SEQ ID NO 476
<211> LENGTH: 20
<212> TYPE: DNA
<213> ORGANISM: Artificial Sequence
<220> FEATURE:
<223> OTHER INFORMATION: Probe for STL1

<400> SEQUENCE: 476
agtgccatcc tcgtatgctt                                              20

<210> SEQ ID NO 477
<211> LENGTH: 20
<212> TYPE: DNA
<213> ORGANISM: Artificial Sequence
<220> FEATURE:
<223> OTHER INFORMATION: Probe for STL1

<400> SEQUENCE: 477
ggataacttg ggcaaatggt                                              20

<210> SEQ ID NO 478
<211> LENGTH: 20
<212> TYPE: DNA
<213> ORGANISM: Artificial Sequence
<220> FEATURE:
<223> OTHER INFORMATION: Probe for STL1

<400> SEQUENCE: 478
cgtcataaga gcccaatgca                                              20

<210> SEQ ID NO 479

```
<211> LENGTH: 20
<212> TYPE: DNA
<213> ORGANISM: Artificial Sequence
<220> FEATURE:
<223> OTHER INFORMATION: Probe for STL1

<400> SEQUENCE: 479
ccaaagtcct cttttccat                                          20

<210> SEQ ID NO 480
<211> LENGTH: 20
<212> TYPE: DNA
<213> ORGANISM: Artificial Sequence
<220> FEATURE:
<223> OTHER INFORMATION: Probe for STL1

<400> SEQUENCE: 480
ttataggtgt cttctactct                                         20

<210> SEQ ID NO 481
<211> LENGTH: 20
<212> TYPE: DNA
<213> ORGANISM: Artificial Sequence
<220> FEATURE:
<223> OTHER INFORMATION: Probe for STL1

<400> SEQUENCE: 481
ctagacgaat tatcgccgtt                                         20

<210> SEQ ID NO 482
<211> LENGTH: 20
<212> TYPE: DNA
<213> ORGANISM: Artificial Sequence
<220> FEATURE:
<223> OTHER INFORMATION: Probe for STL1

<400> SEQUENCE: 482
cgttcactgt atcttcattt                                         20

<210> SEQ ID NO 483
<211> LENGTH: 80
<212> TYPE: DNA
<213> ORGANISM: Artificial Sequence
<220> FEATURE:
<223> OTHER INFORMATION: repeated 3'-UTR multimer sequence

<400> SEQUENCE: 483
tcgacgcgga gaccacgctc ggcttgtctt tcgcgcgcaa tgcgacgcac gcggatagtt   60
agctgcggcg acgaggcacc                                         80

<210> SEQ ID NO 484
<211> LENGTH: 20
<212> TYPE: DNA
<213> ORGANISM: Artificial Sequence
<220> FEATURE:
<223> OTHER INFORMATION: probe for 3'-UTR

<400> SEQUENCE: 484
gagcgtggtc tccgcgtcga                                         20

<210> SEQ ID NO 485
<211> LENGTH: 20
<212> TYPE: DNA
<213> ORGANISM: Artificial Sequence
<220> FEATURE:
<223> OTHER INFORMATION: probe for 3'-UTR
```

```
<400> SEQUENCE: 485
ttgcgcgcga aagacaagcc                                                  20

<210> SEQ ID NO 486
<211> LENGTH: 20
<212> TYPE: DNA
<213> ORGANISM: Artificial Sequence
<220> FEATURE:
<223> OTHER INFORMATION: probe for 3'-UTR

<400> SEQUENCE: 486
aactatccgc gtgcgtcgca                                                  20

<210> SEQ ID NO 487
<211> LENGTH: 20
<212> TYPE: DNA
<213> ORGANISM: Artificial Sequence
<220> FEATURE:
<223> OTHER INFORMATION: probe for 3'-UTR

<400> SEQUENCE: 487
ggtgcctcgt cgccgcagct                                                  20
```

IMAGING INDIVIDUAL MRNA MOLECULES USING MULTIPLE SINGLY LABELED PROBES

RELATIONSHIP TO PRIOR APPLICATIONS

This application is the U.S. National Phase of International Patent Application Ser. No. PCT/US09/56564, filed Sep. 10, 2009, which claims priority to a U.S. Provisional Patent Application Ser. No. 61/191,724, filed on Sep. 10, 2008, both of which are incorporated herein by reference in their entireties.

GOVERNMENT INTERESTS

The invention disclosed herein was made, at least in part, with Government support under Grant Nos. NIH GM-070357 and NIH MH-079197 from the National Institutes of Health. Accordingly, the U.S. Government has certain rights in this invention.

FIELD OF THE INVENTION

This invention generally relates to methods of nucleic acid sequence detection.

BACKGROUND

As it has become increasingly apparent that gene expression in individual cells deviates significantly from the average behavior of cell populations, new methods that provide accurate integer counts of mRNA copy numbers in individual cells are needed. Ideally, such methods should also reveal the intracellular locations of the mRNAs, as mRNA localization is often used by cells to spatially restrict the activity gene.

In situ hybridization, followed by microscopic analysis, is a well-established means of studying gene expression. The first generation of in situ hybridizations was performed with radioactive probes. Early improvements involved linking the probes to enzymes that catalyze chromogenic or fluorogenic reactions. However, because the products of these reactions were small molecules or precipitates that diffuse away from the probe, the location of the target molecules could not be precisely determined. Conversely, probes labeled directly with a few fluorophores maintained spatial resolution, but the sensitivity that can be achieved is relatively poor.

Robert Singer and colleagues developed an in situ hybridization procedure that was not only sensitive enough to permit the detection of single mRNA molecules, but also restricted the signals to close proximity of the targets. They hybridized five oligonucleotide probes simultaneously to each mRNA target, each of which was about 50-nucleotides in length and each of which was labeled with five fluorophore moieties. Although the authors convincingly demonstrated single molecule sensitivity and other groups have successfully used these probes, the system has not been widely adopted. One reason for this is difficulty in the synthesis and purification of heavily labeled oligonucleotides. Usually, flurophore moieties are introduced via primary amino groups that are incorporated into oligonucleotides during their synthesis. When multiple amino groups are introduced into the same oligonucleotide some are lost due to side reactions such as transamidation. Coupling of fluorophores to the remaining amino groups is inefficient and requires several consecutive coupling reactions and it is difficult to purify oligonucleotides in which all designed sites are coupled to fluorophores from those that are partially coupled. Also, when some fluorophores are present in multiple copies on the same oligonucleotide they interact with each other altering the hybridization characteristics of the oligonucleotides and exhibiting severe self-quenching. These problems are obviated if each probe had just a single terminal amino group to serve as the site of attachment.

Another issue with the use of small numbers of heavily labeled probes is that a significant portion of the fluorescence is lost for every probe that does not bind to the target, whereas every non-specific binding event increases the background. This leads to a widened distribution of number of probes bound to each target mRNA. For instance, when using 5 fluorescent probes targeted to a single mRNA, Femino et al estimated that the majority of the fluorescent spots observed had intensities indicating the presence of only 1 or 2 probes. *Science* 280, 585-590 (1998). This makes it difficult to unambiguously identify those fluorescent spots as mRNA molecules, since it is impossible to determine whether the detection of an individual probe arises from legitimate binding to the target mRNA or non-specific binding. These "thresholding" problems limit the ability of such methods to provide reliable counts of mRNA numbers in individual cells.

Thus there remains a need for improved methods to provide reliable counts of mRNA numbers in individual cells and a need for probes that are easily synthesized and purified.

SUMMARY OF THE INVENTION

This invention provides a method for detecting individual nucleic acid molecules, such as, for example, RNA molecules, e.g., mRNA molecules in fixed, permeabilized cells using a plurality of nucleic acid hybridization probes that are singly fluorescently labeled, as with the same fluorophore. The inventors have surprisingly discovered that if at least 30, preferably 40-60, and very preferably 48 different probes, all labeled with the same fluorophore, are hybridized simultaneously to a target sequence of an mRNA molecule, a fluorescent spot is created that can be detected from the combined fluorescences of the multiple probes. The probes are non-overlapping; that is, the region of the target sequence to which each probe hybridizes is unique (or non-overlapping). Probes in a set of 30 or more for a selected target sequence can be designed to hybridize adjacently to one another or to hybridize non-adjacently, with stretches of the target sequence, from one nucleotide to a hundred nucleotides or more, not complementary to any of the probes. Accordingly, in one aspect, the invention provides a method for probing a target sequence of nucleic acid molecules such as, for example, mRNAs in a fixed, permeabilized cell, said target sequence including at least 30 non-overlapping probe binding regions of 15-100 nucleotides, comprising immersing said cell in an excess of at least 30 nucleic acid hybridization probes, each singly labeled with the same fluorescent label and each containing a nucleic acid sequence that is complementary to a different probe binding region of said target sequence; washing said fixed cell to remove unbound probes; and detecting fluorescence from said probes.

Probes useful in this invention may be DNA, RNA or mixtures of DNA and RNA. They may include non-natural nucleotides, and they may include non-natural internucleotide linkages. Non-natural nucleotides that increase the binding affinity of probes include 2'-O-methyl ribonucleotides. The lengths of probes useful in this invention are 15-40 nucleotides for typical DNA or RNA probes of average binding affinity. Preferred lengths of DNA probes and RNA probes are in the range of 15-30 nucleotides, more preferably 17-25 nucleotides and even more preferably 17-22 nucleotides. The inventors have constructed the probes to be about 20 nucleotides long. If means are included to increase a probe's binding affinity, the probe can be shorter, as short as seven nucleotides, as persons in the art will appreciate. A fluorophore can be attached to a probe at any position, including, without limitation, attaching a fluorophore to one end of a probe, preferably to the 3' end. The probes may be included in a hybridization solution that contains the multiple probes in excess, commonly in the range of 0.2-1 nanograms per microliter. Sufficient solution is added to cover and wet the cell so that the cell is immersed in the probe-containing solution.

A single cell can be probed simultaneously for multiple mRNA target sequences, either more than one target sequence of one mRNA molecule, or one or more sequences of different mRNA molecules. Additionally, one target sequence of an mRNA molecule can be probed with more than one set of probes, wherein each set is labeled with a distinguishable fluorophore, and the fluorophores are distinguishable. For example, in probing a gene sequence, at least 30 green-labeled probes can be used to probe one portion of the gene sequence as its target sequence, and at least 30 red-labeled probes can be used to probe a different portion of the gene sequence as its target sequence. Using more than one color for each of multiple targets permits use of color-coding schemes in highly multiplexed probing methods according to this invention.

Methods of this invention may include simply looking to see if one or more spots representing a target sequence are present. Methods according to this invention also include counting spots of a given color corresponding to a given mRNA species. When it is desired to detect more than one species of mRNA, different sets of probes labeled with distinct fluorophores can be used in the same hybridization mixture. A gene expression profile for each species of mRNA is constructed by counting spots of different colors.

Spots can be detected utilizing microscopic methods. It is not necessary to use a confocal microscope, as a wide-field fluorescence microscope is sufficient. To distinguish spots that positively reflect a target sequence from dim spots that may reflect background fluorescence or nonspecific binding, methods according to this invention include detection. In one embodiment, the detection comprises filtering images with a three-dimensional linear Laplacian of Gaussian filter and applying a detection threshold. If one plots the number of spots in three dimensions for all thresholds ranging from zero to the maximum pixel intensity in the filtered image, there is a wide plateau, indicative of a region in which the number of spots detected is insensitive to threshold. Thus, the method further comprises plotting the number of spots, determining the boundaries of a plateau region, and selecting the threshold preferably within that region.

In another aspect, this invention includes sets of probes for in situ hybridization that enable detection of individual mRNA molecules in cells. The probes render each molecule so intensely fluorescent that it can be seen as a fine fluorescent spot in fluorescence microscopy.

A computer program can be used to identify and count all the mRNA molecules in the cell from the microscopic image. In situ hybridizations performed with the sets of probes described above allow accurate and simple gene expression analysis, detection of pathogens and pathogenic states such as cancer.

Accordingly, in another aspect, provided is a method of screening for compounds which alter the amount of a subcellular distribution of the target sequence. The method includes incubating a cell with a test compound for a period of time sufficient to elicit a response, detecting the amount of distribution pattern of the target sequence, and comparing this amount or distribution with an amount or distribution of the target mRNA in a control cell which was treated identically, but not incubated with the test compound.

In yet another aspect, the invention provides a computer readable medium, comprising instructions for: obtaining a 3-D stack of 2-D fluorescent images; filtering said 3-D stack using a 3-D filter; counting a total number of 3-D spots in said filtered 3-D stack for each of a plurality of intensity thresholds; obtaining an optimum intensity threshold representative of a plateau region in a plot of said total number of 3-D spots verses the intensity threshold at which said total number was counted; and using the total number of 3-D spots obtained at said optimum threshold as representative of a number of fluorescing particles detected in said 3-D stack.

The invention also provides a kit, generally comprising the set of probes and the computer-readable media as described above.

BRIEF DESCRIPTION OF THE DRAWINGS

FIG. 1A is a schematic depiction of the construct used. The 48 probes used to detect the GFP coding sequence were labeled with Alexa-594 and the four different probes used to detect the tandem repeat in the 3'-UTR were labeled with TMR. FIG. 1B illustrates maximum intensity merges of a pair of z-stack of fluorescent images of CHO cells taken in the Alexa-594 channel (left) and the TMR channel (right) corresponding to GFP coding region probes and UTR probes, respectively. FIG. 1C illustrates false color merge of the images in FIG. 1B enclosed by the red (GFP) and green (UTR) squares, with red circles representing computationally identified GFP mRNA particles, green circles representing UTR particles, and yellow circles representing co-localized particles. All scale bars are 5 μm long.

FIG. 3A illustrates spot intensity (defined as maximum intensity within the spot minus the mean background taken in an annular region surrounding the spot) as a function of the number of probes chosen. Intensities for 12 and 24 probes are artifactual in that spots were not readily identifiable in those cases, so spots identified were biased towards being brighter. FIG. 3B illustrates the number of spots (i.e., connected components) found upon thresholding the filtered image plotted as a function of the threshold value, ranging from 0 to the maximum intensity of the filtered image (normalized to 1) for different numbers of probes. The grey bar indicates the threshold used for the analysis in FIG. 3A.

FIG. 4A is a schematic depicting the method described in this manuscript with 48 singly labeled probes (left) and the method of Femino et al. in which each 45 bp probe contains five fluorophores each and is targeted to a sequence element that is repeated 32 times in the 3'UTR of the target mRNA expressed from a transgene in Chinese hamster ovary cells. FIG. 3B illustrates a comparison of spot intensities when using 48 singly labeled probes or using a 45 bp probe labeled with five fluorophores. Error bars represent one standard deviation.

FIG. 5A illustrates raw image data (maximum intensity merge) obtained from imaging FKBP5 mRNA particles in A549 cells induced with dexamethasone. FIG. 5B illustrates mage (maximum merge) obtained by running raw data through Laplacian of a Gaussian filter to enhance spots. FIG. 5C illustrates the number of spots (i.e., connected components) found upon thresholding the filtered image from FIG. 5B is plotted as a function of the threshold value, ranging from 0 to the maximum intensity of the filtered image (normalized to 1). FIG. 5D is an image showing the results of using the threshold represented by the grey line in FIG. 5C with each distinct spot assigned a random color. All scale bars are 5 µm long.

FIG. 6A-FIG. 6C illustrate images showing FLJ11127, Cox-2 and FKBP5 mRNA particles in the same set of A549 cells not treated with dexamethasone. FIG. 6D-FIG. 6F illustrate images showing FLJ11127, Cox-2 and FKBP5 particles in cells treated for 8 hours with 24 nM dexamethasone. FIG. 6G illustrates fold induction for all three genes as measured by FISH and realtime RT-PCR; error bars for FISH were obtained by bootstrapping and those for RTPCR were obtained by repetition as described in the supplementary information. All images are maximum merges of a z-stack of fluorescent images spanning the extent of the cells with nuclear DAPI counterstaining in purple, and all scale bars are 5 µm long.

FIG. 7A is an illustration of images of an FLJ11127 mRNA spot labeled with TMR as seen through the TMR, Alexa 594 and Cy5 filter channels. Linescans of fluorescent intensity corresponding to the line through the image are given below, with the different linescans corresponding to measurements taken at increasing z (0.25 µm spacing). The green linescan corresponds to the z-slice shown in the image itself. A similar analysis was performed for a Cox-2 mRNA spot labeled with Alexa 594 (FIG. 7B) and an FKBP5 mRNA particle labeled with Cy5 (FIG. 7C). All linescan intensity measurements had the camera background subtracted but range between 0 and 200 arbitrary fluorescence units.

FIG. 8A illustrates the mean of the maximum spot fluorescence for a number of FLJ11127 mRNAs labeled using TMR conjugated probes was plotted as a function of the number of 2 second exposures using a filter specific for TMR. Curves were generated for images taken both with (blue) and without (red) the oxygen scavenging system. A similar analysis was performed for Cox-2 mRNAs labeled using Alexa-594 conjugated probes with 2 second exposures (FIG. 8B) and FKBP5 mRNAs labeled using Cy5 conjugated probes with 2.5 second exposures (FIG. 8C). FIG. 8D illustrates the bleach rate per exposure (in units of fraction of fluorescence lost per exposure) for the TMR, Alexa-594 and Cy5 conjugates probes in (FIG. 8A-FIG. 8C) both with and without the oxygen-scavenging anti-bleach system. The bleach rate was calculated by fitting each individual particle's decay curve to an exponential and taking the mean of the fitted decay constants. The error bars correspond to one standard deviation. A minimum of 6 particles were chosen in each condition.

FIG. 9A is an illustration of elt-2 mRNA molecules (red) in an early stage embryo (~100 cell stage) from C. elegans; the nuclei have been counterstained with DAPI (blue). FIG. 9B is an illustration of elt-2 mRNA molecules in an L1 larva from C. elegans. Inside the blue box, a single focal plane is shown in which the intestinal track is visible. FIG. 9C illustrates a schematic depiction of dpp and engrailed expression in the imaginal wing discs of third instar larvae from D. melanogaster. FIG. 9D is an image showing the locations of the computationally identified dpp mRNA molecules (light blue circles) and Engrailed expression detected by immunofluorescence (dark blue). FIG. 9E is an image containing enhanced dpp mRNA molecule signals (light blue) and Engrailed protein expression detected by immunofluorescence (dark blue). All images except the boxed portion of FIG. 9B are maximum merges of a z-stack of fluorescent images, and all scale bars are 5 µm long.

FIG. 10A and FIG. 10B illustrate STL1 mRNA particles in both unperturbed cells (FIG. 10A) and cells subjected to a 10 minute 0.4M NaCl salt shock, with nuclear DAPI counterstaining in purple (FIG. 10B). FIG. 10C illustrates expression of β-actin (green) and Map2 (red) mRNAs in rat hippocampus neurons in a dissociated neuron culture. FIG. 10D illustrates an enlarged and contrasted image of a segment of a dendrite enclosed by the red box in FIG. 10C. All scale bars are 5 µm long.

FIG. 11A shows a 3'-UTR multimeric sequence (SEQ ID NO: 483) and probes (SEQ ID NOs: 484-487) used in the instant invention.

FIG. 11B shows sequences of β actin (SEQ ID NO: 1) and related probes (SEQ ID NOs: 2-49) used in the instant invention.

FIG. 11C shows sequences of COX2 (SEQ ID NO: 50) and related probes (SEQ ID NOs: 51-98) used in the instant invention.

FIG. 11D shows sequences of d2EGFP (SEQ ID NO: 99) and related probes (SEQ ID NOs: 100-147) used in the instant invention.

FIG. 11E shows sequences of dpp (SEQ ID NO: 148) and related probes (SEQ ID NOs: 149-196) used in the instant invention.

FIG. 11F shows sequences of elt-2 (SEQ ID NO: 197) and related probes (SEQ ID NOs: 198-245) used in the instant invention.

FIG. 11G shows sequences of FKBPS (SEQ ID NO: 246) and related probes (SEQ ID NOs: 247-306) used in the instant invention.

FIG. 11H shows sequences of FLJ11127 (SEQ ID NO: 307) and related probes (SEQ ID NOs: 308-360) used in the instant invention.

FIG. 11I shows sequences of Map2 (SEQ ID NO: 361) and related probes (SEQ ID NOs: 362-433) used in the instant invention.

FIG. 11J shows sequences of STL1(SEQ ID NO: 434) and related probes (SEQ ID NOs: 435-482) used in the instant invention.

DETAILED DESCRIPTION OF THE INVENTION

Figure 1:
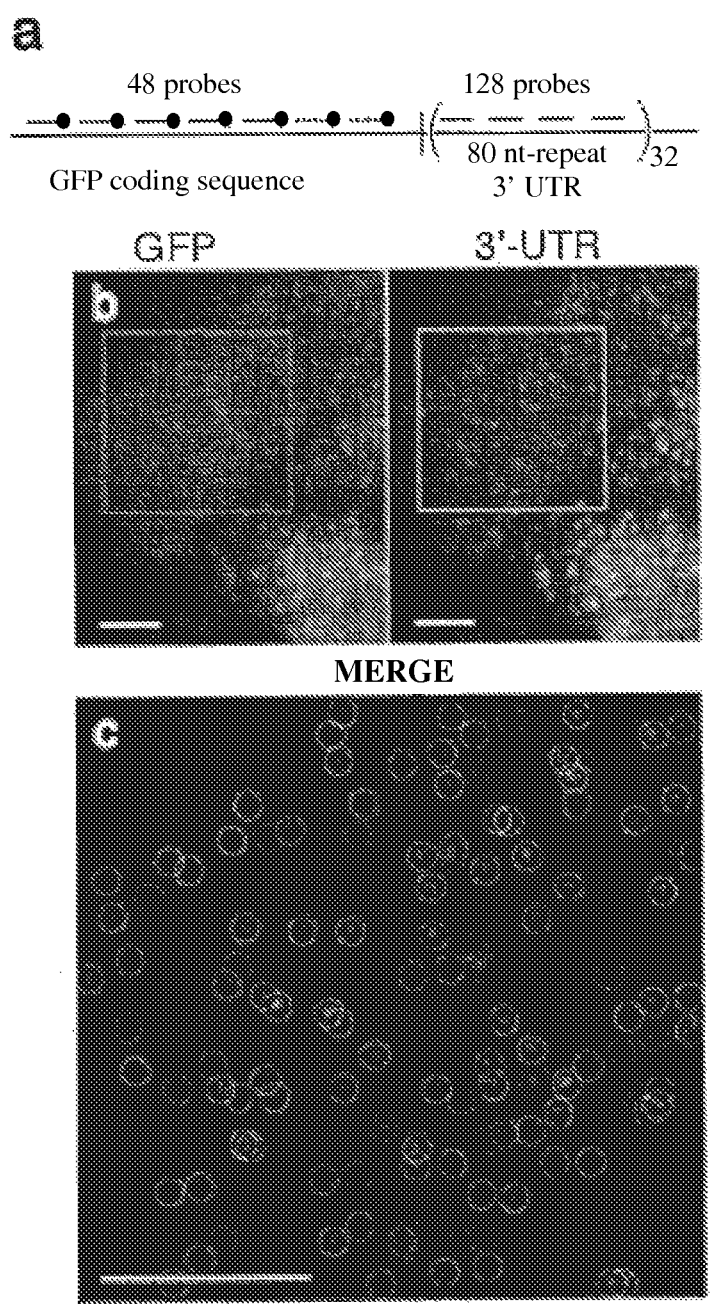
FIG. 1 shows simultaneous detection of a unique sequence and a repeated sequence in individual mRNA molecules.

This invention relates in part to the development of an image analysis algorithm that utilizes a principled thresholding strategy and shows that we can accurately and unambiguously identify and count all the target mRNA molecules present in the cell. The simplicity and robustness of this approach permits reliable detection of three different mRNA species within the same cells. Using a rigorous set of criteria the inventors have demonstrated that the method allows extremely specific single mRNA imaging across a wide spectrum of cell types and model organisms.

The inventors have taken advantage of the availability of 96 well DNA synthesizers to synthesize many different terminally labeled smaller probes for the same target. The obtained results show that when a set of at least 30, preferably at least 40, more preferably, about 48 (half of a 96-well plate that is used for high throughput DNA synthesis) or more singly labeled probes bind to the same mRNA molecule, they render it sufficiently fluorescent that it becomes visible as a diffraction-limited spot in wide-field microscopy. The non-specific sites only associate with one or a few probes, yielding diffused signals, whereas the legitimate targets bind to all or most of the probes yielding a clearly detectable spot for each mRNA molecule.

The inventors have also developed an image analysis algorithm that utilizes a principled thresholding strategy and shows that it is possible to accurately and unambiguously identify and count the all target mRNA molecules present in the cell. The simplicity and robustness of this approach permits reliable detection of three different mRNA species within the same cells. Using a rigorous set of criteria the inventors demonstrate that the method allows extremely specific single mRNA imaging across a wide spectrum of cell types and model organisms.

Thus, 48 or more singly labeled oligonucleotide probes allow the detection of individual mRNA molecules. The mRNA molecules were visualized as diffraction limited spots that can be easily detected in a standard wide-field microscopic set up. The spots were bright enough to be accurately counted with the spot detection image processing algorithm of the instant invention. The inventors obtained quantitative counts of three different species of mRNA molecules within individual cells. Such analysis facilitates accurate multiplex gene expression profiling of even lowly expressed genes across a host of model organisms.

The basis of specificity of the instantly disclosed system is that most or all of the probes bind to the intended target mRNA and yield a particulate signal whereas the non-specific binding sites elsewhere in the cell associate with fewer probe molecules and give a diffused signal that the spot counting algorithm ignores. This highlights a key advantage of the instant method over other in situ hybridization methods that use heavily labeled probes such as dendrimers. If every probe molecule is detectable, each non-specific binding event will result in a false positive and any mRNA to which the probe does not bind will result in a false negative. The likelihood of false negatives and positives decreases, however, as the number of probes is increased, and in general, given a certain efficiency of hybridization, increasing the number of different probes will narrow the distribution of probes bound per molecule. The image analysis according to the instant invention showed that increasing the number of the probes resulted in robust spot detection that does not depend on arbitrarily chosen thresholds. This is crucial for accurately counting the number of mRNAs per cell, which is a key feature of the method of the invention.

In a related point, a potential factor in the design of the probe set is uniformity in hybridization affinities. Since oligonucleotide affinity is largely dominated by its relative GC content, the inventors have created a computer program to design a set of probes with optimally uniform overall GC content. This computer program is publicly available.

From a practical standpoint, the instantly claimed method also yields significant benefits over previous single molecule mRNA FISH method both in terms of time and cost. Due to advances in synthesis, researchers can easily and cheaply purchase large numbers of oligonucleotides with 3' amine modifiers. These can then be pooled, coupled, and purified en-masse, significantly reducing the labor associated with the multiple couplings and purifications required to generate multiply labeled probe. The resulting simplicity and cost-effectiveness of the instant method will facilitate genomics-scale studies involving the detection of many different mRNAs. Furthermore, the flexibility of the hybridization procedure allows for it to be combined with other standard techniques, such as immunofluorescence.

In another embodiment, the fluorophores can be incorporated into the probes during automated DNA synthesis.

Other methods for quantifying the number of mRNAs in individual cells include single-cell RT-PCR and digital RT-PCR. One problem with these methods is the practical difficulties associated with assembling large numbers of individual reactions that require the use of microfluidic or robotic devices. Moreover, those methods suffer from concerns about stochastic variations in exponential amplification when the target inputs are just a few molecules. Such stochastic behavior complicates the analysis of single cell gene expression, which itself is subjected to stochastic forces. Moreover, these methods do not provide any information about the spatial location of the mRNAs.

Given the simplicity and broad applicability of our single-molecule mRNA detection method, such method is suitable for a variety of studies. By obtaining exact mRNA counts in individual cells, one can make accurate determinations of both expression differences in different conditions and the cell-to-cell variability in gene expression. By yielding quantitative, spatial measurements of individual mRNAs in single cells, this method is valuable in many studies in systems biology, cell biology, neurobiology and developmental biology.

Accordingly, this method may be utilized for multiple assays, including, without limitation a screening assay. In one embodiment, the screening assay determines whether a test compound affects an amount of a distribution of a target sequence of messenger ribonucleic acid molecules (mRNA's) said target sequence including at least 30 non-overlapping probe binding regions of 15-100 nucleotides in a cell. The assay generally comprises the following steps: incubating a cell with a test compound for a period of time sufficient to elicit a response; permeabilizing the cell; immersing said cell in an excess of at least 30 nucleic acid hybridization probes, each singly labeled with the same fluorescent label and each containing a nucleic acid sequence that is complementary to a different probe binding region of said target sequence; washing said fixed cell to remove unbound probes detecting an amount of a distribution of fluorescence from said probes, comparing said amount or said distribution with an amount of a distribution, respectively, obtained from a control cell, treated as described above, but with the exception of being incubated with the test compound.

Suitable test compound candidates include, without limitation, peptide-based compounds (e.g., antibodies or nanobodies), RNA interference agents (i.e., siRNA, shRNA, miRNA etc), and small molecules. All these compounds may be made according to the methods known in the art. For example Naito (US 20080113351) and Khvorova (US 20070031844) provide methods of selecting active RNA interference compounds. Antibodies may also be prepared by known techniques including the use of hybridomas, selection of monoclonal antibodies, use of phage display libraries, antibody humanization and the like.

Small molecule compounds may be selected from screening of the appropriate libraries. In one aspect, small molecule libraries are synthesized according to methods well known and routinely practiced in the art. See, for example, Thompson and Ellman, Chem. Rev. 1996, 96, 555-600, Shipps, et al., Proc. Natl. Acad. Sci. USA, Vol. 94, pp. 11833-11838, October 1997, and Combinatorial Library Design and Evaluation—Principles, Software Tools and Applications in Drug Discovery, Ghose and Viswanadhan (eds), Marcel Dekker 2001. Alternatively, small libraries are obtained from any of a number of sources including, for example, the NIH Molecular Libraries Small Molecule Repository. Alternative sources include AnalytiCon Discovery GmbH (Potsdam, Germany) which makes available MEGAbolite®, pure natural product small molecule libraries and NatDiverse™, semi-synthetic natural product analogue small molecule libraries; Quantum Pharmaceuticals Ltd. (Moscow, Russian Federation); and Praecis Pharmaceuticals Incorporated (Waltham, Mass.).

In yet another aspect, the invention provides software implementing the thresholding algorithm as described above. Thus, in one embodiment, provided is a computer readable medium, comprising instructions for: obtaining a 3-D stack of 2-D fluorescent images; filtering said 3-D stack using a 3-D filter; counting a total number of 3-D spots in said filtered 3-D stack for each of a plurality of intensity thresholds; obtaining an optimum intensity threshold representative of a plateau region in a plot of said total number of 3-D spots verses the intensity threshold at which said total number was counted; and using the total number of 3-D spots obtained at said optimum threshold as representative of a number of fluorescing particles detected in said 3-D stack.

In one embodiment, the thresholding is accomplished using three dimensional linear Laplacian of Gaussian filter.

In another aspect, a kit is provided. The kit comprises a computer-readable media implementing the thresholding algorithm, as described above, and a set of probes against a pre-selected target sequence. The probes described in connection with the claimed method are also suitable for the instant kit.

Specific embodiments according to the methods of the present invention will now be described in the following examples. The examples are illustrative only, and are not intended to limit the remainder of the disclosure in any way.

EXAMPLES

Example 1

Materials and Methods

The procedures described in this section are applicable to all examples unless indicated otherwise.

Probe Design

The sets of probes were designed to consist of at least 48 oligonucleotides each with lengths varying from 17 to 22 nucleotides long with a 3'-amine modification (FKBP5, FLJ11127, and Map2 mRNAs were probed using 63, 53 and 72 oligonucleotides respectively). Additionally, the GC content of the oligonucleotides was kept close to 45% when possible. The oligonucleotides were pooled and coupled to a fluorophore in a single reaction, after which the uncoupled oligonucleotides and remaining free fluorophores were removed by HPLC purification.

Fluorescence in situ Hybridization

In preparation for FISH, all samples were fixed with 3.7% formaldehyde and permeabilized with ethanol. The hybridization was performed using buffers and conditions similar to those outlined by Femino et al., with the key difference being the stringency of the hybridization, which was lowered by reducing the amount of formamide used to 10%. The concentration of the probe that gave optimal signal was determined empirically.

Imaging and Data Analysis

All images were acquired using a standard wide-field fluorescence microscope. Computer-aided detection and counting of particles was performed with linear filters designed for enhancing particulate signals.

Example 2

Probing Repeated and Unique Sequences Present in the Same mRNA Molecule

Utilizing small oligonucleotide probes labeled with a single fluorophore moiety, the inventors have shown that individual mRNA molecules that were engineered to contain 32-96 tandem copies of a probe-binding sequence can be detected by in situ hybridization. The inventors also demonstrated that the individual spots in the image represent single mRNA molecules, utilizing a number of different approaches, including correlating the average mRNA copy number obtained by directly counting the diffraction-limited spots to a measurement of the number of target molecules obtained by real-time RT-PCR. Thus, if many different probes are utilized, each targeted to a distinct region of a natural mRNA, it would be possible to obtain single-molecule sensitivity without resorting to the use of engineered genes.

For the initial test of this hypothesis, the inventors constructed a doxycycline-controlled gene that produced an mRNA encoding green fluorescent protein and possessed 32 tandemly repeated 80 nucleotide-long sequences in its 3'-UTR; and then this engineered gene was stably integrated into the genome of a Chinese hamster ovary cell line. The mRNA expressed from this gene was probed simultaneously with 48 different oligonucleotides, each complementary to a unique region in the coding sequence, and a set of four oligonucleotides, each having a complementary sequence in the repeated motif (a total of 128 probes bound) (FIG. 1A). Each oligonucleotide in the probe set that was specific for the coding sequence was labeled with a single Alexa-594 fluorophore, and each oligonucleotide in the set specific for the repeat sequence was labeled with a single tetramethylrhodamine (TMR) fluorophore. The use of appropriate filter sets ensured that the fluorescence emitted from TMR fluorophores was not detected in the Alexa-594 channel and vice versa, as described below.

After performing FISH with these probes, the inventors have found that many "particles" with a diameter of about 0.25 micrometers were visible in both the TMR and Alexa-594 channels (FIG. 1B). The particles were identified computationally using an image processing program (described in the next section) that categorizes the particles as being labeled with either the GFP-coding-sequence probes (TMR), the UTR-specific probes (Alexa-594), or both (FIG. 1C). Upon identifying and localizing particles in four fields of view similar to the ones shown in FIG. 1c, a total of 599 particles corresponding to GFP-coding sequence-specific probes and 565 particles corresponding to the UTR-specific probes were counted. Of these particles, 85% of the "UTR particles" co-localized with the "GFP particles," whereas 81% of the GFP particles co-localized with the UTR particles. The high degree of co-localization between particles detected by the previously established tandem repeat detection method and the particles detected via simultaneous probing with 48 different singly-labeled oligonucleotides demonstrates the validity of using multiple single-labeled probes for the detection of endogenous transcripts. The fraction of particles that did not display co-localization likely correspond to mRNA molecules that lost either their coding sequence or their 3'-UTR in the natural processes of mRNA degradation.

Figure 2:
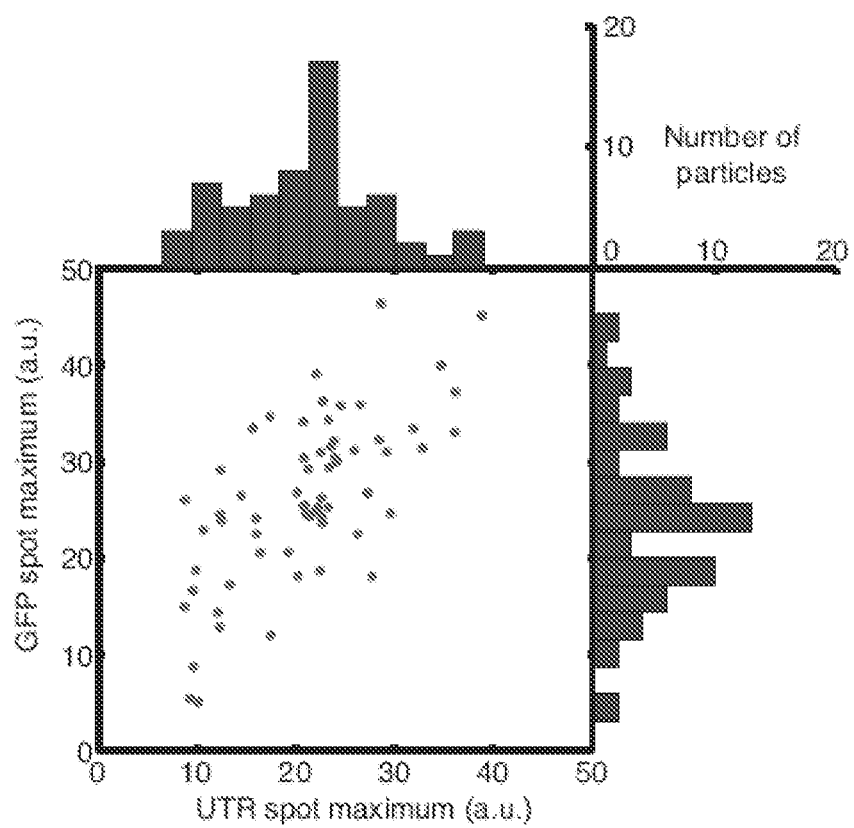
FIG. 2 shows intensity analysis of colocalized spots. Spot intensities corresponding to the GFP-targeted probes (Alexa 594 channel, y axis) and multimeric UTR-targeted probes (TMR channel, x axis) were computed by taking the maximum intensity in the computationally identified spot region and subtracting the mean intensity of an annular region surrounding the spot. Marginal histograms show the distributions of GFP spot intensities (right) and UTR spot intensities (top).
Figure 3:
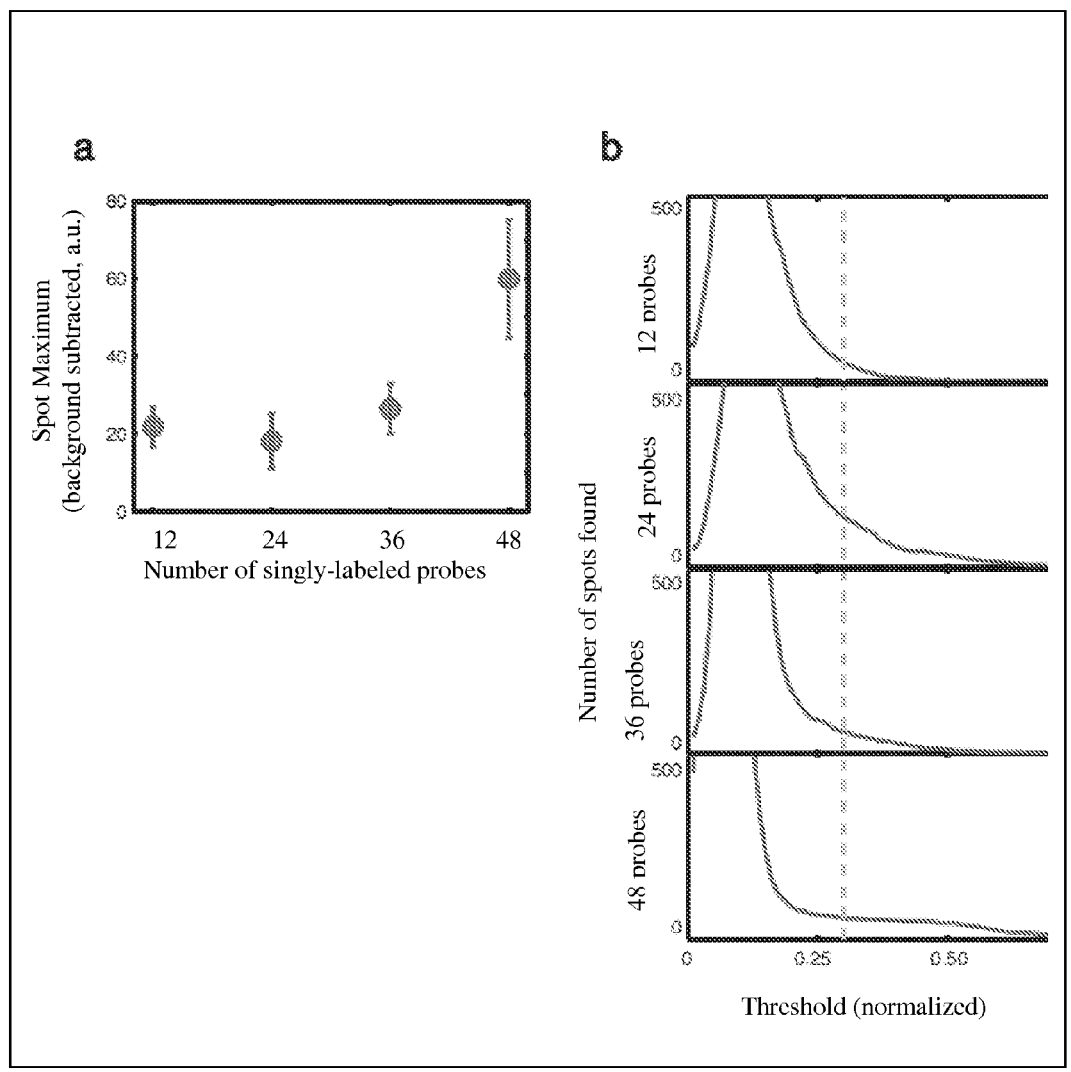
FIG. 3 shows sensitivity of method when using different numbers of probes.

The inventors also analyzed the fluorescent intensity of the co-localized spots in both the TMR and Alexa-594 channel and found that the spot intensities displayed a unimodal distribution (FIG. 2), arguing that the particles detected are not clumps of many mRNAs but rather individual molecules. The spot intensities displayed a strong correlation between the two channels (FIG. 3). Since there is no cross talk between the two channels, this indicates that the variability in spot intensity was not primarily due to random variability in probe hybridization (which would be uncorrelated between different probe sets) but rather other factors, such as mRNA integrity or accessibility, that affect both probes equally.

Figure 4:
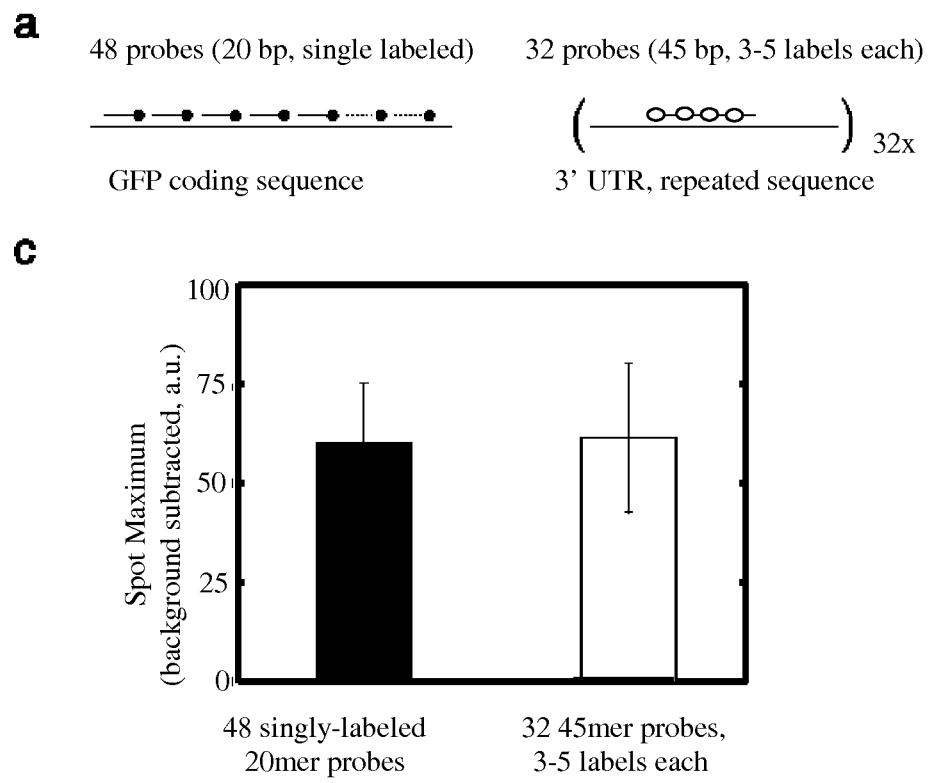
FIG. 4 shows comparison with the mRNA detection method of Femino et al. (Science 1998).

The inventors also explored how the signal intensity would vary with the number of probes by performing in situ hybridization using either first 12, 24, 36 probes or all 48 probes in the set. For this particular target mRNA, it was found that particles could be detected with fewer numbers of probes, albeit with decreased intensity (FIG. 3A). However, the automatic spot detection algorithm (described in details below) performed particularly well with 48 probes, detecting the same number of spots over a broad range of thresholds (FIG. 3B, see further discussion below). The number of probes required for robust signal is likely to depend on the target sequence, though, as the inventors have obtained clear mRNA signals using as few as 30 probes. When the instant method was compared to the method of Femino et al. by using a 45 bp long oligonucleotide labeled with 5 fluorophores and complementary to a sequence repeated 32 times in the 3'UTR of a gene, potentially yielding 160 fluorophores per mRNA (FIG. 4A), it was found that the signal to background were about the same in both methods (FIG. 4B), indicating that the instantly claimed method is at least as sensitive despite using fewer fluorophores.

Moreover, CHO cells lacking the reporter gene yielded no signals while CHO cells having the reporter gene that was turned off by addition of doxycycline, yielded mRNA particles in only a few cells, indicating that the signals observed were specific.

Example 3

Computational Algorithm for Spot Detection

Figure 5:
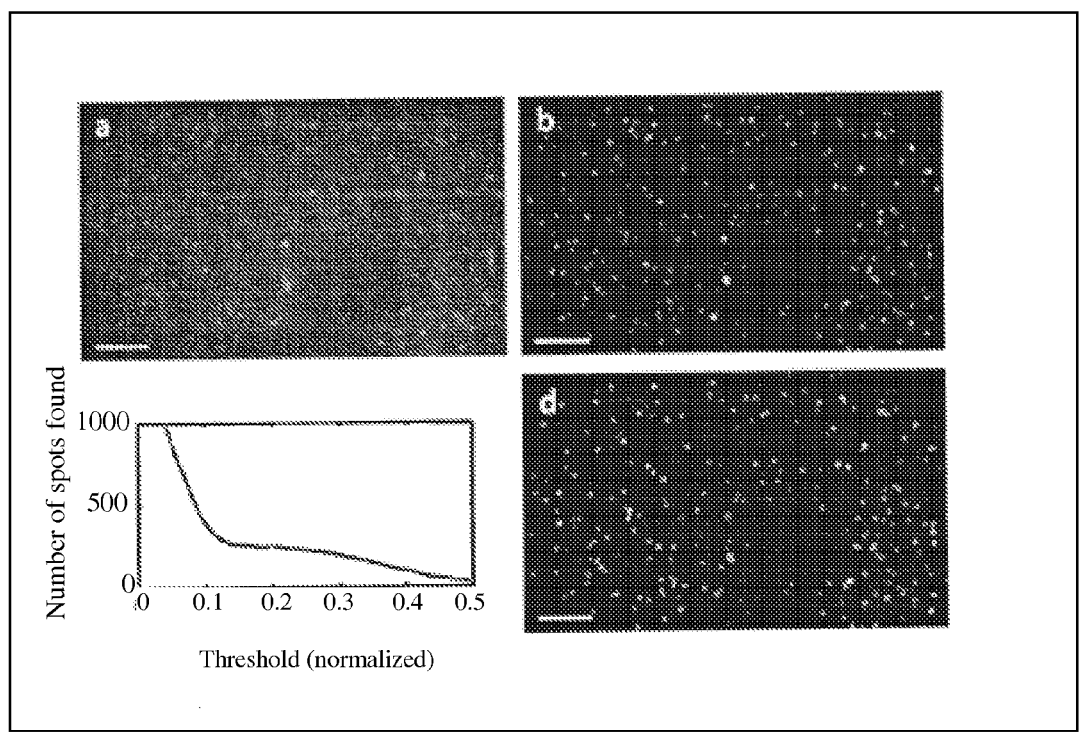
FIG. 5 shows computational identification of mRNA spots.
Figure 6:
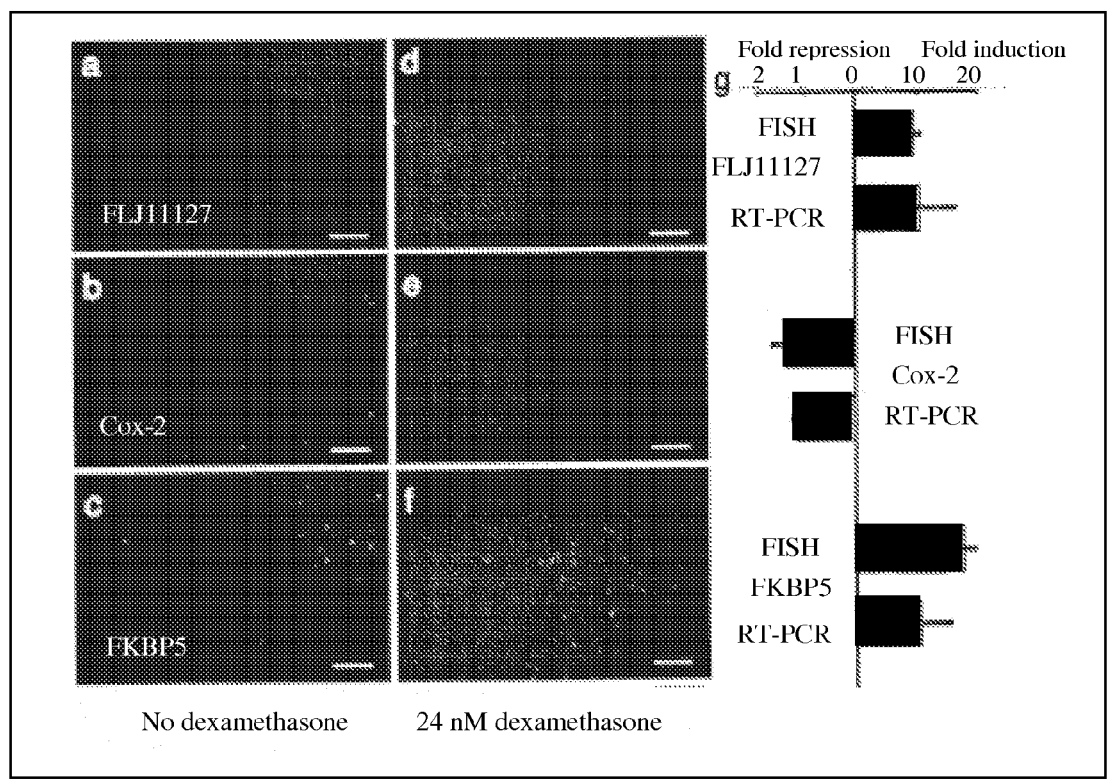
FIG. 6 shows simultaneously imaging single molecules of three different mRNAs in mammalian cells.

In order to reliably identify large numbers of mRNA molecules, the inventors developed a semiautomated computational algorithm for finding spots in a three-dimensional stack of fluorescent images. One of the difficulties associated with spot detection is the nonuniform background arising from cellular autofluoresence and low levels of non-specific probe hybridization. To circumvent these issues, the inventors filtered image stacks using a three dimensional linear Laplacian of Gaussian filter designed to enhance spot-like signals of the correct size and shape (FIG. 5A and FIG. 5B) while removing the slowly varying background. In the next step in the algorithm, the inventors applied a threshold to the filtered image in order to define the spots. In order to make a rational choice of threshold, the number of spots in three dimensions for all thresholds ranging from zero to the maximum pixel intensity in the filtered image was counted. When the inventors plotted the number of particles as a function of the threshold, a wide plateau was found, indicating that there is a region over which the number of particles detected is fairly insensitive to the particular threshold chosen (FIG. 5C). When a threshold in this region is chosen, the spots detected correspond very well with those identified by eye, demonstrating the efficacy of the spot detection algorithm (FIG. 5D).

Example 4

Gene Expression Profiling of Three Different mRNA Species

Figure 7:
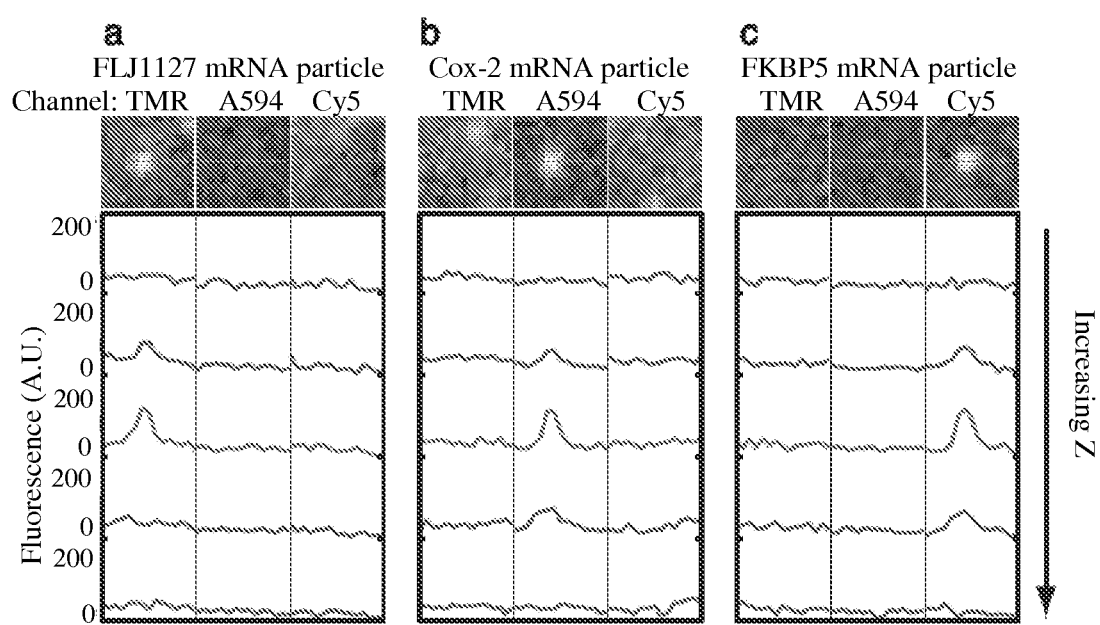
FIG. 7 shows examination of fluorescent spot bleedthrough.

A potential use of the instantly claimed method is the simultaneous detection of single molecules of multiple mRNAs in individual cells. To demonstrate this capability, the inventors designed probes specific to three mRNAs encoding FK506 binding protein 5 (FKBP5), Cox-2 and FLJ11127 in the human carcinoma cell line A549. These probes were coupled to the spectrally distinct fluorophores Cy5, Alexa 594 and TMR, respectively. Upon performing FISH with all three probes simultaneously, individual spots were visible in the three different fluorescence channels (FIG. 6A-FIG. 6F); an intensity analysis showed that fluorescent spots did not bleed through into other channels (FIG. 7).

To demonstrate that the claimed method of mRNA detection was specific and quantitative, the cells were incubated with the cell-permeable glucocorticoid dexamethasone, thus upregulating the expression of FKBP5 and F111127 while mildly downregulating the expression of Cox-2 in this particular cell-line. The inventors found that the mean number of FKBP5 and F111127 mRNAs measured by combining FISH with the instantly disclosed spot detection algorithm increased while the mean number of Cox-2 mRNAs decreased (compare FIG. 6A-FIG. 6C to FIG. 6D-FIG. 6F). These numbers corresponded well to RT-PCR measurements of the fold induction and repression of these genes performed on the same samples, demonstrating that the fluorescent spots are the appropriate mRNAs and that a majority of the mRNA molecules (FIG. 6G) was detected using the instantly claimed methods. Moreover, this further demonstrates the effectiveness of the spot detection method for accurate gene expression quantification.

Figure 8:
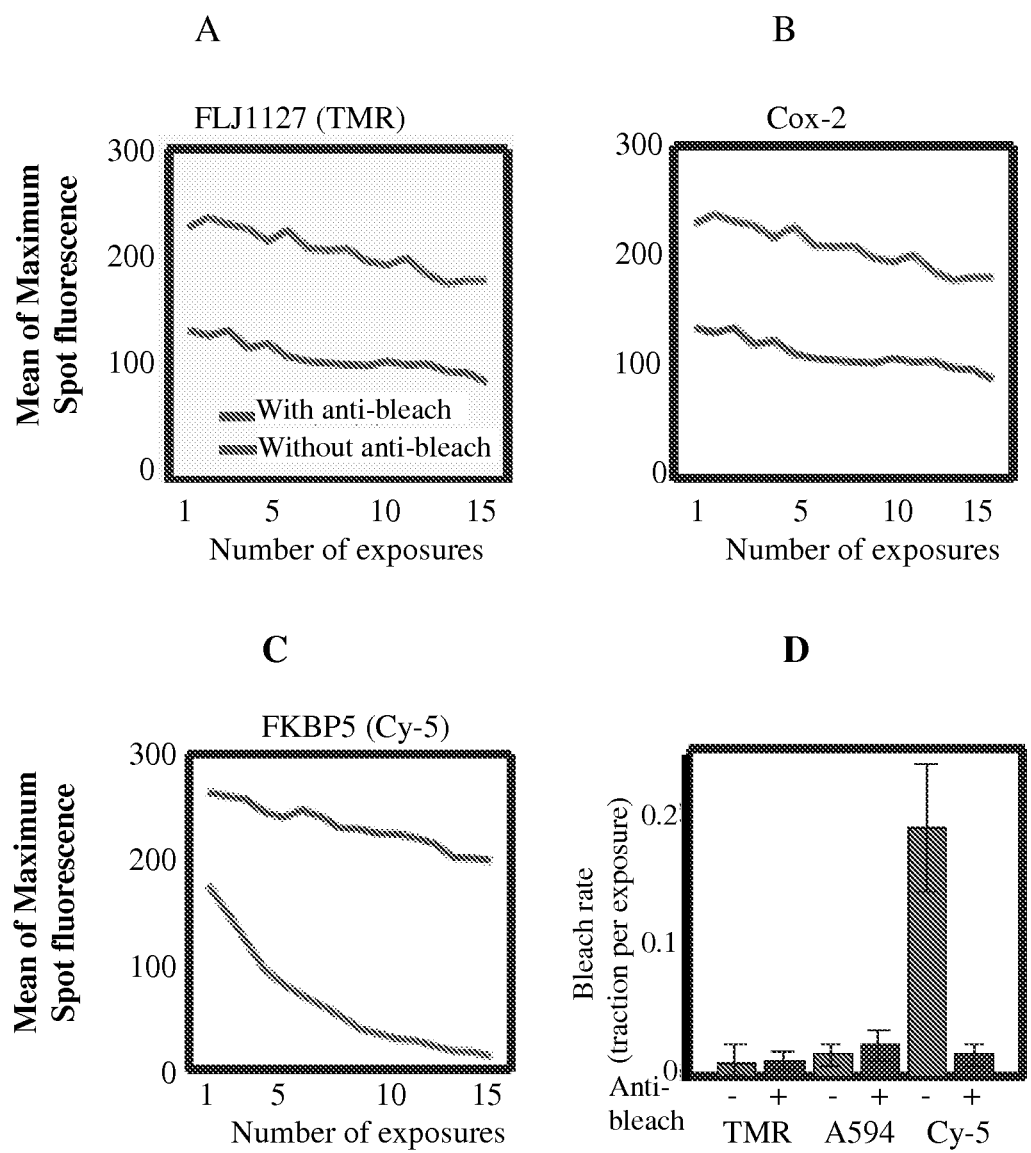
FIG. 8 shows demonstration that the oxygen-scavenger increases photostability of Cy5.

One technical challenge that arose in imaging multiple mRNAs simultaneously was fluorophore photolability, particularly in the case of Cy5. In order to image all of the mRNA molecules within a single cell, 10 to 30 "z-section" images for each visual field were acquired, utilizing a one-to-three second exposure for each image and a high numerical aperture objective. Only TMR and (to a lesser extent) Alexa-594 could withstand this intense and relatively prolonged exposure to light; Cy5, for instance, proved extremely photolabile under these conditions (FIG. 8). To overcome this problem, the inventors employed a special mounting medium in which fluorophores are much more photostable. This method was adapted from Yildiz et al. with minor modifications. In this medium, a mixture of catalase, glucose oxidase, and glucose enzymatically removes molecular oxygen from the medium, thereby inhibiting oxygen-dependent, light-initiated pathways that destroy fluorophores. The use of these enzymes lead to a dramatic 10-fold enhancement of Cy5 photostability while not adversely affecting the imaging of TMR and Alexa-594, thus facilitating the acquisition of multiple z-sections when performing three color imaging.

Example 5 mRNA Detection in Model Organisms and Cell Types

Figure 9:
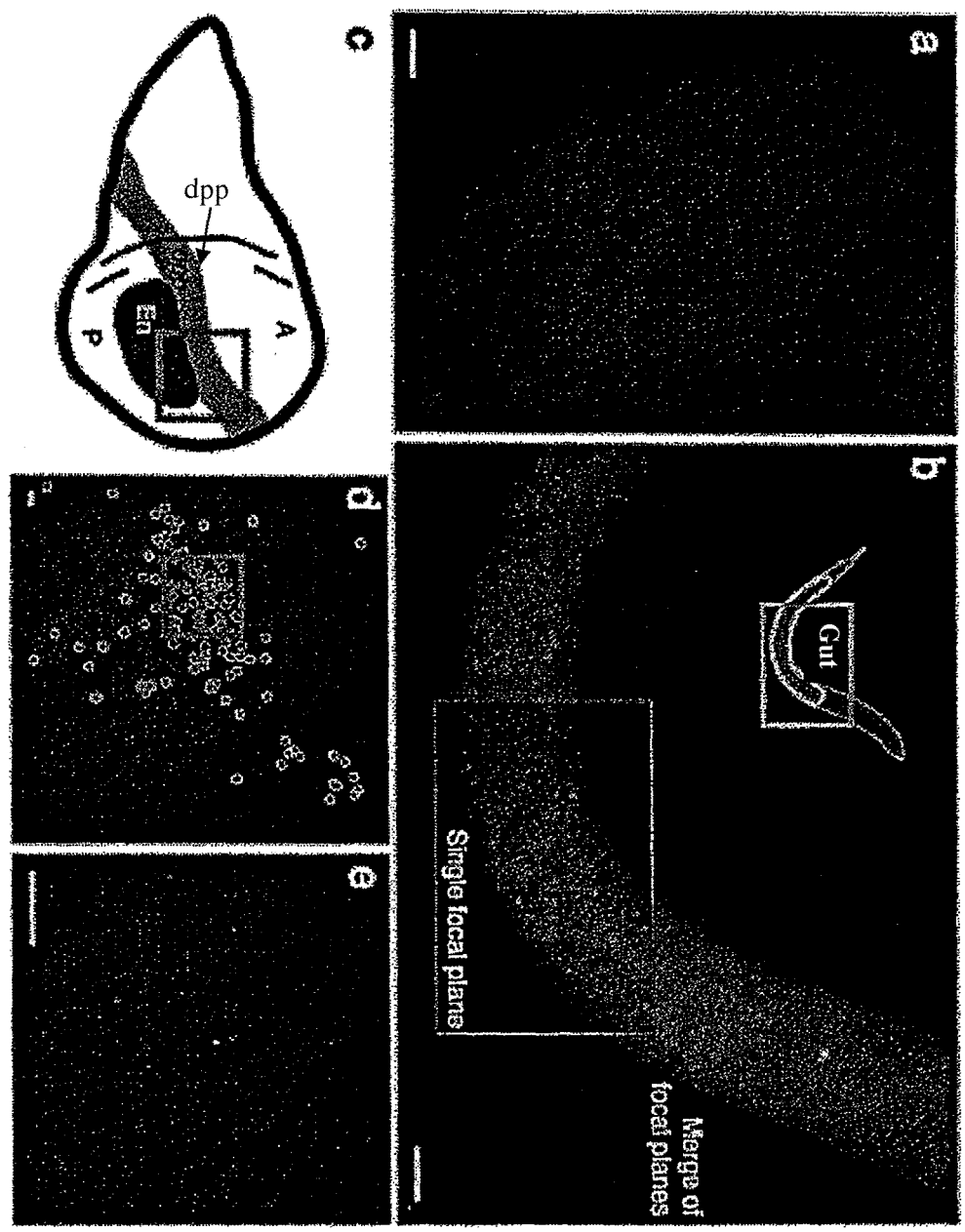
FIG. 9 shows imaging localized mRNAs in C. elegans and D. melanogaster.

One of the canonical uses for in situ hybridization has been for the detection of mRNA localization during development. The inventors tested the instantly claimed method for efficacy in two commonly studied developmental systems: the nematode, *Caenorhabditis elegans*, and the fruit fly, *Drosophila melanogaster*. In the nematode, the inventors constructed probes to detect mRNA molecules from the gene elt-2, a transcription factor that is expressed only in the nematode gut, and only after the nematode embryo has developed to the 45-cell stage. After hybridization of the probe set to both embryos and larvae, it was found that elt-2 mRNA molecules were present only within the gut region (FIG. 9A) of both the embryos and the larvae (FIG. 9B). However, consistent with the known timing of the onset of expression, elt-2 mRNAs were only detected in the gut of embryos older than the 45-cell stage, again highlighting the specificity of the instantly claimed method. Furthermore, at those early stages, only a few transcripts were detected, showing that this method is sensitive enough to detect even small numbers of transcripts in complex tissues.

In the fruit fly, one of the most well-studied examples of the localization of gene expression occurs in wing imaginal disc development. The wing discs of fruit fly larvae display a remarkable set of gene expression patterns, one of which is the formation of a stripe of expression of the gene dpp in response to gradients of the proteins Hedgehog and Engrailed. In particular, Engrailed, which negatively regulates dpp mRNA synthesis, is high in the posterior compartment of the wing disc and low in the anterior compartment of the wing disc. Similarly, Hedgehog, which positively regulates dpp mRNA synthesis, is high in the posterior compartment of the wing disc and low in the anterior compartment of the wing disc. However, there is a region between the posterior and the anterior where the levels of Hedgehog is high enough to activate dpp but not high enough to activate engrailed, resulting in the synthesis of dpp mRNA in a narrow stripe (FIG. 9C).

To check whether this narrow stripe of dpp mRNA synthesis can be imaged, the inventors constructed a set of singly labeled probes against dpp mRNA and performed in situ hybridization on imaginal wing discs isolated from third-instar larvae. Moreover, this in situ procedure was combined with immunofluorescence against Engrailed protein (shown in blue). FIG. 9D shows a full image, in which the locations of the algorithmically identified mRNA molecules are presented as blue circles; and FIG. 9E shows an enlarged portion of the image with enhanced mRNA signals.

The images show that mRNA molecules were found only at the anterior edge of the area of Engrailed expression, again confirming the specificity of detection.

Figure 10:
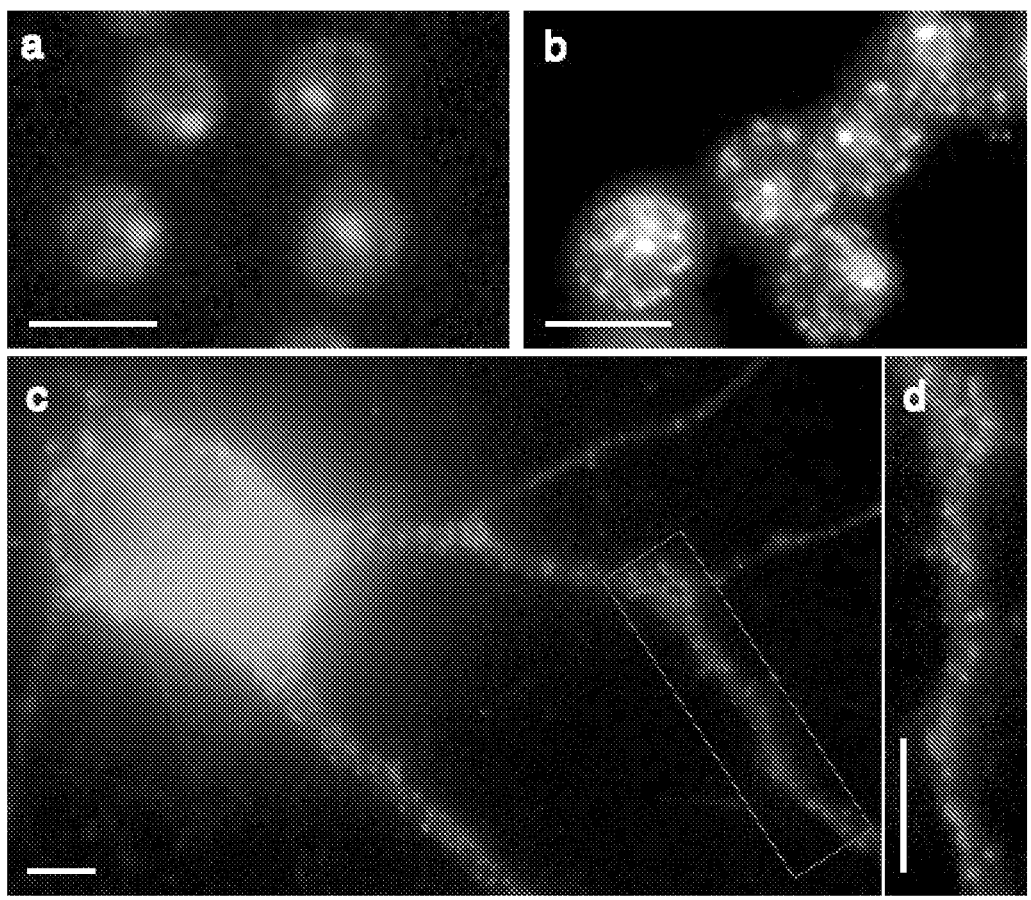
FIG. 10 shows imaging single mRNA molecules in yeast and neurons.

The inventors also tested the instantly claimed method in *Saccharomyces cerevisae* by designing a set of probe to target transcripts from the gene STU. STL1 is one among a number of yeast genes whose expression is significantly up-regulated by the addition of salt to the growth medium. It was found that non-shocked cells contain virtually no STL1 mRNA molecules (FIG. 10A), while cells subjected to a ten minute 0.4 M salt shock possessed a large numbers of STL1 mRNA molecules (FIG. 10B).

Another cell type in which mRNA localization is commonly studied is neurons. To show efficacy of the instantly claimed method in that system the inventors imaged β-actin mRNA and Map2 mRNA in cultured hippocampal neurons. FIG. 10C shows that a β-actin probe set (labeled with TMR) and a differently colored Map2 probe set (labeled with Alexa-594) can be used to image and distinguish their targets with a single molecule resolution. A fraction of these mRNAs migrate to distant reaches of dendrites (FIG. 10D). Particle counts indicated that 14% of the 791 β-actin mRNA molecules were located in dendrites, whereas 37% of the 140 Map2 mRNA molecules were located in the dendrites, which is similar to the previously reported distributions.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

References

1. Kaufmann, B. B. & van Oudenaarden, A. Stochastic gene expression: from single molecules to the proteome. *Curr Opin Genet Dev* 17, 107-112 (2007).
2. St Johnston, D. Moving messages: the intracellular localization of mRNAs. *Nat Rev Mol Cell Biol* 6, 363-375 (2005).
3. Gall, J. G. Differential synthesis of the genes for ribosomal RNA during amphibian oogenesis. *Proc Natl Acad Sci USA* 60, 553-560 (1968).
4. Levsky, J. M. & Singer, R. H. Fluorescence in situ hybridization: past, present and future. *J Cell Sci* 116, 2833-2838 (2003).
5. Tautz, D. & Pfeifle, C. A non-radioactive in situ hybridization method for the localization of specific RNAs in Drosophila embryos reveals translational control of the segmentation gene hunchback. *Chromosoma* 98, 81-85 (1989).
6. Raap, A. K. et al. Ultra-sensitive FISH using peroxidase-mediated deposition of biotin- or fluorochrome tyramides. *Hum Mol Genet* 4, 529-534 (1995).
7. Femino, A. M., Fay, F. S., Fogarty, K. & Singer, R. H. Visualization of single RNA transcripts in situ. *Science* 280, 585-590 (1998).
8. Tsokas, P. et al. Local protein synthesis mediates a rapid increase in dendritic elongation factor 1A after induction of late long-term potentiation. *J Neurosci* 25, 5833-5843 (2005).
9. Maamar, H., Raj, A. & Dubnau, D. Noise in gene expression determines cell fate in *Bacillus subtilis*. *Science* 317, 526-529 (2007).

10. Femino, A. M., Fogarty, K., Lifshitz, L. M., Carrington, W. & Singer, R. H. Visualization of single molecules of mRNA in situ. *Methods Enzymol* 361, 245-304 (2003).

11. Randolph, J. B. & Waggoner, A. S. Stability, specificity and fluorescence brightness of multiply-labeled fluorescent DNA probes. *Nucleic Acids Res* 25, 2923-2929 (1997).

12. Sindelar, L. E. & Jaklevic, J. M. High-throughput DNA synthesis in a multichannel format. *Nucleic Acids Res* 23, 982-987 (1995).

13. Vargas, D. Y., Raj, A., Marras, S. A., Kramer, F. R. & Tyagi, S. Mechanism of mRNA transport in the nucleus. *Proc Natl Acad Sci USA* 102, 17008-17013 (2005).

14. Raj, A., Peskin, C. S., Tranchina, D., Vargas, D. Y. & Tyagi, S. Stochastic mRNA synthesis in mammalian cells. *PLoS Biol* 4, e309 (2006).

15. Garneau, N. L., Wilusz, J. & Wilusz, C. J. The highways and byways of mRNA decay. *Nat Rev Mol Cell Biol* 8, 113-126 (2007).

16. Gonzalez, R. C., Woods, R. E. & Eddins, S. L. Digital Image Processing Using Matlab. (Pearson Prentice Hall, Upper Saddle River, N.J.; 2004).

17. Wang, J. C. et al. Chromatin immunoprecipitation (ChIP) scanning identifies primary glucocorticoid receptor target genes. *Proc Natl Acad Sci USA* 101, 15603-15608 (2004).

18. Yildiz, A. et al. Myosin V walks hand-over-hand: single fluorophore imaging with 1.5-nm localization. *Science* 300, 2061-2065 (2003).

19. Benson, D. M., Bryan, J., Plant, A. L., Gotto, A. M., Jr. & Smith, L. C. Digital imaging fluorescence microscopy: spatial heterogeneity of photobleaching rate constants in individual cells. *J Cell Biol* 100, 1309-1323 (1985).

20. Lecuyer, E. et al. Global analysis of mRNA localization reveals a prominent role in organizing cellular architecture and function. *Cell* 131, 174-187 (2007).

21. Fukushige, T., Hawkins, M. G. & McGhee, J. D. The GATA-factor elt-2 is essential for formation of the *Caenorhabditis elegans* intestine. *Dev Biol* 198, 286-302 (1998).

22. Sanicola, M., Sekelsky, J., Elson, S. & Gelbart, W. M. Drawing a stripe in *Drosophila* imaginal disks: negative regulation of decapentaplegic and patched expression by engrailed. *Genetics* 139, 745-756 (1995).

23. Rep, M., Krantz, M., Thevelein, J. M. & Hohmann, S. The transcriptional response of *Saccharomyces cerevisiae* to osmotic shock. Hot1p and Msn2p/Msn4p are required for the induction of subsets of high osmolarity glycerol pathwaydependent genes. *J Biol Chem* 275, 8290-8300 (2000).

24. Tiruchinapalli, D. M. et al. Activity-dependent trafficking and dynamic localization of zipcode binding protein 1 and beta-actin mRNA in dendrites and spines of hippocampal neurons. *J Neurosci* 23, 3251-3261 (2003).

25. Blichenberg, A. et al. Identification of a cis-acting dendritic targeting element in MAP2 mRNAs. *J Neurosci* 19, 8818-8829 (1999).

26. Warren, L., Bryder, D., Weissman, I. L. & Quake, S. R. Transcription factor profiling in individual hematopoietic progenitors by digital RT-PCR. *Proc Natl Acad Sci USA* 103, 17807-17812 (2006).

The invention claimed is:

1. A method for detecting individual RNA molecules containing a first target sequence in a fixed and permeabilized cell, said first target sequence including at least 12 different non-overlapping probe-binding regions 7-40 nucleotides long, comprising
providing a first set of hybridization probes consisting of DNA, RNA or a mixture of DNA and RNA free of non-natural nucleotides that increase binding affinity of probes, that are complementary to the probe-binding regions of said first target sequence and that are singly labeled with the same first fluorophore, said first set containing at least twelve different non-overlapping hybridization probes that have sequences complementary to the at least 12 different probe-binding regions of said first target sequence respectively;
fixing and permeabilizing the cell;
probing said molecules in the fixed, permeabilized cell with an excess of the first set of hybridization probes, whereby individual RNA molecules in the cell are rendered sufficiently fluorescent to be seen as spots of said first fluorophore in fluorescence microscopy;
washing said cell to remove unbound probes; and
detecting said spots of the first fluorophore by fluorescence microscopy, wherein the first set of hybridization probes are 7-30 nucleotides in length.

2. The method of claim 1 wherein the RNA molecules are mRNA molecules.

3. The method of claim 1 wherein the step of detection includes counting said spots.

4. The method of claim 1 wherein said first target sequence includes at least 30 probe-binding regions and said first set of probes includes at least 30 different probes.

5. The method of claim 4 wherein the RNA molecules contain a second target sequence having at least 30 different non-overlapping probe-binding regions 7-40 nucleotides long, wherein the step of providing includes providing a second set of hybridization probes that are complementary to the probe-binding regions of the second target sequence, are 7-30 nucleotides in length, and are each singly labeled with the same second fluorophore distinguishable from said first fluorophore, said second set containing at least 30 different non-overlapping hybridization probes that have sequences complementary to the at least 30 different probe-binding regions of the second target sequence, respectively; wherein the step of probing includes probing said molecules with an excess of the second set of hybridization probes, whereby individual RNA molecules in the cell are rendered sufficiently fluorescent to be seen as spots in fluorescence microscopy; and wherein the step of detecting includes detecting spots of said second fluorophore by fluorescence microscopy.

6. The method of claim 1 wherein said first target sequence includes 40-60 different probe-binding regions and said first set of probes consists of 40-60 different probes.

7. The method of claim 2 wherein said first target sequence is a coding sequence.

8. The method of claim 1 wherein the step of detecting includes imaging to show said spots of the first fluorophore, processing the image to enhance the spots, and detecting the spots utilizing a selected intensity threshold at which the number of spots is insensitive to threshold value.

9. The method of claim 8 wherein the selected intensity threshold is obtained by filtering the images, counting spots for each of a plurality of intensity thresholds, determining a plateau region for the total number of spots as a function of intensity threshold, at which the total number of spots is relatively insensitive to the threshold, and selecting the intensity threshold from within the plateau region.

10. The method of claim 9 wherein filtering the images comprises filtering a 3-D stack of 2-D images.

11. The method of claim 10 wherein filtering utilizes a three-dimensional linear Laplacian of Gaussian filter.

12. The method of claim 8 wherein detecting is quantitative.

13. The method of claim 1 wherein the RNA molecules contain a second target sequence having at least 12 different non-overlapping probe-binding regions 7-40 nucleotides long, wherein the step of providing includes providing a second set of hybridization probes that are complementary to the probe-binding regions of the second target sequence, are 7-30 nucleotides in length, and are each singly labeled with the same second fluorophore distinguishable from the first fluorophore, said second set containing at least twelve different non-overlapping hybridization probes that have sequences complementary to the at least 12 different probe-binding regions of the second target sequence, respectively; wherein the step of probing includes probing said molecules with an excess of the second set of hybridization probes, whereby individual RNA molecules in the cell are rendered sufficiently fluorescent to be seen as spots in fluorescence microscopy; and wherein the step of detecting includes detecting said spots of said second fluorophore by fluorescence microscopy.

14. A method for determining whether a test compound affects an amount of distribution in a cell of a first RNA target sequence having at least 12 different non-overlapping probe-binding regions 7-40 nucleotides long, comprising incubating the cell with the test compound for a time sufficient to elicit a response;

fixing and permeabilizing the cell;

immersing said permeabilized cell in a hybridization solution containing an excess of a first set of at least twelve different non-overlapping hybridization probes consisting of DNA, RNA or a mixture of DNA and RNA free of non-natural nucleotides, that are 7-30 nucleotides long, that have sequences complementary to said first target sequence, and that are each singly labeled with the same first fluorophore, said at least twelve different non-overlapping hybridization probes are complementary to the at least 12 different probe-binding regions of the first target sequence, respectively, whereby individual RNA molecules in the cell are rendered sufficiently fluorescent to be seen as spots in fluorescence microscopy;

washing said cell to remove unbound probes;

detecting an amount of a distribution of said spots of the first fluorophore; and comparing said amount or said distribution with that obtained from a control cell similarly treated but without the test compound.

15. The method according to claim 14 wherein said first target sequence includes at least 30 different probe-binding regions and said first set of probes includes at least 30 different probes.

16. The method according to claim 14 wherein the first target sequence is an mRNA sequence.

17. The method of claim 14 wherein the step of detecting includes imaging to show said spots of the first fluorophore, processing the image to enhance the spots, and analyzing the enhanced spots utilizing an intensity threshold at which the number of spots is insensitive to threshold value.

18. The method of claim 17 wherein the step of detection includes counting said spots corresponding to single molecules of the RNA to obtain a gene expression profile.

* * * * *